United States Patent
Luecking et al.

(10) Patent No.: US 7,312,225 B2
(45) Date of Patent: Dec. 25, 2007

(54) MACROCYCLIC PYRIMIDINES, THEIR PRODUCTION AND USE AS PHARMACEUTICAL AGENTS

(75) Inventors: Ulrich Luecking, Berlin (DE); Gerhard Siemeister, Berlin (DE); Martina Schaefer, Berlin (DE); Hans Briem, Bremen (DE)

(73) Assignee: Bayer Schering Pharma AG, Berlin (DE)

(*) Notice: Subject to any disclaimer, the term of this patent is extended or adjusted under 35 U.S.C. 154(b) by 492 days.

(21) Appl. No.: 10/644,076

(22) Filed: Aug. 20, 2003

(65) Prior Publication Data
US 2004/0209895 A1 Oct. 21, 2004

Related U.S. Application Data

(60) Provisional application No. 60/413,444, filed on Sep. 26, 2002.

(30) Foreign Application Priority Data
Aug. 21, 2002 (DE) .................. 102 39 042

(51) Int. Cl.
A61P 35/00 (2006.01)
A61K 31/505 (2006.01)
C07D 245/00 (2006.01)

(52) U.S. Cl. ............ 514/267; 514/257; 540/460; 540/469; 540/472

(58) Field of Classification Search ............. 514/267, 514/257; 540/460, 469, 472
See application file for complete search history.

(56) References Cited

U.S. PATENT DOCUMENTS

| 4,138,558 A | 2/1979 | Orita et al. ............ 544/189 |
| 6,235,746 B1 | 5/2001 | Davis et al. ............ 514/275 |

FOREIGN PATENT DOCUMENTS

| WO | WO 0039101 | 7/2000 |
| WO | WO 0164654 | 9/2001 |
| WO | WO 0204429 | 1/2002 |
| WO | WO 0220512 | 3/2002 |

OTHER PUBLICATIONS

Knockaert, et al., Pharmacological Inhibitors of Cyclin-Dependent Kinases, TRENDS in Pharmacological Sciences, vol. 23, No. 9, pp. 417-425, Sep. 2002.*
Jhaumeer-Laulloo et al., "Synthesis and anti-HIV activity of novel macrocyclic benzamides with a disulfide bridge," Indian J. Chem., 2000, pp. 842-846, vol. 39B, No. 11, XP009020915, figure 12.
Database Crossfire Beilstein 'Online!, Beilstein Institut zur Foerderung der Chemischen Wissenschaften, XP002261263, Database Accession No. 943696 (BRN), Frankfurt am Main, DE; & Bull. Soc. Sci. Photogr. Jpn., 1969, p. 41, vol. 19.

* cited by examiner

Primary Examiner—Brenda Coleman
(74) Attorney, Agent, or Firm—Millen, White, Zelano & Branigan, P.C.

(57) ABSTRACT

Macrocyclic pyrimidine derivatives of general formula I

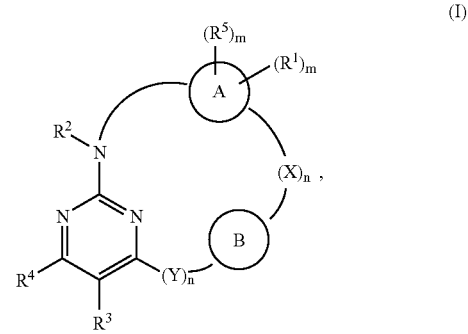

in which $R^1$ to $R^5$, X, Y, A, B, m and n have the meanings that are contained in the description, as inhibitors of the cyclin-dependent kinase, their processes for production as well as their use as medications for treating various diseases are described.

9 Claims, 1 Drawing Sheet

MACROCYCLIC PYRIMIDINES, THEIR PRODUCTION AND USE AS PHARMACEUTICAL AGENTS

This application claims benefit under 35 U.S.C. 119(e) to provisional application 60/413,444, filed Sep. 26, 2002.

This invention relates to macrocyclic pyrimidine derivatives, their processes for production as well as their use as medication for treating various diseases.

The cyclin-dependent kinases (cyclin-dependent kinase, CDK) are an enzyme family that plays an important role in the regulation of the cell cycle and thus presents an especially advantageous purpose for the development of small inhibitory molecules. Selective inhibitors of the CDKs can be used for treating cancer or other diseases that are caused by disorders of cell proliferation.

Receptor tyrosine kinases and their ligands that specifically regulate the function of endothelial cells are involved in a decisive way in the physiological as well as the pathogenic angiogeneses. Of special importance here is the Vascular Endothelial Growth Factors (VEGF)/VEGF receptor system. In pathological situations that accompany enhanced neovascularization, such as, e.g., tumor diseases, an increased expression of angiogenic growth factors and their receptors was found. Inhibitors of the VEGF/VEGF-receptor system can inhibit the formation of a blood vessel system in the tumor, so that the tumors are separated from the oxygen and nutrient supply and thus inhibit the tumor growth.

Pyrimidines and analogs are already described as active ingredients, such as, for example, the 2-anilino-pyrimidines as fungicides (DE 4029650) or substituted pyrimidine derivatives for treating neurological or neurodegenerative diseases (WO 99/19305). As CDK inhibitors, the most varied pyrimidine derivatives are described, for example bis(anilino)pyrimidine derivatives (WO 00/12486), 2-amino-4-substituted pyrimidines (WO 01/14375), purines (WO 99/02162), 5-cyano-pyrimidines (WO 02/04429), anilinopyrimidines (WO 00/12486) and 2-hydroxy-3-N,N-dimethylaminopropoxy-pyrimidines (WO 00/39101).

The object of this invention is to provide compounds that have better properties than the already known compounds. It has now been found, surprisingly enough, that the substances according to the invention inhibit either cyclin-dependent kinases and VEGF-receptor tyrosine kinases or cyclin-dependent kinases or VEGF-receptor tyrosine kinases already in the nanomolar range and thus can inhibit the proliferation of tumor cells and/or tumor angiogenesis. They are thus clearly distinguishable from other already known CDK- or VEGF-R inhibitors, such as, e.g., olomoucine and roscovitin.

It has now been found that compounds of general formula I

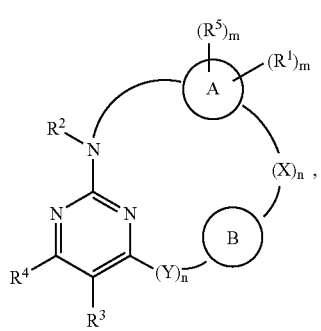

(I)

in which

A stands for $C_3$-$C_{12}$-arylene or $C_3$-$C_{18}$-heteroarylene,

B stands for a bond or for $C_1$-$C_{12}$-alkylene, $C_2$-$C_{12}$-alkenylene, $C_2$-$C_{12}$-alkinylene, $C_3$-$C_8$-cycloalkylene, $C_3$-$C_{12}$-heterocycloalkylene, $C_3$-$C_{12}$-arylene or $C_3$-$C_{18}$-heteroarylene that is optionally substituted in one or more places in the same way or differently with hydroxy, halogen, cyano, nitro, $C_1$-$C_6$-alkyl, $C_2$-$C_6$-alkenyl, $C_2$-$C_6$-alkinyl, $C_3$-$C_{10}$-cycloalkyl, $C_1$-$C_6$-hydroxyalkyl, $C_3$-$C_{12}$-aryl, $C_3$-$C_{18}$-heteroaryl, —$(CH_2)_p$—$C_3$-$C_{12}$-aryl, —$(CH_2)_p$—$C_3$-$C_{18}$-heteroaryl, phenyl-$(CH_2)_p$—$R^{10}$, —$(CH_2)_p PO_3(R^{10})_2$, —$(CH_2)_p SO_3 R^8$ or with the group —$NR^8R^9$, —$NR^8COR^9$, —$NR^8CSR^9$, —$NR^8SOR^9$, —$NR^8SO_2R^9$, —$NR^8CONR^8R^9$, —$NR^8COOR^9$, —$NR^8C(NH)NR^9R^{10}$, —$NR^8CSNR^9R^{10}$, —$NR^8SONR^9R^{10}$, —$NR^8SO_2NR^9R^{10}$, —$COR^8$, —$CSR^8$, —$S(O)R^8$, —$S(O)_2R^8$, —$S(O)_2NR^8R^9$, —$SO_3R^8$, —$CO_2R^8$, —$CONR^8R^9$, —$CSNR^8R^9$, —$SR^8$ or —$CR^8(OH)$—$R^9$, X and Y, in each case independently of one another, stand for oxygen, sulfur or for the group =$NR^{11}$—, —$NR^{11}(CH_2)$—, —$NR^{11}O$—, —$ONR^{11}$—, =$CR^6R^7$, =$C$=$O$, =$C$=$S$, =$SO$, =$SO_2$, —$C(O)O$—, —$OC(O)$—, —$S(O)O$—, —$OS(O)$—, —$S(O)_2O$—, —$OS(O)_2$—, —$CONR^8$—, —$N(COR^8)$—, —$N(COOR^8)$, —$N(CONR^8R^9)$—, —$NR^8CO$—, —$OCONR^8$—, —$NR^8C(O)O$—, —$CSNR^8$—, —$NR^8CS$—, —$OCSNR^8$—, —$NR^8CSO$—, —$SONR^8$—, —$NR^8SO$—, —$SO_2NR^8$—, —$S(O)_2N(COR^8)$—, —$NR^8SO_2$—, —$NR^8CONR^9$—, —$NR^8CSNR^9$—, —$NR^8SONR^9$—, —$NR^8SO_2NR^9$—, —$NR^8C(O)NR^9$— or —$NR^8C(S)NR^9$—, $R^1$ and $R^5$, in each case independently of one another, stand for hydrogen, hydroxy, halogen, nitro, cyano, $C_1$-$C_6$-alkyl, $C_1$-$C_6$-alkenyl, $C_1$-$C_6$-alkinyl, $C_3$-$C_{10}$-cycloalkyl, $C_3$-$C_{12}$-aryl, $C_3$-$C_{18}$-heteroaryl or for the group —$C_1$-$C_6$-alkyloxy-$C_1$-$C_6$-alkyloxy, —$(CH_2)_p$—$C_3$-$C_{12}$-aryl, —$(CH_2)_p$—$C_3$-$C_{18}$-heteroaryl, phenyl-$(CH_2)_p$—$R^{10}$, —$(CH_2)_p PO_3(R^{10})_2$, —$NR^8R^9$, —$NR^8COR^9$, —$NR^8CSR^9$, —$NR^8SOR^9$, —$NR^8SO_2R^9$, —$NR^8CONR^9R^{10}$, —$NR^8COOR^9$, —$NR^8C(NH)NR^9R^{10}$, —$NR^8CSNR^9R^{10}$, —$NR^8SONR^9R^{10}$, —$NR^8SO_2NR^9R^{10}$, —$COR^8$, —$CSR^8$, —$S(O)R^8$, —$S(O)(NH)R^8$, —$S(O)_2R^8$, —$S(O)_2NR^8R^9$, —$S(O)_2N$=$CH$—$NR^8R^9$, —$S_3R^8$, —$CO_2H$, —$CO_2R^8$, —$CONR^8R^9$, —$CSNR^8R^9$, —$SR^8$ or —$CR^8(OH)$—$R^9$, or for $C_1$-$C_{10}$-alkyl, $C_2$-$C_{10}$-alkenyl, $C_2$-$C_{10}$-alkinyl, $C_3$-$C_{10}$-cycloalkyl, $C_3$-$C_{12}$-aryl or $C_3$-$C_{18}$-heteroaryl that is substituted in one or more places in the same way or differently with hydroxy, $C_1$-$C_6$-alkoxy, halogen, phenyl or with the group —$NR^3R^4$, and the phenyl, $C_3$-$C_{10}$-cycloalkyl, $C_3$-$C_{12}$-aryl, $C_3$-$C_{18}$-heteroaryl, —$(CH_2)_p$—$C_3$-$C_{12}$-aryl and —$(CH_2)_p$—$C_3$-$C_{18}$-heteroaryl itself optionally can be substituted in one or more places in the same way or differently with halogen, hydroxy, $C_1$-$C_6$-alkyl, $C_1$-$C_6$-alkoxy, or with the group —$CF_3$ or —$OCF_3$, and the ring of the $C_3$-$C_{10}$-cycloalkyl and the $C_1$-$C_{10}$-alkyl optionally can be interrupted by one or more nitrogen, oxygen and/or sulfur atoms and/or can be interrupted by one or more =$C$=$O$ groups in the ring and/or optionally one or more possible double bonds can be contained in the ring, $R^2$ stands for hydrogen or $C_1$-$C_{10}$-alkyl, $R^3$ stands for hydrogen, halogen, nitro, cyano, $C_1$-$C_{10}$-alkyl, halo-$C_1$-$C_{10}$-alkyl, $C_2$-$C_{10}$-alkenyl, $C_2$-$C_{10}$-alkinyl, $C_3$-$C_{10}$-cycloalkyl, hydroxy, $C_1$-$C_6$-alkoxy, $C_1$-$C_6$-alkylthio, amino, —NH—$(CH_2)_p$—$C_3$-$C_{10}$-cycloalkyl, $C_1$-$C_6$-hydroxyalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, —NHC$_1$-$C_6$-alkyl, —N($C_1$-$C_6$-alkyl)$_2$, —SO($C_1$-$C_6$-alkyl), —SO$_2$($C_1$-$C_6$-alkyl), $C_1$-$C_6$-alkanoyl, —CONR$^8$R$^9$, —COR$^{10}$, $C_1$-$C_6$-alkylOAc, carboxy, $C_3$-$C_{12}$-aryl, $C_3$-$C_{18}$-heteroaryl, —$(CH_2)_p$—$C_3$-$C_2$-aryl, —$(CH_2)_p$—$C_3$-$C_{18}$-heteroaryl, phenyl-$(CH_2)_p$—R$^{10}$, —$(CH_2)_p$PO$_3$(R$^{10}$)$_2$ or for the group —NR$^8$R$^9$, or for $C_1$-$C_{10}$-alkyl, $C_2$-$C_{10}$-alkenyl, $C_2$-$C_{10}$-alkinyl, $C_3$-$C_{10}$-cycloalkyl, $C_3$-$C_{12}$-aryl or $C_3$-$C_{18}$-heteroaryl that is substituted in one or more places in the same way or differently with hydroxy, halogen, $C_1$-$C_6$-alkoxy, $C_1$-$C_6$-alkylthio, amino, cyano, $C_1$-$C_6$-alkyl, —NH—$(CH_2)_p$—$C_3$-$C_{10}$-cycloalkyl, $C_3$-$C_{10}$-cycloalkyl, $C_1$-$C_6$-hydroxyalkyl, $C_2$-$C_6$-alkenyl, $C_2$-$C_6$-alkinyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, —NHC$_1$-$C_6$-alkyl, —N($C_1$-$C_6$-alkyl)$_2$, —SO($C_1$-$C_6$-alkyl), —SO$_2$($C_1$-$C_6$-alkyl), $C_1$-$C_6$-alkanoyl, —CONR$^8$R$^9$, —COR$^{10}$, $C_1$-$C_6$-alkylOAc, carboxy, $C_3$-$C_{12}$-aryl, $C_3$-$C_{18}$-heteroaryl, —$(CH_2)_p$—$C_3$-$C_{12}$-aryl, —$(CH_2)_p$—$C_3$-$C_{18}$-heteroaryl, phenyl-$(CH_2)_p$—R$^{10}$, —$(CH_2)_p$PO$_3$(R$^{10}$)$_2$ or with the group —NR$^8$R$^9$, and the phenyl, $C_3$-$C_{10}$-cycloalkyl, $C_3$-$C_{12}$-aryl, $C_3$-$C_{18}$-heteroaryl, —$(CH_2)_p$—$C_3$-$C_{12}$-aryl and —$(CH_2)_p$—$C_3$-$C_{18}$-heteroaryl itself optionally can be substituted in one or more places in the same way or differently with halogen, hydroxy, $C_1$-$C_6$-alkyl, $C_1$-$C_6$-alkoxy, or with the group —CF$_3$ or —OCF$_3$, and the ring of the $C_3$-$C_{10}$-cycloalkyl and the $C_1$-$C_{10}$-alkyl optionally can be interrupted by one or more nitrogen, oxygen and/or sulfur atoms and/or can be interrupted by one or more =C=O groups in the ring and/or optionally one or more possible double bonds can be contained in the ring, R$^4$ stands for hydrogen, halogen or $C_1$-$C_4$-alkyl,

R$^6$, R$^7$, R$^8$,

R$^9$, R$^{10}$ and R$^{11}$, in each case independently of one another, stand for hydrogen or for $C_1$-$C_{10}$-alkyl, $C_2$-$C_{10}$-alkenyl, $C_2$-$C_{10}$-alkinyl, $C_3$-$C_{10}$-cycloalkyl, $C_3$-$C_{12}$-aryl or $C_3$-$C_{18}$-heteroaryl that is optionally substituted in one or more places in the same way or differently with hydroxy, halogen, $C_1$-$C_{12}$-alkoxy, $C_1$-$C_6$-alkylthio, amino, cyano, $C_1$-$C_6$-alkyl, —NH—$(CH_2)_p$—$C_3$-$C_{10}$-cycloalkyl, $C_3$-$C_{10}$-cycloalkyl, $C_1$-$C_6$-hydroxyalkyl, $C_2$-$C_6$-alkenyl, $C_2$-$C_6$-alkinyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, —NHC$_1$-$C_6$-alkyl, —N($C_1$-$C_6$-alkyl)$_2$, —SO($C_1$-$C_6$-alkyl), —SO$_2$($C_1$-$C_6$-alkyl), $C_1$-$C_6$-alkanoyl, —CONR$^8$R$^9$, —COR$^{10}$, $C_1$-$C_6$-alkylOAc, carboxy, $C_3$-$C_{12}$-aryl, $C_3$-$C_8$-heteroaryl, —$(CH_2)_p$—$C_3$-$C_{12}$-aryl, —$(CH_2)_p$—$C_3$-$C_{18}$-heteroaryl, phenyl-$(CH_2)_p$—R$^{10}$, —$(CH_2)_p$PO$_3$(R$^{10}$)$_2$ or with the group —NR$^8$R$^9$, and the phenyl, $C_3$-$C_{10}$-cycloalkyl, $C_3$-$C_{12}$-aryl, $C_3$-$C_{18}$-heteroaryl, —$(CH_2)_p$—$C_3$-$C_{12}$-aryl and —$(CH_2)_p$—$C_3$-$C_{18}$-heteroaryl itself optionally can be substituted in one or more places in the same way or differently with halogen, hydroxy, $C_1$-$C_6$-alkyl, $C_1$-$C_6$-alkoxy, or with the group —CF$_3$ or —OCF$_3$, and the ring of the $C_3$-$C_{10}$-cycloalkyl and the $C_1$-$C_{10}$-alkyl optionally can be interrupted by one or more nitrogen, oxygen and/or sulfur atoms and/or can be interrupted by one or more =C=O groups in the ring and/or optionally one or more possible double bonds can be contained in the ring, m stands for 0 to 8, and n and p stand for 0 to 6, as well as isomers, diastereomers, enantiomers and salts thereof, overcome the known drawbacks.

Alkyl is defined in each case as a straight-chain or branched alkyl radical, such as, for example, methyl, ethyl, propyl, isopropyl, butyl, isobutyl, sec-butyl, tert-butyl, pentyl, isopentyl, hexyl, heptyl, octyl, nonyl and decyl.

Alkoxy is defined in each case as a straight-chain or branched alkoxy radical, such as, for example, methyloxy, ethyloxy, propyloxy, isopropyloxy, butyloxy, isobutyloxy, sec-butyloxy, pentyloxy, isopentyloxy, hexyloxy, heptyloxy, octyloxy, nonyloxy, decyloxy, undecyloxy or dodecyloxy.

Alkylthio is defined in each case as a straight-chain or branched alkylthio radical, such as, for example, methylthio, ethylthio, propylthio, isopropylthio, butylthio, isobutylthio, sec-butylthio, tert-butylthio, pentylthio, isopentylthio or hexylthio.

Cycloalkyls are defined as monocyclic alkyl rings, such as cyclopropyl, cyclobutyl, cyclopentyl, cyclohexyl or cycloheptyl, cyclooctyl, cyclononyl or cyclodecyl, but also bicyclic rings or tricyclic rings, such as, for example, adamantanyl.

Heterocycloalkyl stands for an alkyl ring that comprises 3-12 carbon atoms and that instead of the carbon contains one or more heteroatoms that are the same or different, such as, e.g., oxygen, sulfur or nitrogen.

As heterocycloalkyls, there can be mentioned, e.g.: oxiranyl, oxethanyl, aziridinyl, azetidinyl, tetrahydrofuranyl, pyrrolidinyl, dioxolanyl, imidazolidinyl, pyrazolidinyl, dioxanyl, piperidinyl, morpholinyl, dithianyl, thiomorpholinyl, piperazinyl, trithianyl, quinuclidinyl, etc.

The ring systems, in which optionally one or more possible double bonds can be contained in the ring, are defined as, for example, cycloalkenyls, such as cyclopropenyl, cyclobutenyl, cyclopentenyl, cyclohexenyl, and cycloheptenyl, whereby the linkage can be carried out both to the double bond and to the single bonds.

Halogen is defined in each case as fluorine, chlorine, bromine or iodine.

In each case, the alkenyl- and alkinyl substituents are straight-chain or branched, whereby, for example, the following radicals are meant: vinyl, propen-1-yl, propen-2-yl, but-1-en-1-yl, but-1-en-2-yl, but-2-en-1-yl, but-2-en-2-yl, 2-methyl-prop-2-en-1-yl, 2-methyl-prop-1-en-1-yl, but-1-en-3-yl, ethinyl, prop-1-in-1-yl, but-1-in-1-yl, but-2-in-1-yl, but-3-en-1-yl, and allyl.

In each case, the aryl radical has 6-12 carbon atoms, such as, for example, naphthyl, biphenyl and, in particular, phenyl.

In each case, the heteroaryl radical comprises 3-18 ring atoms and instead of carbon can contain in the ring one or more heteroatoms that are the same or different, such as oxygen, nitrogen or sulfur, and can be monocyclic, bicyclic or tricyclic and in addition can be benzocondensed in each case.

For example, there can be mentioned: thienyl, furanyl, pyrrolyl, oxazolyl, thiazolyl, imidazolyl, pyrazolyl, isoxazolyl, isothiazolyl, oxadiazolyl, triazolyl, thiadiazolyl, etc. and benzo derivatives thereof, such as, e.g., benzofuranyl, benzothienyl, benzoxazolyl, benzimidazolyl, indazolyl, indolyl, isoindolyl, etc.; or pyridyl, pyridazinyl, pyrimidinyl, pyrazinyl, triazinyl, etc. and benzo derivatives thereof, such as, e.g., quinolyl, isoquinolyl, etc.; or azocinyl, indolizinyl, purinyl, etc., and benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, oxepinyl, 1,4-benzodioxane, etc.

If an acid group is included, the physiologically compatible salts of organic and inorganic bases are suitable as salts, such as, for example, the readily soluble alkali and alkaline-earth salts, as well as N-methyl-glucamine, dimethyl glucamine, ethyl glucamine, lysine, 1,6-hexadiamine, ethanolamine, glucosamine, sarcosine, serinol, tris-hydroxy-methyl-amino-methane, aminopropanediol, Sovak base, and 1-amino-2,3,4-butanetriol.

If a basic group is included, the physiologically compatible salts of organic and inorganic acids are suitable, such as hydrochloric acid, sulfuric acid, phosphoric acid, citric acid, and tartaric acid, i.a.

Those compounds of general formula (I), in which

A stands for phenylene or thiophenylene,

B stands for a bond or for $C_1$-$C_{12}$-alkylene, $C_2$-$C_{12}$-alkenylene, $C_2$-$C_{12}$-alkinylene, $C_3$-$C_8$-cycloalkylene, $C_3$-$C_{12}$-heterocycloalkylene, $C_3$-$C_{12}$-arylene or $C_3$-$C_{18}$-heteroarylene that is optionally substituted in one or more places in the same way or differently with hydroxy, halogen, cyano, nitro, $C_1$-$C_6$-alkyl, $C_2$-$C_6$-alkenyl, $C_2$-$C_6$-alkinyl, $C_3$-$C_{10}$-cycloalkyl, $C_1$-$C_6$-hydroxyalkyl, $C_3$-$C_{12}$-aryl, $C_3$-$C_{18}$-heteroaryl, —$(CH_2)_p$—$C_3$-$C_{12}$-aryl, —$(CH_2)_p$—$C_3$-$C_{18}$-heteroaryl, phenyl-$(CH_2)_p$—$R^{10}$, —$(CH_2)_p PO_3(R^{10})_2$, —$(CH_2)_p SO_3 R^8$ or with the group-$NR^8R^9$, —$NR^8COR^9$, —$NR^8CSR^9$, —$NR^8SOR^9$, —$NR^8SO_2R^9$, —$NR^8CONR^8R^9$, —$NR^8COOR^9$, —$NR^8C(NH)NR^9R^{10}$, —$NR^8CSNR^9R^{10}$, —$NR^8SONR^9R^{10}$, —$NR^8SO_2NR^9R^{10}$, —$COR^8$, —$CSR^8$, —$S(O)R^8$, —$S(O)_2R^8$, —$S(O)_2NR^8R^9$, —$SO_3R^8$, —$CO_2R^8$, —$CONR^8R^9$, —$CSNR^8R^9$, —$SR^8$ or —$CR^8(OH)$—$R^9$, X and Y, in each case independently of one another, stand for oxygen, sulfur or for the group —$NR^{11}$—, —$NR^{11}(CH_2)$—, —$NR^{11}O$—, —$ONR^{11}$—, =$CR^6R^7$, =C=O, =C=S, =SO, =$SO_2$, —$C(O)O$—, —$OC(O)$—, —$S(O)O$—, —$OS(O)$—, —$S(O)_2O$—, —$OS(O)_2$—, —$CONR^8$—, —$N(COR^8)$—, —$N(COOR^8)$—, —$N(CONR^8R^9)$—, —$NR^8CO$—, —$OCONR^8$—, —$NR^8C(O)O$—, —$CSNR^8$—, —$NR^8CS$—, —$OCSNR^8$—, —$NR^8CSO$—, —$SONR^8$—, —$NR^8SO$—, —$SO_2NR^8$—, —$S(O)_2N(COR^8)$—, —$NR^8SO_2$—, —$NR^8CONR^9$—, —$NR^8CSNR^9$—, —$NR^8SONR^9$—, —$NR^8SO_2NR^9$—, —$NR^8C(O)NR^9$— or —$NR^8C(S)NR^9$—, $R^1$ and $R^5$, in each case independently of one another, stand for hydrogen, hydroxy, halogen, nitro, cyano, $C_1$-$C_6$-alkyl, $C_1$-$C_6$-alkenyl, $C_1$-$C_6$-alkinyl, $C_3$-$C_{10}$-cyploalkyl, $C_3$-$C_{12}$-aryl, $C_3$-$C_{18}$-heteroaryl or for the group —$C_1$-$C_6$-alkyloxy-$C_1$-$C_6$-alkyloxy, —$(CH_2)_p$—$C_3$-$C_{12}$-aryl, —$(CH_2)_p$—$C_3$-$C_{18}$-heteroaryl, phenyl-$(CH_2)_p$—$R^{10}$, —$(CH_2)_p PO_3(R^{10})_2$, —$NR^8R^9$, —$NR^8COR^9$, —$NR^8CSR^9$, —$NR^8SOR^9$, —$NR^8SO_2R^9$, —$NR^8CONR^9R^{10}$, —$NR^8COOR^9$, —$NR^8C(NH)NR^9R^{10}$, —$NR^8CSNR^9R^{10}$, —$NR^8SONR^9R^{10}$, —$NR^8SO_2NR^9R^{10}$, —$COR^8$, —$CSR^8$, —$S(O)R^8$, —$S(O)(NH)R^8$, —$S(O)_2R^8$, —$S(O)_2NR^8R^9$, —$S(O)_2N$=$CH$—$NR^8R^9$, —$SO_3R^8$, —$CO_2H$, —$CO_2R^8$, —$CONR^8R^9$, —$CSNR^8R^9$, —$SR^8$ or —$CR^8(OH)$—$R^9$, or for $C_1$-$C_{10}$-alkyl, $C_2$-$C_{10}$-alkenyl, $C_2$-$C_{10}$-alkinyl, $C_3$-$C_{10}$-cycloalkyl, $C_3$-$C_{12}$-aryl or $C_3$-$C_{18}$-heteroaryl that is substituted in one or more places in the same way or differently with hydroxy, $C_1$-$C_6$-alkoxy, halogen, phenyl or with the group —$NR^3R^4$, and the phenyl, $C_3$-$C_{10}$-cycloalkyl, $C_3$-$C_{12}$-aryl, $C_3$-$C_{18}$-heteroaryl, —$(CH_2)_p$—$C_3$-$C_{12}$-aryl and —$(CH_2)_p$—$C_3$-$C_{18}$-heteroaryl itself optionally can be substituted in one or more places in the same way or differently with halogen, hydroxy, $C_1$-$C_6$-alkyl, $C_1$-$C_6$-alkoxy, or with the group —$CF_3$ or —$OCF_3$, and the ring of $C_3$-$C_{10}$-cycloalkyl and the $C_1$-$C_{10}$-alkyl optionally can be interrupted by one or more nitrogen, oxygen and/or sulfur atoms and/or can be interrupted by one or more =C=O groups in the ring and/or optionally one or more double bonds can be contained in the ring, $R^2$ stands for hydrogen or $C_1$-$C_{10}$-alkyl, $R^3$ stands for hydrogen, halogen, nitro, cyano, $C_1$-$C_{10}$-alkyl, halo-$C_1$-$C_{10}$-alkyl, $C_2$-$C_{10}$-alkenyl, $C_2$-$C_{10}$-alkinyl, $C_3$-$C_{10}$-cycloalkyl, hydroxy, $C_1$-$C_6$-alkoxy, $C_1$-$C_6$-alkylthio, amino, —NH—$(CH_2)_p$—$C_3$-$C_{10}$-cycloalkyl, $C_1$-$C_6$-hydroxyalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, —$NHC_1$-$C_6$-alkyl, —$N(C_1$-$C_6$-alkyl)$_2$, —$SO(C_1$-$C_6$-alkyl), —$SO_2(C_1$-$C_6$-alkyl), $C_1$-$C_6$-alkanoyl, —$CONR^8R^9$, —$COR^{10}$, $C_1$-$C_6$-alkylOAc, carboxy, $C_3$-$C_{12}$-aryl, $C_3$-$C_{18}$-heteroaryl, —$(CH_2)_p$—$C_3$-$C_{12}$-aryl, —$(CH_2)_p$—$C_3$-$C_{18}$-heteroaryl, phenyl-$(CH_2)_p$—$R^{10}$, —$(CH_2)_p PO_3(R^{10})_2$ or for the group —$NR^8R^9$, or for $C_1$-$C_{10}$-alkyl, $C_2$-$C_{10}$-alkenyl, $C_2$-$C_{10}$-alkinyl, $C_3$-$C_{10}$-cycloalkyl, $C_3$-$C_{12}$-aryl or $C_3$-$C_{18}$-heteroaryl that is substituted in one or more places in the same way or differently with hydroxy, halogen, $C_1$-$C_6$-alkoxy, $C_1$-$C_6$-alkylthio, amino, cyano, $C_1$-$C_6$-alkyl, —NH—$(CH_2)_p$—$C_3$-$C_{10}$-cycloalkyl, $C_3$-$C_{10}$-cycloalkyl, $C_1$-$C_6$-hydroxyalkyl, $C_2$-$C_6$-alkenyl, $C_2$-$C_6$-alkinyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, —$NHC_1$-$C_6$-alkyl, —$N(C_1$-$C_6$-alkyl)$_2$, —$SO(C_1$-$C_6$-alkyl), —$SO_2(C_1$-$C_6$-alkyl), $C_1$-$C_6$-alkanoyl, —$CONR^8R^9$, —$COR^{10}$, $C_1$-$C_6$-alkylOAc, carboxy, $C_3$-$C_{12}$-aryl, $C_3$-$C_{18}$-heteroaryl, —$(CH_2)_p$—$C_3$-$C_{12}$-aryl, —$(CH_2)_p$—$C_3$-$C_{18}$-heteroaryl, phenyl-$(CH_2)_p$—$R^{10}$, —$(CH_2)_p PO_3(R^{10})_2$ or with the group —$NR^8R^9$; and the phenyl, $C_3$-$C_{10}$-cycloalkyl, $C_3$-$C_{12}$-aryl$_1$, $C_3$-$C_{18}$-heteroaryl, —$(CH_2)_p$—$C_3$-$C_{12}$-aryl and —$(CH_2)_p$—$C_3$-$C_{18}$-heteroaryl itself optionally can be substituted in one or more places in the same way or differently with halogen, hydroxy, $C_1$-$C_6$-alkyl, $C_1$-$C_6$-alkoxy, or with the group —$CF_3$ or —$OCF_3$, and the ring of the $C_3$-$C_{10}$-cycloalkyl and the $C_1$-$C_{10}$-alkyl optionally can be interrupted by one or more nitrogen, oxygen, and/or sulfur atoms and/or can be interrupted by one or more =C=O groups in the ring and/or optionally one or more possible double bonds can be contained in the ring, $R^4$ stands for hydrogen, halogen or $C_1$-$C_4$-alkyl, $R^6$ $R^7$ $R^8$, $R^9$, $R^{10}$ and $R^{11}$, in each case independently of one another, stand for hydrogen or for $C_1$-$C_{10}$-alkyl, $C_2$-$C_{10}$-alkenyl, $C_2$-$C_{10}$-alkinyl, $C_3$-$C_{10}$-cycloalkyl, $C_3$-$C_{12}$-aryl or $C_3$-$C_{18}$-heteroaryl that is optionally substituted in one or more places in the same way or differently with hydroxy, halogen, $C_1$-$C_{12}$-alkoxy, $C_1$-$C_6$-alkylthio, amino, cyano, $C_1$-$C_6$-alkyl, —NH—$(CH_2)_p$—$C_3$-$C_{10}$-cycloalkyl, $C_3$-$C_{10}$-cycloalkyl, $C_1$-$C_6$-hydroxyalkyl, $C_2$-$C_6$-alkenyl, $C_2$-$C_6$-alkinyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, —$NHC_1$-$C_6$-alkyl, —$N(C_1$-$C_6$-alkyl)$_2$, —$SO(C_1$-$C_6$- alkyl), —SO$_2$(C$_1$-C$_6$-alkyl), C$_1$-C$_6$-alkanoyl, —CONR$^8$R$^9$, —COR$^{10}$, C$_1$-C$_6$-alkylOAc, carboxy, C$_3$-C$_{12}$-aryl, C$_3$-C$_8$-heteroaryl, —(CH$_2$)$_p$—C$_3$-C$_{12}$-aryl, —(CH$_2$)$_p$—C$_3$-C$_{18}$-heteroaryl, phenyl-(CH$_2$)$_p$—R$^{10}$, —(CH$_2$)$_p$PO$_3$(R$^{10}$)$_2$ or with the group —NR$^8$R$^9$, and the phenyl, C$_3$-C$_{10}$-cycloalkyl, C$_3$-C$_{12}$-aryl, C$_3$-C$_{18}$-heteroaryl, —(CH$_2$)$_p$—C$_3$-C$_{12}$-aryl and —(CH$_2$)$_p$—C$_3$-C$_{18}$-heteroaryl itself optionally can be substituted in one or more places in the same way or differently with halogen, hydroxy, C$_1$-C$_6$-alkyl, C$_1$-C$_6$-alkoxy, or with the group —CF$_3$ or —OCF$_3$, and the ring of C$_3$-C$_{10}$-cycloalkyl and the C$_1$-C$_{10}$-alkyl optionally can be interrupted by one or more nitrogen, oxgyen and/or sulfur atoms, and/or can be interrupted by one or more =C=O groups in the ring and/or optionally one or more possible double bonds can be contained in the ring, m stands for 0 to 8, and n and p stand for 0 to 6, as well as isomers, diastereomers, enantiomers and salts thereof, are especially effective.

Those compounds of general formula (I) in which

A stands for phenylene or thiophenylene,

B stands for a bond or for C$_1$-C$_{12}$-alkylene, C$_3$-C$_8$-cycloalkylene or C$_3$-C$_{12}$-arylene that is optionally substituted in one or more places in the same way or differently with hydroxy, C$_1$-C$_6$-alkyl, C$_1$-C$_6$-hydroxyalkyl or —(CH$_2$)$_p$SO$_3$R$^8$, X and Y, in each case independently of one another, stand for oxygen or for the group —NR$^{11}$—, —NR$^{11}$(CH$_2$)—, —CONR$^8$—, —SO$_2$NR$^8$— or —NR$^8$CONR$^9$—, R$^1$ and R$^5$, in each case independently of one another, stand for hydrogen, halogen, nitro, C$_1$-C$_6$-alkyl, or for —NR$^8$R$^9$, —C$_1$-C$_6$-alkyloxy-C$_1$-C$_6$-alkyloxy or —S(O)$_2$NR$^8$R$^9$, R$^2$ stands for hydrogen, R$^3$ stands for hydrogen, halogen, cyano, C$_1$-C$_{10}$-alkyl or —CONR$^8$R$^9$, R$^4$ stands for hydrogen,

R$^8$,

R$^9$ and R$^{11}$, in each case independently of one another, stand for hydrogen or for C$_1$-C$_{10}$-alkyl, m stands for 0 to 4, and p stands for 0 to 6, as well as isomers, diastereomers, enantiomers and salts thereof, are especially effective.

Those compounds of general formula (I), in which

A stands for phenylene,

B stands for a bond or for C$_1$-C$_{12}$-alkylene, cyclohexylene or phenylene that is optionally substituted in one or more places in the same way or differently with hydroxy, C$_1$-C$_6$-alkyl, C$_1$-C$_6$-hydroxyalkyl or —(CH$_2$)SO$_3$R$^8$, X stands for oxygen or for the group —CONR$^8$—, —SO$_2$NR$^8$— or —NR$^8$CONR$^9$—, Y stands for oxygen or for the group —NR$^{11}$—, R$^1$ and R$^5$, in each case independently of one another, stand for hydrogen, amino, halogen, nitro, C$_1$-C$_6$-alkyl, or for the group —NR$^8$R$^9$, —C$_1$-C$_6$-alkyloxy-C$_1$-C$_6$-alkyloxy or —S(O)$_2$NR$^8$R$^9$, R$^2$ stands for hydrogen, R$^3$ stands for hydrogen, halogen, cyano, C$_1$-C$_{10}$-alkyl, or —CONR$^8$R$^9$, R$^4$ stands for hydrogen, R$^8$, R$^9$ and R$^{11}$, in each case independently of one another, stand for hydrogen or for methyl or isobutyl, m stands for 0 to 4, and p stands for 0 to 6, as well as isomers, diastereomers, enantiomers, and salts thereof, are selected.

In addition, those compounds of general formula (I), in which

A stands for phenylene,

B stands for a bond or for C$_1$-C$_{12}$-alkylene that is optionally substituted in one or more places in the same way or differently with hydroxy, C$_1$-C$_6$-hydroxyalkyl or —(CH$_2$)SO$_3$R$^8$, X stands for oxygen or for the group —SO$_2$NR$^8$— or —NR$^8$CONR$^9$—, Y stands for the group —NR$^{11}$—, R$^1$ and R$^5$, in each case independently of one another, stand for hydrogen, amino, halogen, nitro or for the group —S(O)$_2$NR$^8$R$^9$, R$^2$ stands for hydrogen, R$^3$ stands for halogen or cyano, R$^4$ stands for hydrogen, R$^8$, R$^9$ and R$^{11}$ in each case stand for hydrogen, and m stands for 0 to 4, as well as isomers, diastereomers, enantiomers and salts thereof, are selected.

In particular, those compounds of general formula (I), in which

A stands for thiophenylene,

B stands for a bond or for C$_1$-C$_{12}$-alkylene,

X stands for the group —SO$_2$NR$^8$—,

Y stands for the group —NR$^{11}$—,

R$^3$ stands for halogen,

R$^1$, R$^2$, R$^4$, R$^5$,

R$^8$, R$^9$ and R$^{11}$ in each case stand for hydrogen, m stands for 0 to 2, as well as isomers, diastereomers, enantiomers and salts thereof, are selected.

It was also found that compounds of general formula I

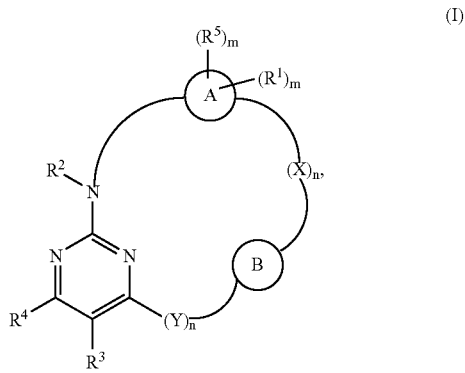

in which

A stands for C$_3$-C$_{12}$-arylene or C$_3$-C$_{18}$-heteroarylene,

B stands for a bond or for C$_1$-C$_{12}$-alkylene, C$_2$-C$_{12}$-alkenylene, C$_2$-C$_{12}$-alkinylene, C$_3$-C$_8$-cycloalkylene, C$_3$-C$_{12}$-heterocycloalkylene, C$_3$-C$_{12}$-arylene or C$_3$-C$_{18}$-heteroarylene that is optionally substituted in one or more places in the same way or differently with hydroxy, halogen, cyano, nitro, C$_1$-C$_6$-alkyl, C$_2$-C$_6$-alkenyl, C$_2$-C$_6$-alkinyl, C$_3$-C$_{10}$-cycloalkyl, C$_1$-C$_6$-hydroxyalkyl, C$_3$-C$_{12}$-aryl, C$_3$-C$_{18}$-heteroaryl, —(CH$_2$)$_p$—C$_3$-C$_{12}$-aryl, —(CH$_2$)$_p$—C$_3$-C$_{18}$-heteroaryl, phenyl-(CH$_2$)$_p$—R$^{10}$, —(CH$_2$)$_p$PO$_3$(R$^{10}$)$_2$ or with the group-NR$^8$R$^9$, —NR$^8$COR$^9$, —NR$^8$CSR$^9$, —NR$^8$SOR$^9$, —NR$^8$SO$_2$R$^9$, —NR$^8$CONR$^9$R$^{10}$, —NR$^8$COOR$^9$, —NR$^8$C(NH)NR$^9$R$^{10}$, —NR$^8$CSNR$^9$R$^{10}$, —NR$^8$SONR$^9$R$^{10}$, —NR$^8$SO$_2$NR$^9$R$^{10}$, —COR$^8$, —CSR$^8$, —S(O)R$^8$, —S(O)$_2$R$^8$, —S(O)$_2$NR$^8$R$^9$, —SO$_3$R$^8$, —CO$_2$R$^8$, CONR$^8$R$^9$, —CSNR$^8$R$^9$, —SR$^8$ or —CR$^8$(OH)—R$^9$, X and Y, in each case independently of one another, stand for oxygen, sulfur or for the group =NR$^{11}$, —NR$^{11}$O—, —ONR$^{11}$—, =CR$^6$R$^7$, =C=O, =C=S, =SO, =SO$_2$, —C(O)O—, —OC(O)—, —S(O)O—, —OS(O)—, —S(O)$_2$O—, —OS(O)$_2$—, —CONR$^8$—, —NR$^8$CO—, —OCONR$^8$—, —NR$^8$C(O)O—, —CSNR$^8$—, —NR$^8$CS—, —OCSNR$^8$—, —NR$^8$CSO—, —SONR$^8$—, —NR$^8$SO—, —SO$_2$NR$^8$—, —NR$^8$SO$_2$—, —NR$^8$CONR$^9$—, —NR$^8$CSNR$^9$—, —NR$^8$SONR$^9$—, —NR$^8$SO$_2$NR$^9$—, —NR$^8$C(O)NR$^9$— or —NR$^8$C(S)NR$^9$—, R$^1$ and R$^5$, in each case independently of one another, stand for hydrogen, hydroxy, halogen, nitro, cyano, C$_1$-C$_6$-alkyl, C$_1$-C$_6$-alkenyl, C$_1$-C$_6$-alkinyl, C$_3$-C$_{10}$-cycloalkyl, C$_3$-C$_{12}$-aryl, C$_3$-C$_{18}$-heteroaryl or for the group —(CH$_2$)$_p$—C$_3$-C$_{12}$-aryl, —(CH$_2$)$_p$—C$_3$-C$_{18}$-heteroaryl, phenyl-(CH$_2$)$_p$—R$^{10}$, —(CH$_2$)$_p$PO$_3$(R$^{10}$)$_2$, —NR$^8$R$^9$, —NR$^8$COR$^9$, —NR$^8$CSR$^9$, —NR$^8$SOR$^9$, —NR$^8$SO$_2$R$^9$, —NR$^8$CONR$^9$R$^{10}$, —NR$^8$COOR$^9$, —NR$^8$C(NH)NR$^9$R$^{10}$, —NR$^8$CSNR$^9$R$^{10}$, —NR$^8$SONR$^9$R$^{10}$, —NR$^8$SO$_2$NR$^9$R$^{10}$, —COR$^8$, —CSR$^8$, —S(O)R$^8$, —S(O)$_2$R$^8$, —S(O)$_2$NR$^8$R$^9$, —SO$_3$R$^8$, —CO$_2$H, —CO$_2$R$^8$, —CONR$^8$R$^9$, —CSNR$^8$R$^9$, —SR$^8$ or —CR$^8$(OH)—R$^9$, or for C$_1$-C$_{10}$-alkyl, C$_2$-C$_{10}$-alkenyl, C$_2$-C$_{10}$-alkinyl, C$_3$-C$_{10}$-cycloalkyl, C$_3$-C$_{12}$-aryl or C$_3$-C$_{18}$-heteroaryl that is substituted in one or more places in the same way or differently with hydroxy, C$_1$-C$_6$-alkoxy, halogen, phenyl or with the group —NR$^3$R$^4$, and the phenyl, C$_3$-C$_{10}$-cycloalkyl, C$_3$-C$_{12}$-aryl, C$_3$-C$_{18}$-heteroaryl, —(CH$_2$)$_p$—C$_3$-C$_{12}$-aryl and —(CH$_2$)$_p$—C$_3$-C$_{18}$-heteroaryl itself optionally can be substituted in one or more places in the same way or differently with halogen, hydroxy, C$_1$-C$_6$-alkyl, C$_1$-C$_6$-alkoxy, or with the group —CF$_3$ or —OCF$_3$, and the ring of the C$_3$-C$_{10}$-cycloalkyl and the C$_1$-C$_{10}$-alkyl optionally can be interrupted by one or more nitrogen, oxygen and/or sulfur atoms and/or can be interrupted by one or more =C=O groups in the ring and/or optionally one or more possible double bonds can be contained in the ring, R$^2$ stands for hydrogen or C$_1$-C$_{10}$-alkyl, R$^3$ stands for hydrogen, halogen, nitro, cyano, C$_1$-C$_{10}$-alkyl, halo-C$_1$-C$_{10}$-alkyl, C$_2$-C$_{10}$-alkenyl, C$_2$-C$_{10}$-alkinyl, C$_3$-C$_{10}$-cycloalkyl, hydroxy, C$_1$-C$_6$-alkoxy, C$_1$-C$_6$-alkylthio, amino, —NH—(CH$_2$)$_p$—C$_3$-C$_{10}$-cycloalkyl, C$_1$-C$_6$-hydroxyalkyl, C$_1$-C$_6$-alkoxy-C$_1$-C$_6$-alkyl, C$_1$-C$_6$-alkoxy-C$_1$-C$_6$-alkoxy-C$_1$-C$_6$-alkyl, —NHC$_1$-C$_6$-alkyl, —N(C$_1$-C$_6$-alkyl)$_2$, —SO(C$_1$-C$_6$-alkyl), —SO$_2$(C$_1$-C$_6$-alkyl), C$_1$-C$_6$-alkanoyl, —CONR$^8$R$^9$, —COR$^{10}$, C$_1$-C$_6$-alkylOAc, carboxy, C$_3$-C$_{12}$-aryl, C$_3$-C$_{18}$-heteroaryl, —(CH$_2$)$_p$—C$_3$-C$_{12}$-aryl, —(CH$_2$)$_p$—C$_3$-C$_{18}$-heteroaryl, phenyl-(CH$_2$)$_p$—R$^{10}$, —(CH$_2$)$_p$PO$_3$(R$^{10}$)$_2$ or for the group —NR$^8$R$^9$, or for C$_1$-C$_{10}$-alkyl, C$_2$-C$_{10}$-alkenyl, C$_2$-C$_{10}$-alkinyl, C$_3$-C$_{10}$-cycloalkyl, C$_3$-C$_{12}$-aryl or C$_3$-C$_{18}$-heteroaryl that is substituted in one or more places in the same way or differently with hydroxy, halogen, C$_1$-C$_6$-alkoxy, C$_1$-C$_6$-alkylthio, amino, cyano, C$_1$-C$_6$-alkyl, —NH—(CH$_2$)$_p$—C$_3$-C$_{10}$-cycloalkyl, C$_3$-C$_{10}$-cycloalkyl, C$_1$-C$_6$-hydroxyalkyl, C$_2$-C$_6$-alkenyl, C$_2$-C$_6$-alkinyl, C$_1$-C$_6$-alkoxy-C$_1$-C$_6$-alkyl, C$_1$-C$_6$-alkoxy-C$_1$-C$_6$-alkoxy-C$_1$-C$_6$-alkyl, —NHC$_1$-C$_6$-alkyl, —N(C$_1$-C$_6$-alkyl)$_2$, —SO(C$_1$-C$_6$-alkyl), —SO$_2$(C$_1$-C$_6$-alkyl), C$_1$-C$_6$-alkanoyl, —CONR$^8$R$^9$, —COR$^{10}$, C$_1$-C$_6$-alkylOAc, carboxy, C$_3$-C$_{12}$-aryl, C$_3$-C$_{18}$-heteroaryl, —(CH$_2$)$_p$—C$_3$-C$_{12}$-aryl, —(CH$_2$)$_p$—C$_3$-C$_{18}$-heteroaryl, phenyl-(CH$_2$)$_p$—R$^{10}$, —(CH$_2$)$_p$PO$_3$(R$^{10}$)$_2$ or with the group —NR$^8$R$^9$, and the phenyl, C$_3$-C$_{10}$-cycloalkyl, C$_3$-C$_{12}$-aryl, C$_3$-C$_{18}$-heteroaryl, —(CH$_2$)$_p$—C$_3$-C$_{12}$-aryl and —(CH$_2$)$_p$—C$_3$-C$_{18}$-heteroaryl itself optionally can be substituted in one or more places in the same way or differently with halogen, hydroxy, C$_1$-C$_6$-alkyl, C$_1$-C$_6$-alkoxy, or with the group —CF$_3$ or —OCF$_3$, and the ring of the C$_3$-C$_{10}$-cycloalkyl and the C$_1$-C$_{10}$-alkyl optionally can be interrupted by one or more nitrogen, oxygen and/or sulfur atoms and/or can be interrupted by one or more =C=O groups in the ring and/or optionally one or more possible double bonds can be contained in the ring, R$^4$ stands for hydrogen, halogen or C$_1$-C$_4$-alkyl,

R$^6$, R$^7$, R$^8$,

R$^9$, R$^{10}$ and R$^{11}$, in each case independently of one another, stand for hydrogen or for C$_1$-C$_{10}$-alkyl, C$_2$-C$_{10}$-alkenyl, C$_2$-C$_{10}$-alkinyl, C$_3$-C$_{10}$-cycloalkyl, C$_3$-C$_{12}$-aryl or C$_3$-C$_{18}$-heteroaryl that is optionally substituted in one or more places in the same way or differently with hydroxy, halogen, C$_1$-C$_{12}$-alkoxy, C$_1$-C$_6$-alkylthio, amino, cyano, C$_1$-C$_6$-alkyl, —NH—(CH$_2$)$_p$—C$_3$-C$_{10}$-cycloalkyl, C$_3$-C$_{10}$-cycloalkyl, C$_1$-C$_6$-hydroxyalkyl, C$_2$-C$_6$-alkenyl, C$_2$-C$_6$-alkinyl, C$_1$-C$_6$-alkoxy-C$_1$-C$_6$-alkyl, C$_1$-C$_6$-alkoxy-C$_1$-C$_6$-alkoxy-C$_1$-C$_6$-alkyl, —NHC$_1$-C$_6$-alkyl, —N(C$_1$-C$_6$-alkyl)$_2$, —SO(C$_1$-C$_6$-alkyl), —SO$_2$(C$_1$-C$_6$-alkyl), C$_1$-C$_6$-alkanoyl, —CONR$^8$R$^9$, —COR$^{10}$, C$_1$-C$_6$-alkylOAc, carboxy, C$_3$-C$_{12}$-aryl, C$_3$-C$_8$-heteroaryl, —(CH$_2$)$_p$—C$_3$-C$_{12}$-aryl, —(CH$_2$)$_p$—C$_3$-C$_{18}$-heteroaryl, phenyl-(CH$_2$)$_p$—R$^{10}$, —(CH$_2$)$_p$PO$_3$(R$^{10}$)$_2$ or with the group —NR$^8$R$^9$, and the phenyl, C$_3$-C$_{10}$-cycloalkyl, C$_3$-C$_{12}$-aryl, C$_3$-C$_{18}$-heteroaryl, —(CH$_2$)$_p$—C$_3$-C$_{12}$-aryl and —(CH$_2$)$_p$—C$_3$-C$_{18}$-heteroaryl itself optionally can be substituted in one or more places in the same way or differently with halogen, hydroxy, C$_1$-C$_6$-alkyl, C$_1$-C$_6$-alkoxy, or with the group —CF$_3$ or —OCF$_3$, and the ring of the C$_3$-C$_{10}$-cycloalkyl and the C$_1$-C$_{10}$-alkyl optionally can be interrupted by one or more nitrogen, oxygen and/or sulfur atoms, and/or can be interrupted by one or more =C=O groups in the ring and/or optionally one or more possible double bonds can be contained in the ring, m stands for 0 to 8, and n and p stand for 0 to 6, as well as isomers, diastereomers, enantiomers and salts thereof, overcome the known drawbacks.

In particular selected therefrom are compounds of general formula (I), in which

A stands for phenylene or thiophenylene,

B stands for C$_1$-C$_{12}$-alkylene that is optionally substituted in one or more places in the same way or differently with hydroxy, C$_1$-C$_6$-alkyl or C$_1$-C$_6$-hydroxyalkyl, X and Y, in each case independently of one another, stand for oxygen or for the group =NR$^{11}$, —NR$^8$CO—, —CONR$^8$—, —SO$_2$NR$^8$— or —NR$^8$SO$_2$—, R$^1$ and R$^5$, in each case independently of one another, stand for hydrogen or for the group —SO$_2$NR$^8$R$^9$, R$^2$ stands for hydrogen, $R^3$ stands for hydrogen, halogen, cyano, $C_1$-$C_{10}$-alkyl or for the group —$CONR^8R^9$, $R^4$ stands for hydrogen, $R^8$ and $R^{11}$ stand for hydrogen, $R^9$ stands for hydrogen or $C_1$-$C_6$-alkyl, m stands for 0 to 8, and n stands for 0 to 6, as well as isomers, diastereomers, enantiomers and salts thereof.

If the production of the compounds of general formula I according to the invention is not described, the latter is carried out analogously to known methods.

The structural determination of the macrocyclic fragrances Muskon and Zibeton by Ruzicka ((a) Ruzicka, L. Helv. Chim. Acta 1926, 9, 715. (b) Ruzicka, L. Helv. Chim. Acta 1926, 9, 249) in 1926 marks the beginning of the chemistry of macrocyclic compounds.

In general, medium (8- to 11-membered) and large ($\geqq$12-membered) rings are referred to as macrocyclic compounds. The established processes for synthesis of macrocyclic compounds are partially based on ring enlargement reactions (Hesse, M. Ring Enlargement in Organic Chemistry, VCH, Weinheim, 1991), and more rarely on ring contractions (Hayashi, T. J. Org. Chem. 1984, 49, 2326).

The most frequently used method is the cyclization of bifunctional acyclic precursors (Reviews zur Synthese von Macrocyclen [Reviews on the Synthesis of Macrocyclic Compounds]: (a) Roxburgh, C. J. Tetrahedron 1995, 51, 9767. (b) Meng, Q. Top. Curr. Chem. 1991, 161, 107. (c) Paterson, I. Tetrahedron 1985, 41, 3569. (d) Masamune, S. Angew. Chem. [Applied Chemistry] 1977, 89, 602. (e) Nicolaou, K. C. Tetrahedron 1977, 33, 683; (f) Ruggli, P. Liebigs Ann. Chem. 1912, 92).

The production of the compounds of general formula I according to the invention can be carried out quickly and with very good yields by the ring closure via the 2-position of the pyrimidine of acyclic precursors of Formula (VIII) or (IX), by a) compounds of general formula VIII

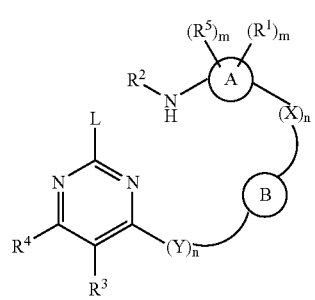

(VIII)

in which $R^1$, $R^2$, $R^3$, $R^4$, $R^5$, X, Y, A, B, m and n have the meanings that are indicated in general formula I, and L stands for a leaving group, being cyclized with a suitable acid to compounds of general formula I, or b) the acyclic precursors of general formula (IX)

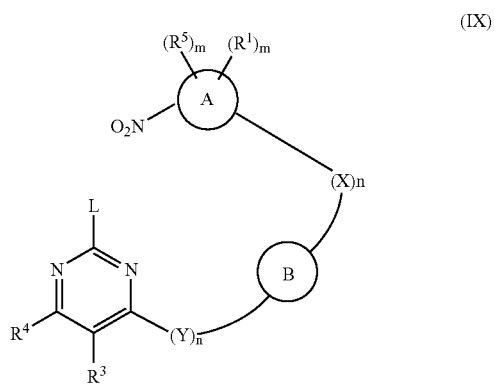

(IX)

in which $R^1$, $R^3$, $R^4$, $R^5$, X, Y, A, B, m and n have the meanings that are indicated in general formula I, and L stands for a leaving group, first being reduced to amine form in a suitable solvent and a suitable reducing agent at 0° C. until reflux takes place and then the intermediately formed amine being cyclized to the compounds of general formula I.

The production of the compounds of general formula I according to the invention is also the subject of this invention.

Suitable solvents are, for example, simple ketones, such as acetone; alcohols, such as, e.g., ethanol or butanol; esters, such as, for example, ethyl acetate; aromatic solvents, such as, for example, toluene or benzene, as well as polar aprotic solvents, such as acetonitrile, DMSO, DMF or N-methylpyrrolidines or mixtures of these solvents, also with the addition of water.

Suitable reducing agents are, for example, Ti(III)Cl or Sn(II)Cl.

Leaving groups in the meaning of L are defined as, for example, a halo- or sulfonyloxy group, such as fluorine, chlorine, bromine, iodine, methanosulfonyloxy, toluene-4-sulfonyloxy, trifluoromethylsulfonyloxy, etc.

For cyclization, acids that are used are, for example, suitable Lewis acids, such as inorganic acids such as hydrogen chloride, hydrogen bromide, sulfuric acid; organic acids such as acetic acid, formic acid, $BBr_3$; metal salts such as Ti(III)Cl, Sn(II)Cl, Ln(III)Otf, etc.

The intermediate products of general formulas II, III, IV, V, VI and VII, preferably used for the production of the compounds of general formula I according to the invention

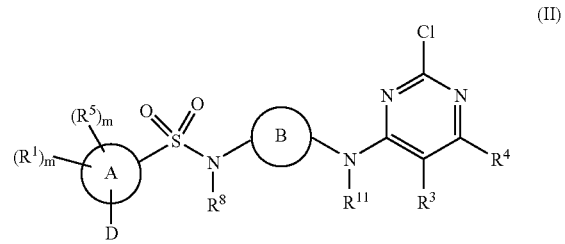

(II)

-continued

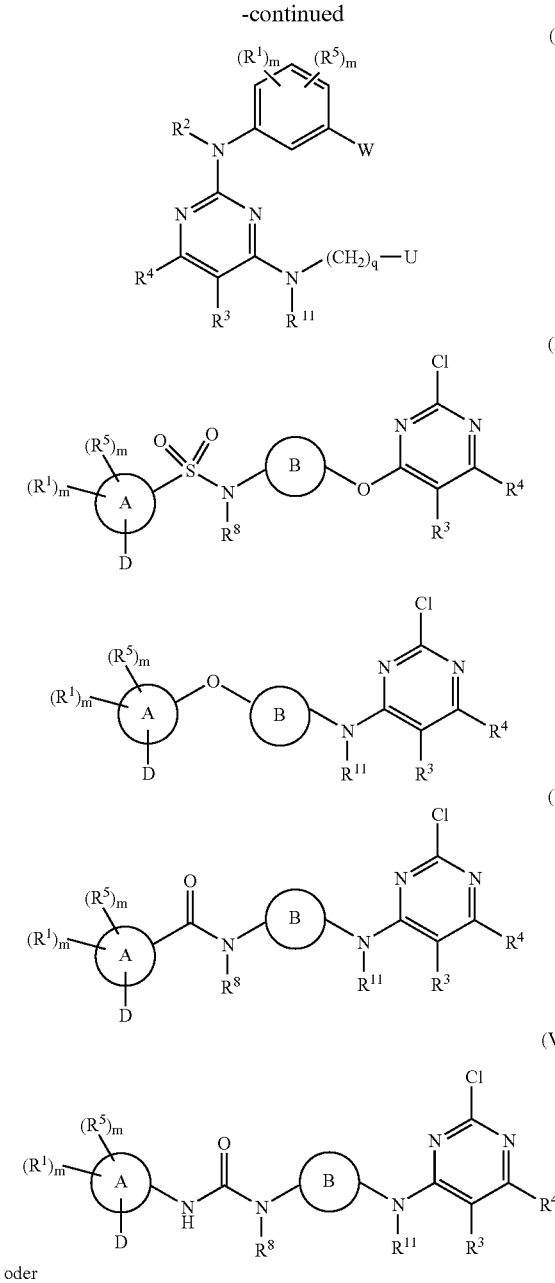

oder

[or]

in which $R^1$, $R^2$, $R^3$, $R^4$, $R^5$, $R^8$, $R^{11}$, A, B and m have the meanings that are indicated in general formula I and D stands for —$NH_2$, NAc or —$NO_2$, q stands for 1 to 12, U stands for group —OH, —$CO_2H$, —$CO_2$—$C_1$-$C_6$-alkyl, —$SO_2Cl$, —$SO_2F$, —$SO_3H$ or

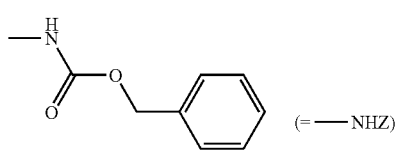

(= —NHZ)

and W stands for the group —OH —OH, —$CO_2H$, —$CO_2$—$C_1$-$C_6$-alkyl, —$SO_2Cl$, —$SO_2F$ or —$SO_3H$, as well as isomers, diastereomers, enantiomers and salts thereof, are also subjects of this invention.

In particular, preferably those intermediate products of general formulas II, III, IV, V, VI and VII are used, in which A stands for phenylene or thiophenylene, and
$R^1$, $R^2$, $R^3$, $R^4$, $R^5$, $R^8$, $R^{11}$ and m have the meanings that are indicated in general formula I, and D stands for —$NH_2$, —NAc or —$NO_2$, q stands for 1 to 12,
U stands for the group —OH, —$CO_2H$, —$CO_2$—$C_1$-$C_6$-alkyl, —$SO_2Cl$, —$SO_2F$, —$SO_3H$ or

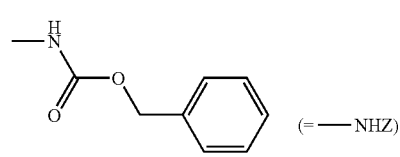

(= —NHZ)

and

W stands for the group —OH —OH, —$CO_2H$, —$CO_2$—$C_1$-$C_6$-alkyl, —$SO_2Cl$, —$SO_2F$ or —$SO_3H$, as well as isomers, diastereomers, enantiomers and salts thereof.

The compounds according to the invention can inhibit, on the one hand, cyclin-dependent kinases. The eukaryotic cell division cycle ensures the duplication of the genome and its distribution to the daughter cells by passing through a coordinated and regulated sequence of events. The cell cycle is divided into four successive phases: the G1 phase represents the time before the DNA replication in which the cell grows and is sensitive to outside stimuli. In the S phase, the cell replicates its DNA, and in the G2 phase, preparations are made for entry into mitosis. In mitosis (M phase), the replicated DNA separates, and cell division is complete.

Figure 1:
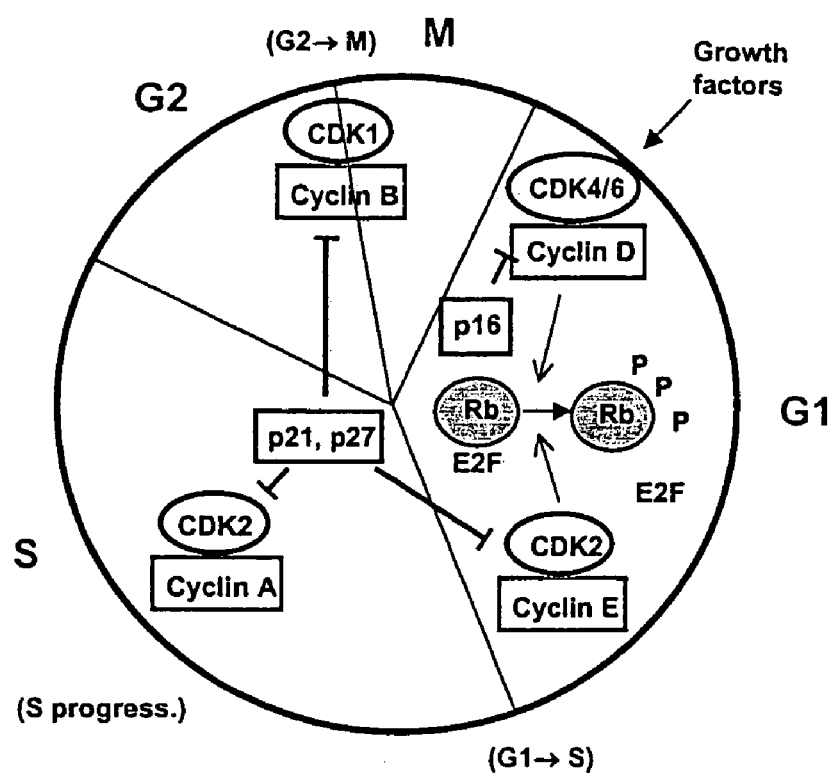
FIG. 1 schematically represents the cell cycle.

The cyclin-dependent kinases (CDKs), a family of serine/threonine kinases, whose members require the binding of a cyclin (Cyc) as a regulatory subunit in order for them to activate, drive the cell through the cell cycle. Different CDK/Cyc pairs are active in the various phases of the cell cycle. CDK/Cyc pairs that are important to the basic function of the cell cycle are, for example, CDK4(6)/CycD, CDK2/CycE, CDK2/CycA, CDK1/CycA and CDK1/CycB. Some members of the CDK enzyme family have a regulatory function by influencing the activity of the above-mentioned cell cycle CDKs, while no specific function could be associated with other members of the CDK enzyme family. One of the latter, CDK5, is distinguished in that it has an a typical regulatory subunit (p35) that deviates from the cyclins, and its activity is highest in the brain.

The entry into the cell cycle and the passage through the "restriction points," which marks the independence of a cell from further growth signals for the completion of the cell division that has begun, are controlled by the activity of the CDK4(6)/CycD and CDK2/CycE complexes. The essential substrate of these CDK complexes is the retinoblastoma protein (Rb), the product of the retinoblastoma tumor suppressor gene. Rb is a transcriptional co-repressor protein. In addition to other, still largely little understood mechanisms, Rb binds and inactivates Rb transcription factors of the E2F type and forms transcriptional repressor complexes with histone-deacetylases (HDAC) (Zhang, H. S. et al. (2000). Exit from G1 and S phase of the cell cycle is regulated by repressor complexes containing HDAC-Rb-hSWI/SNF and Rb-hSWI/SNF. *Cell* 101, 79-89). By the phosphorylation of Rb by CDKs, bonded E2F transcription factors are released and result in transcriptional activation of genes, whose products are required for the DNA synthesis and the progression through the S-phase. In addition, the Rb-phosphorylation brings about the breakdown of the Rb-HDAC complexes, by which additional genes are activated. The phosphorylation of Rb by CDK's is to be treated as equivalent to exceeding the "restriction points." For the progression through the S-phase and its completion, the activity of the CDK2/CycE and CDK2/CycA complexes is necessary, e.g., the activity of the transcription factors of the E2F type is turned off by means of phosphorylation by CDK2/CycA as soon as the cells are entered into the S-phase. After replication of DNA is complete, the CDK1 in the complex with CycA or CycB controls the entry into and the passage through phases G2 and M (FIG. 1).

According to the extraordinary importance of the cell-division cycle, the passage through the cycle is strictly regulated and controlled. The enzymes that are necessary for the progression through the cycle must be activated at the correct time and are also turned off again as soon as the corresponding phase is passed. Corresponding control points ("checkpoints") stop the progression through the cell cycle if DNA damage is detected, or the DNA replication or the creation of the spindle device is not yet completed.

The activity of the CDKs is controlled directly by various mechanisms, such as synthesis and degradation of cyclins, complexing of the CDKs with the corresponding cyclins, phosphorylation and dephosphorylation of regulatory threonine and tyrosine radicals, and the binding of natural inhibitory proteins. While the amount of protein of the CDKs in a proliferating cell is relatively constant, the amount of the individual cyclins oscillates with the passage through the cycle. Thus, for example, the expression of CycD during the early G1 phase is stimulated by growth factors, and the expression of CycE is induced after the "restriction points" are exceeded by the activation of the transcription factors of the E2F type. The cyclins themselves are degraded by the ubiquitin-mediated proteolysis. Activating and inactivating phosphorylations regulate the activities of the CDKs, for example phosphorylate CDK-activating kinases (CAKs) Thr160/161 of the CDK1, while, by contrast, the families of Wee1/Myt1 inactivate kinases CDK1 by phosphorylation of Thr14 and Tyr15. These inactivating phosphorylations can be destroyed in turn by cdc25 phosphatases. The regulation of the activity of the CDK/Cyc complexes by two families of natural CDK inhibitor proteins (CKIs), the protein products of the p21 gene family (p21, p27, p57) and the p16 gene family (p15, p16, p18, p19) is very significant. Members of the p21 family bind to cyclin complexes of CDKs 1,2,4,6, but inhibit only the complexes that contain CDK1 or CDK2. Members of the p16 family are specific inhibitors of the CDK4 and CDK6 complexes.

The plane of control point regulation lies above this complex direct regulation of the activity of the CDKs. Control points allow the cell to track the orderly sequence of the individual phases during the cell cycle. The most important control points lie at the transition from G1 to S and from G2 to M. The G1 control point ensures that the cell does not initiate any DNA synthesis unless it has proper nutrition, interacts correctly with other cells or the substrate, and its DNA is intact. The G2/M control point ensures the complete replication of DNA and the creation of the mitotic spindle before the cell enters into mitosis. The G1 control point is activated by the gene product of the p53 tumor suppressor gene. p53 is activated after detection of changes in metabolism or the genomic integrity of the cell and can trigger either a stopping of the cell cycle progression or apoptosis. In this case, the transcriptional activation of the expression of the CDK inhibitor protein p21 by p53 plays a decisive role. A second branch of the G1 control point comprises the activation of the ATM and Chk1 kinases after DNA damage by UV light or ionizing radiation and finally the phosphorylation and the subsequent proteolytic degradation of the cdc25A phosphatase (Mailand, N. et al. (2000). Rapid Destruction of Human cdc25A in Response to DNA Damage. *Science* 288, 1425-1429). A shutdown of the cell cycle results from this, since the inhibitory phosphorylation of the CDKs is not removed. After the G2/M control point is activated by damage of the DNA, both mechanisms are involved in a similar way in stopping the progression through the cell cycle.

The loss of the regulation of the cell cycle and the loss of function of the control points are characteristics of tumor cells. The CDK-Rb signal path is affected by mutations in over 90% of human tumor cells. These mutations, which finally result in inactivating phosphorylation of the RB, include the over-expression of D- and E-cyclins by gene amplification or chromosomal translocations, inactivating mutations or deletions of CDK inhibitors of the p16 type, as well as increased (p27) or reduced (CycD) protein degradation. The second group of genes, which are affected by mutations in tumor cells, codes for components of the control points. Thus p53, which is essential for the G1 and G2/M control points, is the most frequently mutated gene in human tumors (about 50%). In tumor cells that express p53 without mutation, it is often inactivated because of a greatly increased protein degradation. In a similar way, the genes of other proteins that are necessary for the function of the control points are affected by mutations, for example ATM (inactivating mutations) or cdc25 phosphatases (over-expression).

Convincing experimental data indicate that CDK2/Cyc complexes occupy a decisive position during the cell cycle progression: (1) Both dominant-negative forms of CDK2, such as the transcriptional repression of the CDK2 expression by anti-sense oligonucleotides, produce a stopping of the cell cycle progression. (2) The inactivation of the CycA gene in mice is lethal. (3) The disruption of the function of the CDK2/CycA complex in cells by means of cell-permeable peptides resulted in tumor cell-selective apoptosis (Chen, Y. N. P. et al. (1999). Selective Killing of Transformed Cells by Cyclin/Cyclin-Dependent Kinase 2 Antagonists. *Proc. Natl. Acad. Sci. USA* 96, 4325-4329).

Changes of the cell cycle control play a role not only in carcinoses. The cell cycle is activated by a number of viruses, both by transforming viruses as well as by non-transforming viruses, to make possible the reproduction of viruses in the host cell. The false entry into the cell cycle of normally post-mitotic cells is associated with various neurodegenerative diseases.

The mechanisms of the cell cycle regulation, their changes in diseases and a number of approaches to develop inhibitors of the cell cycle progression and especially the CDKs were already described in a detailed summary in several publications (Sielecki, T. M. et al. (2000). Cyclin-Dependent Kinase Inhibitors: Useful Targets in Cell Cycle Regulation. *J. Med. Chem.* 43, 1-18; Fry, D. W. & Garrett, M. D. (2000). Inhibitors of Cyclin-Dependent Kinases as Therapeutic Agents for the Treatment of Cancer. *Curr. Opin. Oncol. Endo. Metab. Invest. Drugs* 2, 40-59; Rosiania, G. R. & Chang, Y. T. (2000). Targeting Hyperproliferative Disorders with Cyclin-Dependent Kinase Inhibitors. *Exp. Opin. Ther. Patents* 10, 215-230; Meijer, L. et al. (1999). Properties and Potential Applications of Chemical Inhibitors of Cyclin-Dependent Kinases. *Pharmacol. Ther.* 82, 279-284; Senderowicz, A. M. & Sausville, E. A. (2000). Preclinical and Clinical Development of Cyclin-Dependent Kinase Modulators. *J. Natl. Cancer Inst.* 92, 376-387).

Compounds of general formula I according to the invention can also inhibit, i.a., receptor tyrosine kinases and their ligands, which specifically regulate the function of endothelial cells. Receptor tyrosine kinases and their ligands that specifically regulate the function of endothelial cells are involved in a decisive way in the physiological as well as the pathogenic angiogeneses. Of special importance here is the VEGF/VEGF receptor system. In pathological situations that accompany enhanced neovascularization, an increased expression of angiogenic growth factors and their receptors was found. Most solid tumors thus express large amounts of VEGF, and the expression of the VEGF receptors is preferably significantly increased in the endothelial cells, which are close to the tumors or pass through the latter (Plate et al., Cancer Res. 53, 5822-5827, 1993). The inactivation of the VEGF/VEGF receptor system by VEGF-neutralizing antibodies (Kim et al., Nature 362, 841-844, 1993), retroviral expression of dominant-negative VEGF-receptor variants (Millauer et al., Nature 367, 576-579, 1994), recombinant VEGF-neutralizing receptor variants (Goldman et al., Proc. Natl. Acad. Sci. USA 95, 8795-8800, 1998), or low-molecular inhibitors of the VEGF-receptor tyrosine kinase (Fong et al., Cancer Res. 59, 99-106, 1999; Wedge et al., Cancer Res. 60, 970-975, 2000; Wood et al., Cancer Res. 60, 2178-2189, 2000) resulted in a reduced tumor growth and a reduced tumor vascularization. The inhibition of the angiogenesis is thus a possible treatment method for tumor diseases.

Compounds according to the invention can consequently inhibit either cyclin-dependent kinases, such as CDK1, CDK2, CDK3, CDK4, CDK5, CDK6, CDK7, CDK8 and CDK9, as well as the glycogen-synthase-kinase (GSK-3β) and VEGF-receptor tyrosine kinases or cyclin-dependent kinases or VEGF-receptor tyrosine kinases. These actions contribute to the fact that the compounds according to the invention can be used in the treatment of cancer, angiofibroma, arthritis, eye diseases, autoimmune diseases, chemotherapy agent-induced alopecia and mucositis, Crohn's disease, endometriosis, fibrotic diseases, hemangioma, cardiovascular diseases, infectious diseases, nephrological diseases, chronic and acute neurodegenerative diseases, as well as injuries to nerve tissue, viral infections, for inhibiting reocclusion of vessels after balloon catheter treatment, in vascular prosthetics or after mechanical devices are used to keep vessels open, such as, e.g., stents, as immunosuppressive agents, for supporting scar-free healing, in the case of senile keratosis and contact dermatitis, whereby cancer is defined as solid tumors, tumor or metastasis growth, Kaposi's sarcoma, Hodgkin's disease, and leukemia;

arthritis is defined as rheumatoid arthritis;

eye diseases are defined as diabetic retinopathy, and neovascular glaucoma;

auto-immune diseases are defined as psoriasis, alopecia and multiple sclerosis;

fibrotic diseases are defined as cirrhosis of the liver, mesangial cell proliferative diseases, and arteriosclerosis;

infectious diseases are defined as diseases that are caused by unicellular parasites;

cardiovascular diseases are defined as stenoses, such as, e.g., stent-induced restenoses, arterioscleroses, and restenoses;

nephrological diseases are defined as glomerulonephritis, diabetic nephropathy, malignant nephrosclerosis, thrombic microangiopathic syndrome, transplant rejections and glomerulopathy;

chronic neurodegenerative diseases are defined as Huntington's disease, amyotrophic lateral sclerosis, Parkinson's disease, AIDS dementia and Alzheimer's disease;

acute neurodegenerative diseases are defined as ischemias of the brain and neurotraumas;

and viral infections are defined as cytomegalic infections, herpes, hepatitis B or C, and HIV diseases.

To use the compounds according to the invention as pharmaceutical agents, the latter are brought into the form of a pharmaceutical preparation, which in addition to the active ingredient for enteral or parenteral administration contains suitable pharmaceutical, organic or inorganic inert support media, such as, for example, water, gelatin, gum arabic, lactose, starch, magnesium stearate, talc, vegetable oils, polyalkylene glycols, etc. The pharmaceutical preparations can be present in solid form, for example as tablets, coated tablets, suppositories, capsules, or in liquid form, for example as solutions, suspensions, or emulsions. Moreover, they optionally contain adjuvants, such as preservatives, stabilizers, wetting agents or emulsifiers; salts for changing the osmotic pressure or buffers.

These pharmaceutical preparations are also subjects of this invention.

For parenteral administration, especially injection solutions or suspensions, especially aqueous solutions of active compounds in polyhydroxyethoxylated castor oil, are suitable.

As carrier systems, surface-active adjuvants such as salts of bile acids or animal or plant phospholipids, but also mixtures thereof as well as liposomes or their components, can also be used.

For oral administration, especially tablets, coated tablets or capsules with talc and/or hydrocarbon vehicles or binders, such as, for example, lactose, corn or potato starch, are suitable. The administration can also be carried out in liquid form, such as, for example, as a juice, to which optionally a sweetener is added.

Enteral, parenteral and oral administrations are also subjects of this invention.

The dosage of the active ingredients can vary depending on the method of administration, age and weight of the patient, type and severity of the disease to be treated and similar factors. The daily dose is 0.5-1000 mg, preferably 50-200 mg, whereby the dose can be given as a single dose to be administered once or divided into two or more daily doses.

Subjects of this invention are also the use of compounds of general formula I for the production of a pharmaceutical agent for treating cancer, eye diseases, auto-immune diseases, arthritis, endometriosis, fibrotic diseases, cardiovascular diseases, chemotherapy agent-induced alopecia and mucositis, infectious diseases, nephrological diseases, chronic and acute neurodegenerative diseases, as well as injuries to nerve tissue, viral infections, hemangioma, angiofibroma, Crohn's disease, for inhibiting the reocclusion of vessels after balloon catheter treatment, e.g., in the case of vascular prosthetics or after mechanical devices are used to keep vessels open, such as, e.g., stents, as immunosuppressive agents, for supporting scar-free healing, in the case of senile keratosis and contact dermatitis, whereby cancer is defined as solid tumors, tumor or metastasis growth, Kaposi's sarcoma, Hodgkin's disease, and leukemia;

auto-immune diseases are defined as psoriasis, alopecia and multiple sclerosis;

cardiovascular diseases are defined as stenoses, such as, e.g., stent-induced restenoses, arterioscleroses and restenoses;

infectious diseases are defined as diseases that are caused by unicellular parasites;

nephrological diseases are defined as glomerulonephritis, diabetic nephropathy, malignant nephrosclerosis, thrombic microangiopathic syndrome, transplant rejections and glomerulopathy;

chronic neurodegenerative diseases are defined as Huntington's disease, amyotrophic lateral sclerosis, Parkinson's disease, AIDS dementia and Alzheimer's disease;

acute neurodegenerative diseases are defined as ischemias of the brain and neurotraumas;

arthritis is defined as rheumatoid arthritis, eye diseases are defined as diabetic retinopathy, and neovascular glaucoma;

fibrotic diseases are defined as cirrhosis of the liver, mesangial cell proliferative diseases, and art erioscrerosis;

and viral infections are defined as cytomegalic infections, herpes, hepatitis B or C, and HIV diseases.

Subjects of this invention also include pharmaceutical agents for treating the above-cited diseases, which contain at least one compound according to general formula I, as well as pharmaceutical agents with suitable formulation substances and vehicles.

The compounds of general formula I according to the invention are either excellent inhibitors of the cyclin-dependent kinases, such as CDK1, CDK2, CDK3, CDK4, CDK5, CDK6, CDK7, CDK8 and CDK9, as well as the glycogen-synthase-kinase (GSK-3β), and the VEGF-receptor tyrosine kinases or inhibitors of cyclin-dependent kinases or good inhibitors of VEGF-receptor tyrosine kinases.

If the production of the starting compounds is not described, the latter are known or can be produced analogously to known compounds or to processes that are described here. It is also possible to perform all reactions that are described here in parallel reactors or by means of combinatory operating procedures. The isomer mixtures can be separated into the enantiomers or E/Z isomers according to commonly used methods, such as, for example, crystallization, chromatography or salt formation.

The production of the salts is carried out in the usual way by a solution of the compound of formula I being mixed with the equivalent amount of or excess base or acid, which optionally is in solution, and the precipitate being separated or the solution being worked up in the usual way.

Production of the Compounds According to the Invention

The following examples explain the production of the compounds according to the invention, without the scope of the claimed compounds being limited to these examples.

In addition to the single-pot process already described above according to the invention, the compounds of general formula I according to the invention can also be produced according to the following general process variants:

Production of 5-Bromine Derivatives

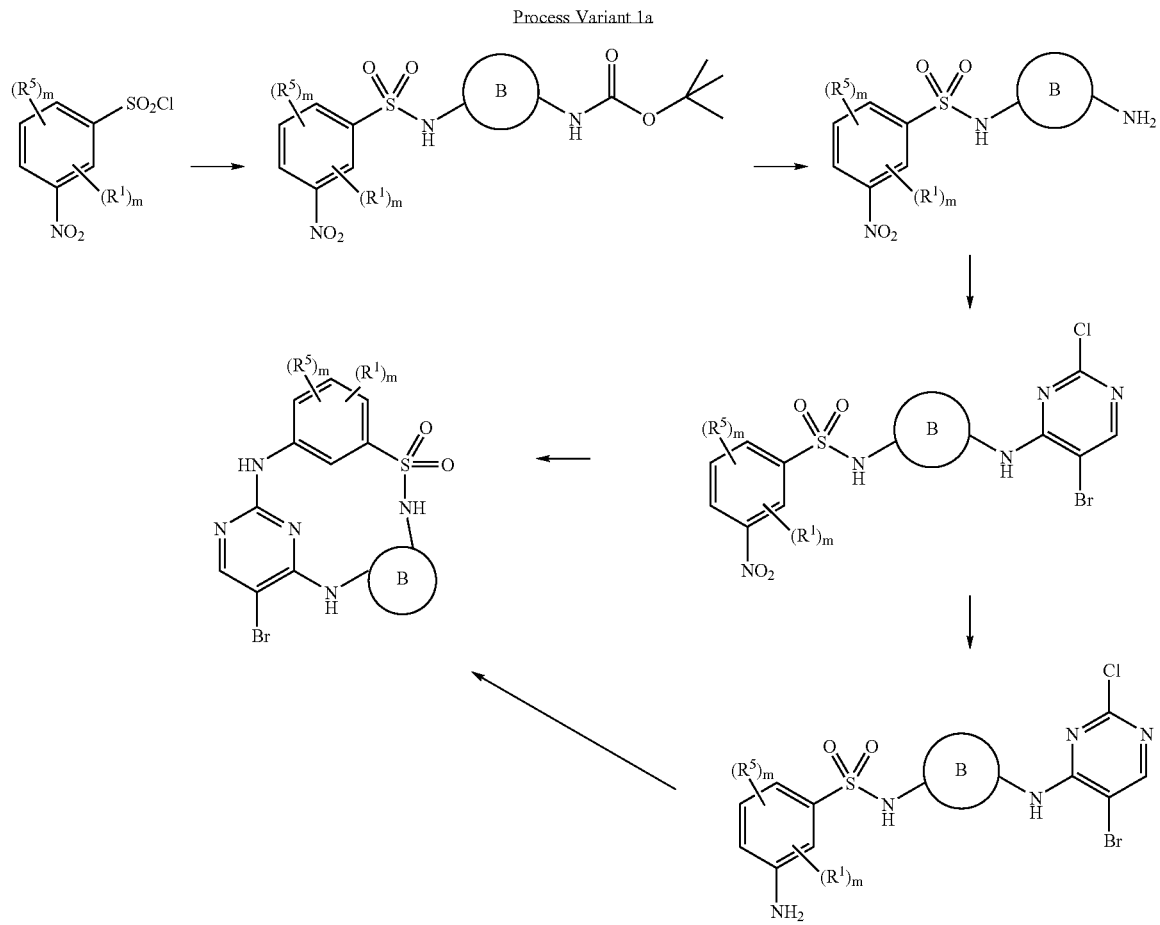

Process Variant 1a

In the general formulas, $R^1$, $R^5$, B and m have the meaning that is indicated under general formula I.

EXAMPLE 1.0

Production of $1^5$-Bromo-4-thia-2,5,11-triaza-1(2,4)-pyrimidina-3(1,3)-benzenacycloundecaphane 4,4-dioxides

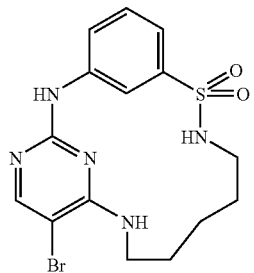

A solution of 100 mg (0.22 mmol) of 3-amino-N-[5-(5-bromo-2-chloro-pyrimidin-4-ylamino)-pentyl]-benzenesulfonamide in acetonitrile/water/2-butanol (8.5 ml/1.5 ml/0.5 ml) is added via a spray pump within 2 hours to a refluxing solution of acetonitrile/water/4 molar solution of hydrochloric acid in dioxane (45 ml/5 ml/0.6 ml). After another 60 minutes, the acetonitrile is drawn off in a rotary evaporator, and the residue is mixed with water (30 ml). It is extracted with ethyl acetate (3×). The combined organic phases are washed with 1 M NaHCO$_3$ solution, 10% citric acid, and 1 M NaHCO$_3$ solution, dried (Na$_2$SO$_4$), filtered and concentrated by evaporation. 83 mg (0.20 mmol, corresponding to 90% of theory) of the product is obtained.

$^1$H-NMR (DMSO): 9.65 (s, 1H), 8.78 (s, 1H), 8.03 (s, 1H), 7.43 (m, 2H), 7.30 (m, 2H), 7.22 (t, 1H), 3.42 (m, 2H), 2.75 (m, 2H), 1.65 (m, 2H), 1.42 (m, 4H). $^{13}$C-NMR (DMSO): 158.5s, 158.3s, 156.1d, 140.9s, 139.7s, 130.0d, 122.7d, 118.8d, 117.9d, 93.1s, 66.7t, 41.0t, 27.0t, 26.1t, 22.8t. MS: 412 (ES).

Production of Intermediate Products According to Process Variant 1a

1a) Production of [5-(3-Nitro-benzenesulfonylamino)-pentyl]-carbamic acid-tert-butyl ester

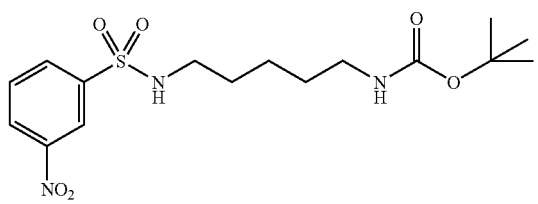

4.2 ml (30.1 mmol) of triethylamine is added to a solution of 3.21 g (14.5 mmol) of 3-nitrobenzenesulfonyl chloride and 3.0 ml (14.4 mmol) of N-Boc-1,5-diaminopentane in 50 ml of acetone and 15 ml of water. The reaction mixture is stirred for one hour at room temperature. Then, the acetone is drawn off in a rotary evaporator. After water (20 ml) is added, it is extracted with ethyl acetate (2×). The combined organic phases are dried (Na$_2$SO$_4$), filtered and concentrated by evaporation. 5.00 g (12.9 mmol, corresponding to 90% of theory) of the product is obtained as a light yellow oil.

$^1$H-NMR (DMSO): 8.49 (m, 2H), 8.19 (dd, 1H), 7.88 (m, 2H), 6.72 (t, 1H), 2.82 (m, 4H), 1.32 (m, 15H).

1b) Production of N-(5-Amino-pentyl)-3-nitro-benzenesulfonamide

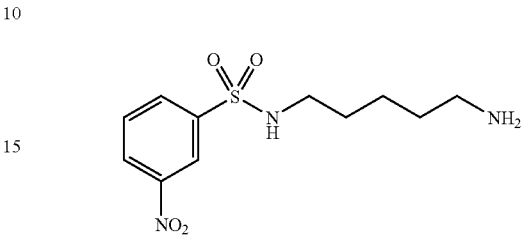

5.00 g (12.9 mmol) of [5-(3-nitro-benzenesulfonylamino)-pentyl]-carbamic acid-tert-butyl ester is mixed with 15 ml of trifluoroacetic acid and stirred for 90 minutes at room temperature. The reaction mixture is concentrated by evaporation, and the residue is made basic with saturated NaHCO$_3$ solution. Then, it is extracted with ethyl acetate (2×). The combined organic phases are washed with saturated NaCl solution, dried (Na$_2$SO$_4$), filtered and concentrated by evaporation. 3.4 g (11.8 mmol, corresponding to 91% of theory) of the product is obtained.

$^1$H-NMR (DMSO): 8.49 (m, 2H), 8.19 (dd, 1H), 7.90 (t, 1H), 7.60 (br, 3H), 2.73 (m, 4H), 1.35 (m, 6H).

1c) Production of N-[5-(5-Bromo-2-chloro-pyrimidin-4-ylamino)-pentyl]-3-nitro-benzenesulfonamide

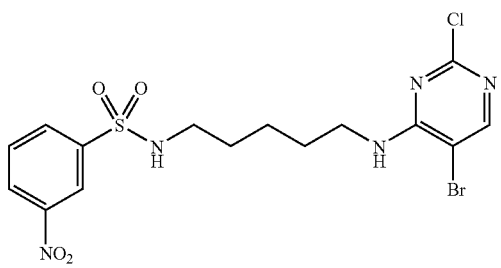

A solution of 1.2 g (5.3 mmol) of 5-bromo-2,4-dichloro-pyrimidine in 30 ml of acetonitrile is added to a solution of 1.5 g (5.2 mmol) of N-(5-amino-pentyl)-3-nitro-benzenesulfonamide in 50 ml of acetonitrile. The reaction mixture is mixed with 1.0 ml (7.2 mmol) of triethylamine and stirred for 17 hours at room temperature. After water (50 ml) is added, it is extracted (2×) with ethyl acetate. The combined organic phases are dried (Na$_2$SO$_4$), filtered and concentrated by evaporation. The remaining residue is purified by chromatography (hexane/ethyl acetate 2:1, Flashmaster II). 1.5 g (3.1 mmol, corresponding to 60% of theory) of the product is obtained.

$^1$H-NMR (DMSO): 8.49 (m, 2H), 8.19 (m, 2H), 7.88 (m, 2H), 7.68 (t, 1H), 3.30 (m, 2H), 2.79 (m, 2H), 1.45 (m, 4H), 1.21 (m, 2H). MS: 478 (ES).

1d) Production of 3-Amino-N-[5-(5-bromo-2-chloro-pyrimidin-4-ylamino)-pentyl]-benzenesulfonamide

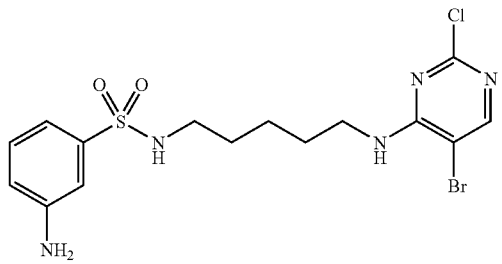

A solution of 300 mg (0.63 mmol) of N-[5-(5-bromo-2-chloro-pyrimidin-4-ylamino)-pentyl]-3-nitro-benzenesulfonamide in 6 ml of ethanol is mixed with 600 mg of tin(II) chloride and stirred for 30 minutes at 70° C. After cooling, the reaction mixture is carefully added to ice water and made basic with saturated NaHCO$_3$ solution. It is extracted with ethyl acetate (3×). The combined organic phases are dried (Na$_2$SO$_4$), filtered, and concentrated by evaporation. The remaining residue is purified by chromatography (ethyl acetate/hexane 4:1). 112 mg (0.25 mmol, corresponding to 40% of theory) of the product is obtained.

$^1$H-NMR (DMSO): 8.20 (s, 1H), 7.70 (br, 1H), 7.31 (br, 1H), 7.15 (t, 1H), 6.94 (m, 1H), 6.85 (m, 1H), 6.71 (m, 1H), 5.52 (s, 2H), 3.30 (m, 2H), 2.71 (m, 2H), 1.45 (m, 4H), 1.21 (m, 2H). MS: 448 (ES).

EXAMPLE 1.1

Production of 1$^5$-Bromo-4-thia-2,5,9-triaza-1(2,4)-pyrimidina-3(1,3)-benzenacyclononaphane-4,4-dioxide

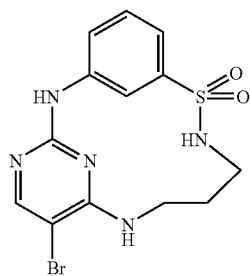

Method A

A solution of 200 mg (0.48 mmol) of 3-amino-N-[3-(5-bromo-2-chloro-pyrimidin-4-ylamino)-propyl]-benzenesulfonamide in acetonitrile/water/2-butanol (9.0 ml/1.0 ml/0.3 ml) is added via a spray pump within 2.5 hours to a refluxing solution of acetonitrile/water/4 molar solution of hydrochloric acid in dioxane (45 ml/5 ml/0.6 ml). After another 3 hours under reflux, the oil bath is turned off, and the reaction solution is stirred overnight at room temperature. The precipitate that is formed is filtered off, washed with water and then dried in a vacuum. 112 mg (0.31 mmol) of the product is obtained. The filtrate is concentrated by evaporation in a rotary evaporator. The precipitate that is formed is washed with water and filtered off. After drying, another 45 mg (0.12 mmol) of the product is obtained. The total yield of product is thus 157 mg (0.41 mmol, corresponding to 85% of theory).

Method B

A solution of 450 mg (1.00 mmol) of N-[3-(5-bromo-2-chloro-pyrimidin-4-ylamino)-propyl]-3-nitro-benzenesulfonamide in 9.5 ml of ethanol is mixed with 960 mg of tin(II) chloride and stirred for 30 minutes at 70° C. After cooling, the reaction mixture is carefully added to ice water and made basic with 1N NaOH solution. It is extracted with ethyl acetate (3×). The combined organic phases are dried (Na$_2$SO$_4$), filtered and concentrated by evaporation. The remaining residue is purified by chromatography (ethyl acetate/hexane 4:1). 72 mg of the crude product is obtained. It is mixed with 1N HCl and extracted with ethyl acetate. A colorless solid precipitates from the aqueous phase. The solid is filtered off and dried. 20 mg (0.05 mmol, corresponding to 5% of theory) of the product is obtained.

$^1$H-NMR (DMSO): 10.45 (s, 1H), 9.07 (s, 1H), 8.35 (br, 1H), 8.18 (s, 1H), 7.78 (t, 1H), 7.45 (m, 2H), 7.32 (m, 1H), 3.44 (m, 2H), 3.28 (m, 2H), 1.82 (m, 2H). MS: 384 (ES).

Production of the Intermediate Product According to Process Variant 1a

1e) Production of 3-Amino-N-[3-(5-bromo-2-chloro-pyrimidin-4-ylamino)-propyl]-benzenesulfonamide

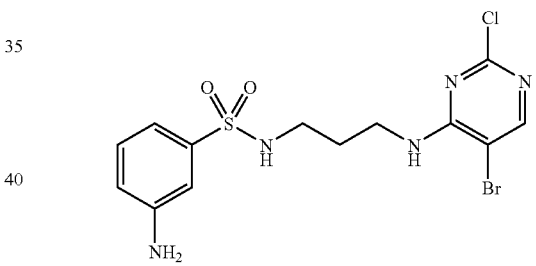

A solution of 1.35 g (2.99 mmol) of N-[3-(5-bromo-2-chloro-pyrimidin-4-ylamino)-propyl]-3-nitro-benzenesulfonamide in 100 ml of tetrahydrofuran is mixed under argon at room temperature with 15 ml of a 15% solution of Ti(III)Cl in about 10% hydrochloric acid. After 17 hours, the reaction solution is mixed again with 1 ml of the Ti(III)Cl solution and stirred for another 3 hours. The batch is made basic with 1N NaOH solution and then filtered. The filter cake is rewashed 2× with 100 ml of ethyl acetate/MeOH (30 ml/20 ml) in each case. The filtrate is concentrated by evaporation in a rotary evaporator and then extracted with ethyl acetate (2×). The combined organic phases are washed with NaCl solution, dried (Na$_2$SO$_4$), filtered and concentrated by evaporation. The remaining residue is purified by chromatography (dichloromethane/MeOH 95:5, Flashmaster II). 624 mg (1.48 mmol, corresponding to 49% of theory) of the product is obtained.

$^1$H-NMR (DMSO): 8.21 (s, 1H), 7.63 (t, 1H), 7.38 (t, 1H), 7.13 (t, 1H), 6.97 (m, 1H), 6.83 (m, 1H), 6.71 (m, 1H), 5.53 (s, 2H), 3.30 (m, 2H), 2.75 (m, 2H), 1.65 (m, 2H).

EXAMPLE 1.2

Production of rac-1⁵-Bromo-4-thia-2,5,9-triaza-1(2,4)-pyrimidina-3(1,3)-benzenacyclononaphan-7-ol-4,4-dioxide

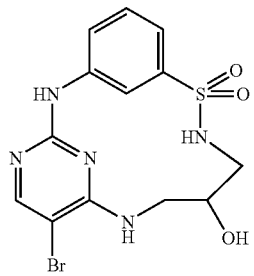

A solution of 150 mg (0.34 mmol) of 3-amino-N-[3-(5-bromo-2-chloro-pyrimidin-4-ylamino)-2-hydroxy-propyl]-benzenesulfonamide in acetonitrile/water (9.0 ml/1.0 ml) is added via a spray pump within 2.5 hours to a refluxing solution of acetonitrile/water/4 molar solution of hydrochloric acid in dioxane (45 ml/5 ml/0.6 ml). After another 4 hours under reflux, the oil bath is turned off, and the reaction solution is stirred overnight at room temperature. The precipitate that is formed is filtered off, washed with MeCN, and then dried in a vacuum. 125 mg (0.31 mmol, corresponding to 91% of theory) of the product is obtained.

¹H-NMR (DMSO): 10.65 (br, 1H), 9.03 (s, 1H), 8.41 (br, 1H), 8.22 (s, 1H), 7.93 (m, 1H), 7.46 (m, 2H), 7.34 (m, 1H), 4.14 (m, 1H), 3.94 (dd, 1H), 3.49 (m, 1H), 2.88 (m, 2H). MS: 402 (ES).

Production of Intermediate Products According to Process Variant 1a 1f)    3-Amino-N-[3-(5-bromo-2-chloro-pyrimidin-4-ylamino)-2-hydroxy-propyl]-benzenesulfonamide

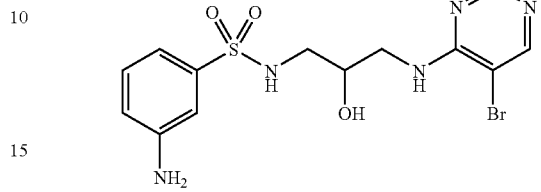

A solution of 258 mg (0.553 mmol) of N-[3-(5-bromo-2-chloro-pyrimidin-4-ylamino)-2-hydroxy-propyl]-3-nitro-benzenesulfonamide in 20 ml of tetrahydrofuran is mixed under argon at room temperature with 2.6 ml of a 15% solution of Ti(III)Cl in approximately 10% hydrochloric acid. After 2 hours, the reaction solution is mixed again with 0.2 ml of Ti(III)Cl solution and stirred for another 60 minutes. The batch is made basic with 1 M NaOH solution and then filtered. The filter cake is rewashed 2× with 50 ml of ethyl acetate/MeOH (30 ml/20 ml) in each case. The filtrate is concentrated by evaporation in a rotary evaporator and then extracted with ethyl acetate (2×). The combined organic phases are washed with NaCl solution, dried (Na₂SO₄), filtered and concentrated by evaporation. The remaining residue is purified by chromatography (dichloromethane/MeOH 95:5, Flashmaster II). 155 mg (0.36 mmol, corresponding to 64% of theory) of the product is obtained.

¹H-NMR (DMSO): 8.25 (s, 1H), 7.43 (t, 1H), 7.36 (t, 1H), 7.13 (t, 1H), 6.96 (m, 1H), 6.86 (m, 1H), 6.71 (m, 1H), 5.53 (s, 2H), 5.14 (d, 1H), 3.70 (m, 1H), 3.30 (m, 2H), 2.72 (m, 2H).

Production of Intermediate Products According to Process Variant 1b

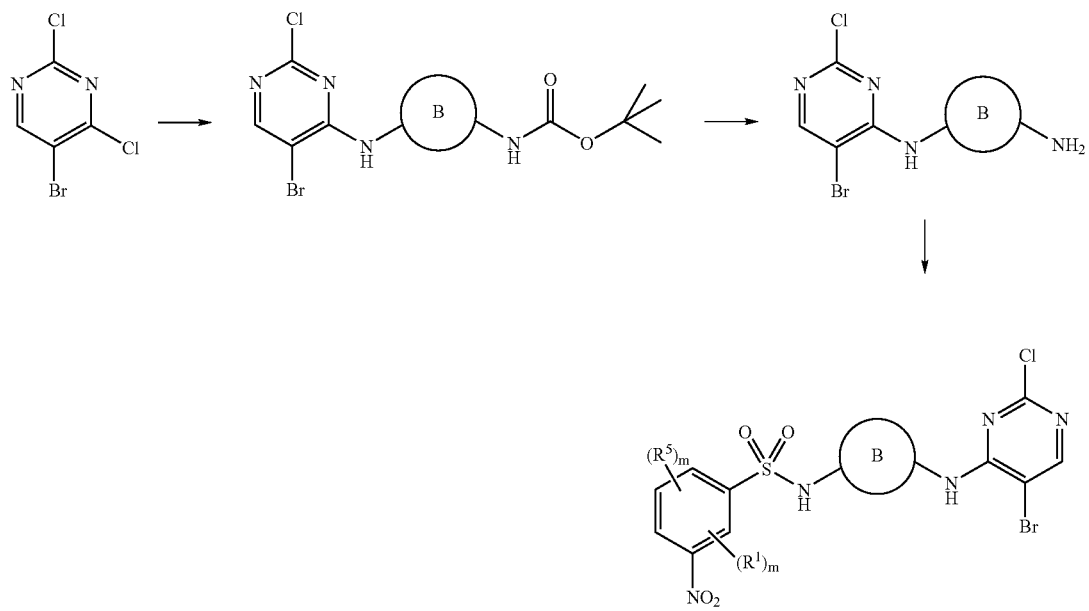

In the general formulas, $R^1$, $R^5$, B and m have the meaning that is indicated under general formula I.

1g) Production of [3-(5-Bromo-2-chloro-pyrimidin-4-ylamino)-propyl]-carbamic acid-tert-butyl-ester

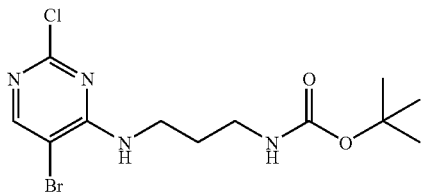

A solution of 6.1 g (26.6 mmol) of 5-bromo-2,4-dichloro-pyrimidine in 100 ml of acetonitrile is mixed successively with 5.0 g (28.7 mmol) of N-boc-1,3-diaminopropane and 4.5 ml (32.4 mmol) of triethylamine and stirred for 3.5 hours at room temperature. The batch is diluted with 200 ml of ethyl acetate. It is washed with saturated NaCl solution, citric acid (10%), saturated NaHCO₃ solution as well as saturated NaCl solution. The combined organic phases are dried (Na₂SO₄), filtered and concentrated by evaporation. 9.7 g (26.6 mmol, corresponding to 100% of theory) of the product is obtained.

$^1$H-NMR (DMSO): 8.22 (s, 1H), 7.63 (t, 1H), 6.79 (t, 1H), 3.30 (m, 2H), 2.94 (m, 2H), 1.63 (m, 2H), 1.35 (s, 9H).

1h) Production of N-(5-Bromo-2-chloro-pyrimidin-4-yl)-propane-1,3-diamine Hydrochloride

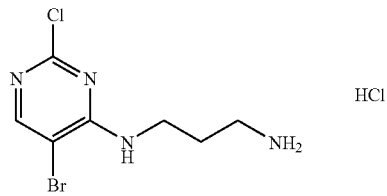

A solution of 5.0 g (13.7 mmol) of [3-(5-bromo-2-chloro-pyrimidin-4-ylamino)-propyl]-carbamic acid-tert-butyl-ester in 150 ml of acetonitrile is mixed with 25 ml of a 4 molar solution of hydrochloric acid in dioxane and stirred at room temperature. After 4 hours, the solvent is drawn off in a rotary evaporator, and the residue is dried in a drying oven. 4.1 g (13.7 mmol, corresponding to 100% of theory) of the product is obtained.

$^1$H-NMR (DMSO): 8.26 (s, 1H), 7.95 (m, 5H), 3.42 (m, 2H), 2.79 (m, 2H), 1.96 (m, 2H). MS: 265 (ES).

1i) Production of N-[3-(5-Bromo-2-chloro-pyrimidin-4-ylamino)-propyl]-3-nitro-benzenesulfonamide

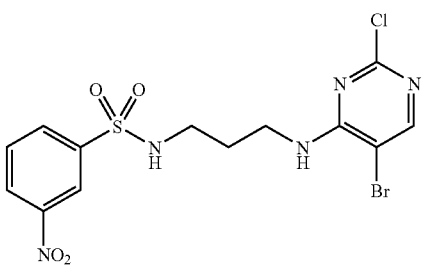

A solution of 530 mg (1.76 mmol) of N-(5-bromo-2-chloro-pyrimidin-4-yl)-propane-1,3-diamine hydrochloride and 352 mg (1.60 mmol) of 3-nitrobenzenesulfonyl chloride in 20 ml of acetone/6 ml of water is mixed at room temperature with 1 ml of triethylamine. After 2.5 hours, the organic solvent is drawn off in a rotary evaporator. After water (20 ml) is added, it is extracted with ethyl acetate. The combined organic phases are washed with citric acid (10%), saturated NaHCO₃ solution as well as saturated NaCl solution, dried (Na₂SO₄), filtered and concentrated by evaporation. 633 mg (1.41 mmol, corresponding to 87% of theory) of the product is obtained.

$^1$H-NMR (DMSO): 8.48 (m, 2H), 8.19 (m, 2H), 8.00 (t, 1H), 7.88 (t, 1H), 7.63 (t, 1H), 3.30 (m, 2H), 2.88 (t, 2H), 1.67 (m, 2H).

EXAMPLE 1.3

Production of rac-1$^5$-Bromo-4-thia-2,5,9-triaza-1(2,4)-pyrimidina-3(1,3)-benzenacyclonaphane-8-methanol-4,4-dioxide Hydrochloride

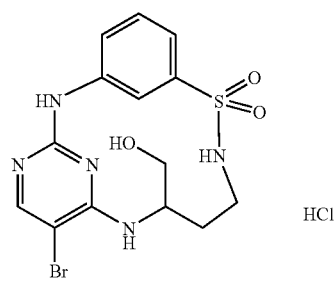

A solution of 145 mg (0.33 mmol) of 3-amino-N-[3-(5-bromo-2-chloro-pyrimidin-4-ylamino)-4-hydroxy-butyl]-benzenesulfonamide in acetonitrile/methanol/water (9.0 ml/2.0 ml/1.0 ml) is added via a spray pump within 3 hours to a refluxing solution of acetonitrile/water/4 molar solution of hydrochloric acid in dioxane (45 ml/5 ml/0.8 ml). After another 14 hours under reflux, about 20 ml of acetonitrile is drawn off in a rotary evaporator. After cooling, the precipitate that is formed is suctioned off, rewashed with water and diisopropyl ether, and dried. 97 mg (0.22 mmol, corresponding to 67% of theory) of the product is obtained in the form of hydrochloride.

$^1$H-NMR (DMSO): 10.22 (s, 1H), 8.99 (m, 1H), 8.19 (s, 1H), 7.69 (t, 1H), 7.40 (m, 3H), 6.95 (br, 1H), 4.04 (m, 1H), 3.70 (m, 2H), 3.40 (m, 2H), 2.19 (m, 1H), 1.61 (m, 1H). MS: 414 (ES).

The racemate is separated preoperatively into the enantiomers by means of chiral HPLC:

Column: Chiralpak AD (20 μm); 250×60 mm

Eluants: Hexane/ethanol 80/20+0.1% DEA

Flow: 100 ml/min

Detector: UV 280 nm

Temperature: Room temperature

Retention: Enantiomer (+): 38.5 min, 1.3 (+)-Enantiomer

Enantiomer (−): 59.1 min, 1.3 (−)-Enantiomer

EXAMPLE 1.4

Production of 1⁵-Bromo-4-thia-2,5,9-triaza-1(2,4)-pyrimidina-3(1,3)-benzenacyclononaphan-3⁵-amine-4,4-dioxides

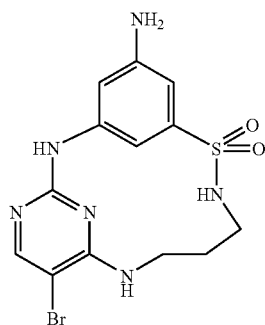

A solution of 46 mg (0.11 mmol) of 1⁵-bromo-3⁵-nitro-4-thia-2,5,9-triaza-1 (2,4)-pyrimidina-3(1,3)-benzenacyclononaphane-4,4-dioxide hydrochloride in 1 ml of THF is mixed at room temperature with 0.4 ml of a 15% solution of Ti(III)Cl in approximately 10% hydrochloric acid. After 67 hours, it is mixed again with 0.2 ml of a 15% solution of Ti(III)Cl in approximately 10% hydrochloric acid, and it is stirred for another 21 hours. The batch is made basic with 2N NaOH solution and extracted from ethyl acetate. The combined organic phases are washed with NaCl solution and then filtered through a Whatman filter and concentrated by evaporation. The residue that is formed is recrystallized from methanol/diisopropyl ether. 24 mg (0.06 mmol, corresponding to 55% of theory) of the product is obtained.

¹H-NMR (DMSO): 9.45 (br, 1H), 8.51 (br, 1H), 8.02 (br, 1H), 7.53 (br, 1H), 7.31 (br, 1H), 6.60 (br, 1H), 6.48 (br, 1H), 5.42 (s, 2H), 3.30 (m, 4H), 1.78 (m, 2H). MS: 399 (ES).

EXAMPLE 1.5

Production of 1⁵-Bromo-3⁵-nitro-4-thia-2,5,9-triaza-1(2,4)-pyrimidina-3(1,3)-benzenacyclononaphane-4,4-dioxide hydrochloride

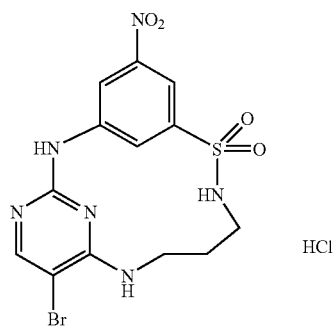

A solution of 420 mg (0.90 mmol) of 3-amino-N-[3-(5-bromo-2-chloro-pyrimidin-4-ylamino)-propyl]-5-nitro-benzenesulfonamide in acetonitrile/DMF (7.0 ml/3.0 ml) is added via a spray pump within 2 hours to a refluxing solution of acetonitrile/4 molar solution of hydrochloric acid in dioxane (150.0 ml/2.5 ml). After cooling, the precipitate that is formed is suctioned off. The filtrate is concentrated by evaporation, and the residue is digested with methanol. 151 mg (0.36 mmol, corresponding to 40% of theory) of the product is obtained in the form of hydrochloride.

¹H-NMR (DMSO): 10.68 (s, 1H), 9.51 (s, 1H), 8.15 (m, 4H), 8.02 (m, 1H), 3.41 (m, 4H), 1.83 (m, 2H). MS: 429 (ES).

Production of Intermediate Products According to Process Variant 1a

1j) Production of 3-Amino-N-[3-(5-bromo-2-chloro-pyrimidin-4-ylamino)-propyl]-5-nitro-benzenesulfonamide

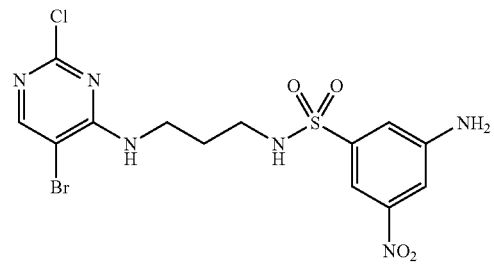

A solution of 602 mg (1.28 mmol) of N-[3-(5-bromo-2-chloro-pyrimidin-4-ylamino)-propyl]-3,5-dinitro-benzenesulfonamide in 10 ml of THF is mixed at room temperature with 4.2 ml of a 15% solution of Ti(III)Cl in approximately 10% hydrochloric acid. After 2 hours, it is mixed again with 3.0 ml of a 15% solution of Ti(III)Cl in approximately 10% hydrochloric acid, and it is stirred for another 16 hours. The batch is made basic with 2N NaOH solution and filtered. The filter cake is rewashed with THF and water. The THF of the filtrate is drawn off on a rotary evaporator, and the residue is extracted from ethyl acetate. The combined organic phases are filtered through a Whatman filter and concentrated by evaporation. 440 mg (0.95 mmol, corresponding to 74% of theory) of the product is obtained.

MS: 465 (ES).

Production of N-Alkyl Derivatives

Process Variant 2

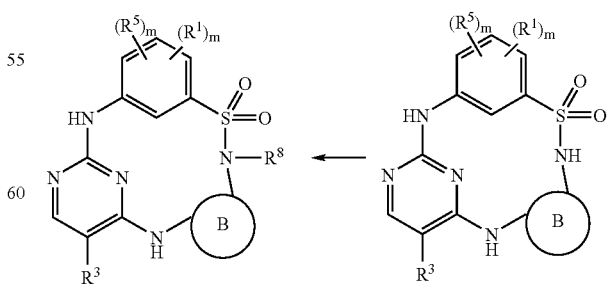

In the general formulas, $R^1$, $R^3$, $R^5$, $R^8$, B and m have the meaning that is indicated under general formula I.

EXAMPLE 2.0

Production of 1⁵-Bromo-5-methyl-4-thia-2,5,9-triaza-1(2,4)-pyrimidina-3(1,3)-benzenacyclononaphane-4,4-dioxide

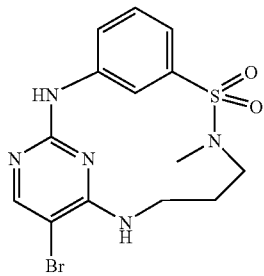

A solution of 35 mg (0.09 mmol) of $1^5$-bromo-4-thia-2,5,9-triaza-1(2,4)-pyrimidina-3(1,3)-benzenacyclononaphane-4,4-dioxide in 4 ml DMSO is mixed at room temperature with 6 mg (0.15 mmol) of a 60% dispersion of sodium hydride in mineral oil, and it is stirred for 10 minutes. Then, 7 µl of methyl iodide is added. After 4 hours, it is mixed again with 6 mg of a 60% dispersion of sodium hydride in mineral oil as well as 7 µl of methyl iodide, and it is stirred overnight. The batch is diluted with ethyl acetate and washed with saturated NaCl solution. The combined organic phases are dried (Na₂SO₄), filtered and concentrated by evaporation. The remaining residue is digested with MTB ether. 10 mg (0.03 mmol, corresponding to 27% of theory) of the product is obtained.

¹H-NMR (DMSO): 9.78 (s, 1H), 9.08 (m, 1H), 8.02 (s, 1H), 7.40 (m, 4H), 3.44 (m, 4H), 2.68 (s, 3H), 1.95 (m, 2H). MS: 398 (ES).

Production of 4-Oxo Derivatives

Process Variant 3a

In the general formulas, $R^1$, $R^3$, $R^5$, B and m have the meaning that is indicated under general formula I.

EXAMPLE 3.0

Production of 1⁵-Bromo-9-oxa-4-thia-2,5-diaza-1(2,4)-pyrimidina-3(1,3)-benzenacyclononaphane-4,4-dioxide

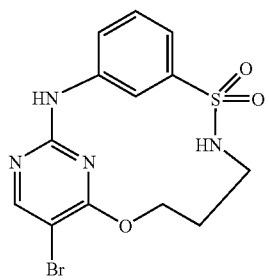

A solution of 30 mg (0.07 mmol) of 3-amino-N-[3-(5-bromo-2-chloro-pyrimidin-4-yloxy)-propyl]-benzenesulfonamide in acetonitrile/DMSO (9.5 ml/0.5 ml) is added via a spray pump within 2 hours to a refluxing solution of acetonitrile/water/4 molar solution of hydrochloric acid in dioxane (22.5 ml/2.5 ml/0.3 ml). After another 16 hours, the acetonitrile is drawn off in a rotary evaporator, and the residue is mixed with 1 M NaHCO₃ solution. It is extracted with ethyl acetate (2×). The combined organic phases are dried (Na₂SO₄), filtered and concentrated by evaporation. The residue that is obtained is purified by chromatography (DCM/EtOH 9:1). 8 mg (0.02 mmol, corresponding to 30% of theory) of the product is obtained.

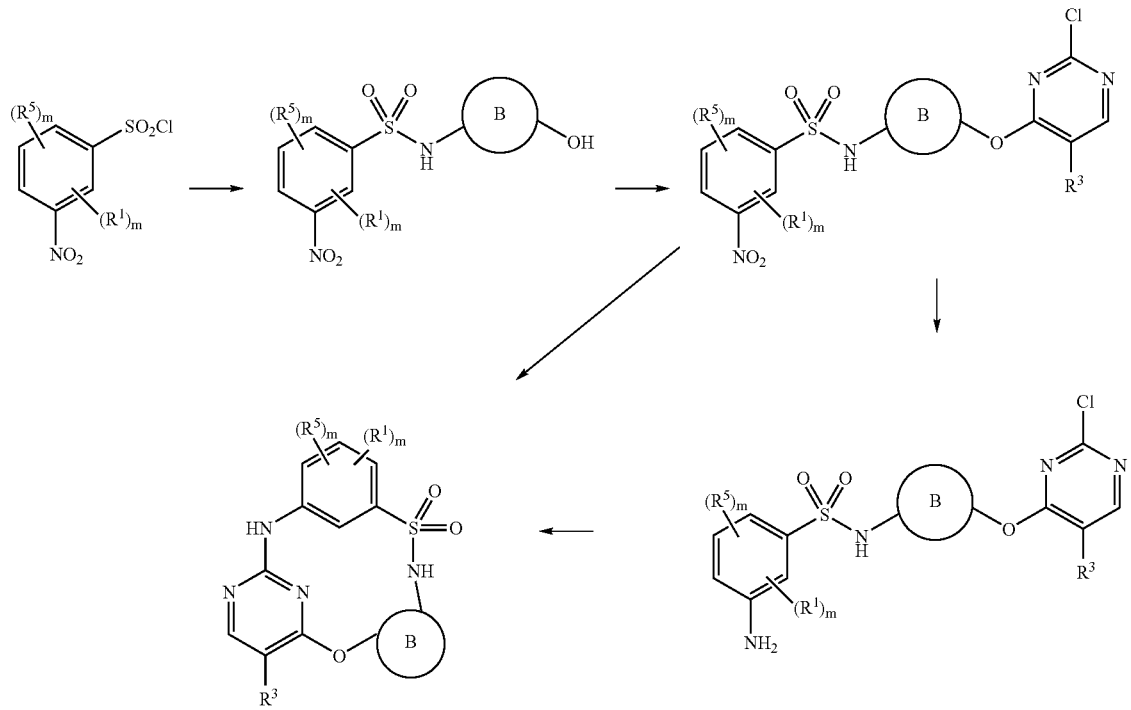

¹H-NMR (DMSO): 10.23 (s, 1H), 9.08 (m, 1H), 8.41 (s, 1H), 7.88 (br, 1H), 7.36 (m, 3H), 4.58 (m, 2H), 3.30 (m, 2H), 2.07 (m, 2H). MS: 385 (ES).

Production of Intermediate Products According to Process Variant 3a

3a) Production of N-[3-(5-Bromo-2-chloro-pyrimidin-4-yloxy)-propyl]-3-nitro-benzenesulfonamide

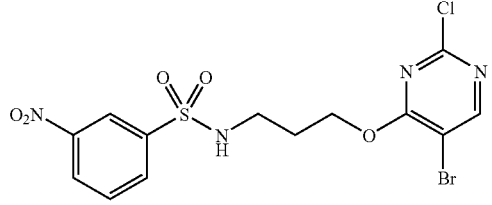

A solution of 272 mg (1.05 mmol) of N-(3-hydroxypropyl)-3-nitro-benzenesulfonamid in 5 ml DMF is mixed with 49 mg of a 60% dispersion of sodium hydride in mineral oil (1.22 mmol) and stirred for 5 minutes at room temperature. It is mixed with a solution of 220 mg (0.97 mmol) of 5-bromo-2,4-dichloro-pyrimidine in 5 ml of DMF and stirred for another 2 hours. The batch is mixed with saturated NaCl solution and then extracted with ethyl acetate (2×). The combined organic phases are washed with NaCl solution, dried (Na₂SO₄), filtered and concentrated by evaporation. The remaining residue is purified by chromatography (hexane/ethyl acetate 1:1, Flashmaster II). 75 mg (0.16 mmol, corresponding to 16% of theory) of the product is obtained.

¹H-NMR (DMSO): 8.66 (s, 1H), 8.47 (m, 2H), 8.16 (m, 1H), 8.06 (m, 1H), 7.88 (t, 1H), 4.37 (t, 2H), 3.00 (m, 2H), 1.96 (m, 2H). MS: 451 (ES).

3b) Production of 3-Amino-N-[3-(5-bromo-2-chloro-pyrimidin-4-yloxy)-propyl]-benzenesulfonamide

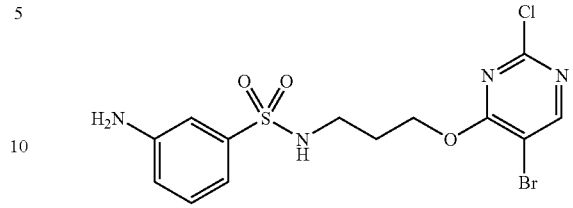

A solution of 70 mg (0.16 mmol) of N-[3-(5-bromo-2-chloro-pyrimidin-4-yloxy)-propyl]-3-nitro-benzenesulfonamide in 5 ml of THF is mixed at 0° C. with 1.0 ml of a 15% solution of Ti(III)Cl in approximately 10% hydrochloric acid. After 2 hours, the reaction solution is mixed again with 0.2 ml of Ti(III)Cl solution and stirred for another hour. The batch is made basic with 1N NaOH solution and then filtered. The filter cake is rewashed 2× in each case with 50 ml of ethyl acetate/MeOH (30 ml/20 ml). The filtrate is concentrated by evaporation in a rotary evaporator and then extracted with ethyl acetate (2×). The combined organic phases are washed with NaCl solution, dried (Na₂SO₄), filtered and concentrated by evaporation. The remaining residue is purified by chromatography (hexane/ethyl acetate 1:1, Flashmaster II). 32 mg (0.08 mmol, corresponding to 49% of theory) of the product is obtained.

¹H-NMR (DMSO): 8.67 (s, 1H), 7.49 (t, 1H), 7.12 (t, 1H), 6.96 (m, 1H), 6.81 (m, 1H), 6.68 (m, 1H), 5.54 (s, 1H), 4.39 (m, 2H), 2.96 (m, 2H), 1.87 (m, 2H). MS: 421 (ES).

Production of 5-Carboxamide Derivatives

Process Variant 4

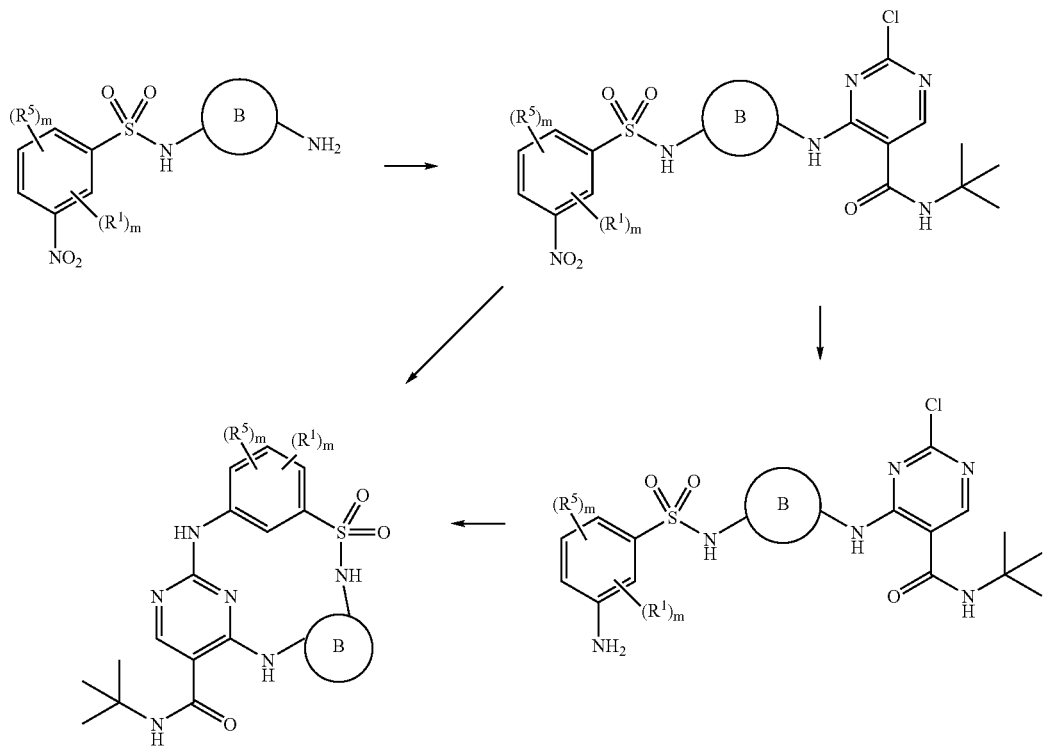

In the general formulas, $R^1$, $R^5$, B and m have the meaning that is indicated under general formula I.

EXAMPLE 4.0

Production of N-tert-Butyl-4-thia-2,5,9-triaza-1(2,4)-pyrimidina-3(1,3)-benzenacyclononaphane-$1^5$-carboxamide-4,4-dioxide

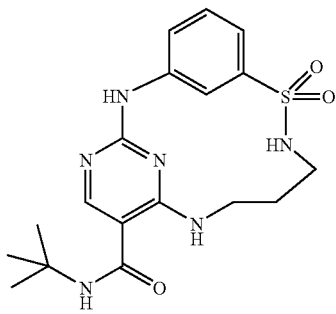

A solution of 150 mg (0.32 mmol) of 2-chloro-4-[3-(3-nitro-benzenesulfonylamino)-propylamino]-pyrimidine-5-carboxylic acid-tert-butylamide in 10 ml of THF is mixed under argon at room temperature with 1.6 ml of a 15% solution of Ti(III)Cl in approximately 10% hydrochloric acid. After 17 hours, the reaction solution is mixed again with 0.3 ml of Ti(III)Cl solution and stirred for another 4 hours. The batch is made basic with 1 M NaOH solution and then filtered. The filter cake is rewashed 2× with 50 ml of ethyl acetate/MeOH (30 ml/20 ml) in each case. The filtrate is concentrated by evaporation in a rotary evaporator and then extracted with ethyl acetate (2×). The combined organic phases are dried ($Na_2SO_4$), filtered and concentrated by evaporation. During concentration by evaporation, a colorless solid precipitates, which is filtered off and dried. 25 mg (0.06 mmol, corresponding to 18% of theory) of the product is obtained.

$^1$H-NMR (DMSO): 9.95 (s, 1H), 9.45 (s, 1H), 8.82 (t, 1H), 8.49 (s, 1H), 7.78 (t, 1H), 7.58 (s, 1H), 7.38 (m, 3H), 3.50 (m, 2H), 3.30 (m, 2H), 1.86 (m, 2H) MS: 405 (ES)

Production of the Intermediate Products According to Process Variant 4

4a) Production of 2,4-Dichloro-pyrimidine-5-carbonyl Chloride

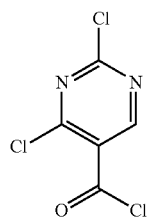

A suspension of 21.7 g (139 mmol) of 2,4-dihydroxy-5-carboxylic acid-pyrimidine, 96.7 g (463 mmol) of phosphorus pentachloride and 33 ml (348 mmol) of phosphoroxyde chloride is stirred for 5 hours at 115° C. After cooling, the reaction mixture is concentrated by evaporation in a rotary evaporator. The residue that is formed is purified by vacuum distillation ($K_{p\ 0.1\ mbar}$: 68° C.). 24.9 g (117 mmol, corresponding to 84% of theory) of the product is obtained.

$^1$H-NMR (DMSO): 9.11 (s, 1H)

4b) Production of 2,4-Dichloro-pyrimidine-5-carboxylic acid-tert-butylamide

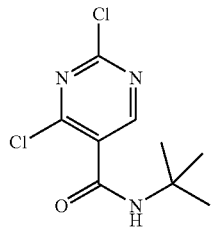

A solution of 24.85 g (117.5 mmol) of 2,4-dichloro-pyrimidine-5-carbonyl chloride in 125 ml of THF is cooled to −15° C. It is slowly mixed with a solution of 13.2 ml (124.5 mmol) of tert-buylamine and 17.4 ml (125.7 mmol) of triethylamine in 50 ml of THF, so that the temperature of the reaction mixture remains less than −10° C. It is stirred for another 2 hours at −10° C., then the cooling bath is removed, and the reaction mixture is heated to room temperature while being stirred. After 1 hour, the precipitate that is formed is filtered off, and the filtrate is completely concentrated by evaporation. The residue that is obtained is purified by chromatography (hexane/ethyl acetate 4:1). 14.01 g (56.6 mmol, corresponding to 50% of theory) of the product is obtained.

$^1$H-NMR (DMSO): 8.81 (s, 1H), 8.34 (s, 1H), 1.36 (s, 9H)

4c) 2-Chloro-4-[3-(3-nitro-benzenesulfonylamino)-propylamino]-pyrimidine-5-carboxylic acid-tert-butylamide

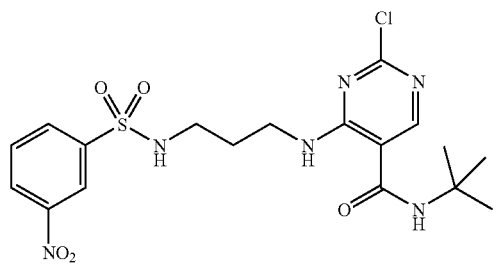

A solution of 0.95 g (3.83 mmol) of 2,4-dichloro-pyrimidine-5-carboxylic acid-tert-butylamide in 6 ml of THF is mixed at room temperature while being stirred with a suspension that consists of 1.00 g (3.86 mmol) of N-(3-amino-propyl)-3-nitro-benzenesulfonamide in 9 ml of THF/ 0.55 ml of triethylamine. After 19 hours, the precipitate that is formed is suctioned off and washed with ethyl acetate. The filtrate is spun in, and the residue that is formed is purified by chromatography (hexane/ethyl acetate 2:1, Flashmaster II). 0.79 g (1.67 mmol, corresponding to 44% of theory) of the product is obtained.

$^1$H-NMR (DMSO): 8.74 (t, 1H), 8.47 (m, 3H), 8.18 (dd, 1H), 8.04 (t, 1H), 7.98 (s, 1H), 7.85 (t, 1H), 3.30 (m, 2H), 2.87 (m, 2H), 1.68 (m, 2H), 1.36 (s, 9H)

Production of 5-Cyano Derivatives

Process Variant 5

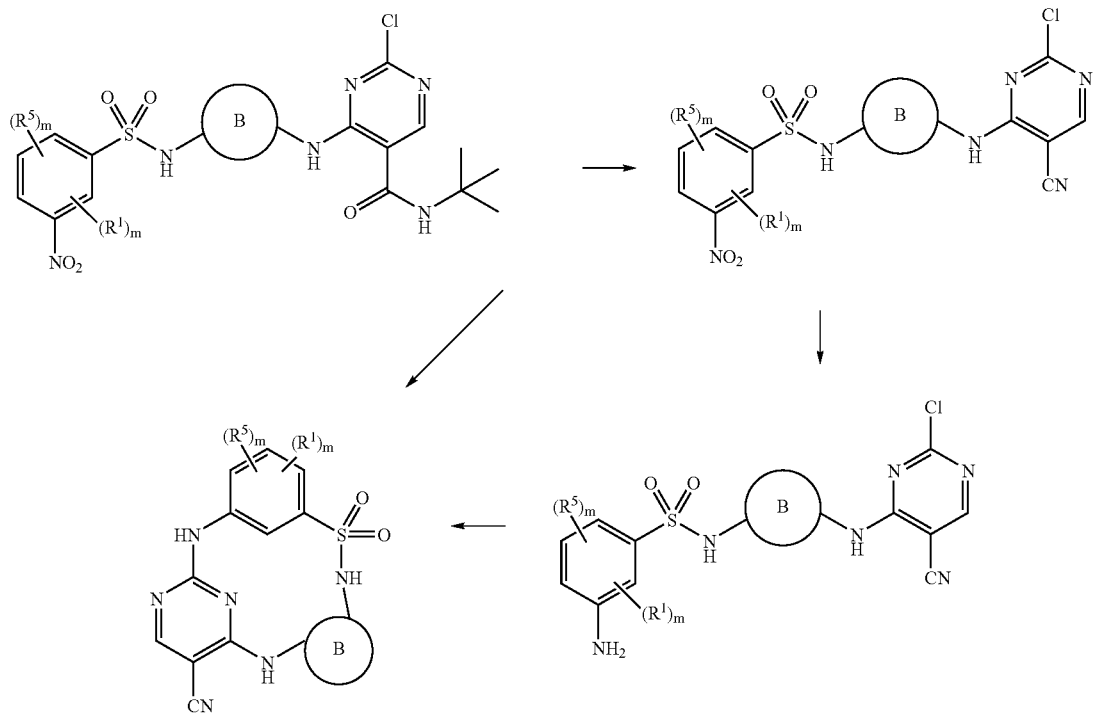

In the general formulas, $R^1$, $R^5$, B and m have the meaning that is indicated under general formula I.

EXAMPLE 5.0

Production of $1^5$-Cyano-4-thia-2,5,9-triaza-1(2,4)-pyrimidina-3(1,3)-benzenacyclononaphane 4,4-dioxide

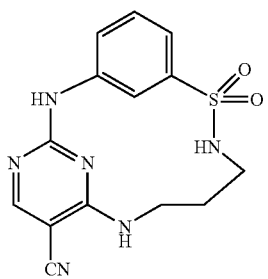

A solution of 100 mg (0.25 mmol) of N-[3-(2-chloro-5-cyano-pyrimidin-4-ylamino)-propyl]-3-nitro-benzenesulfonamide in 10 ml of THF is mixed under argon at room temperature with 1.2 ml of a 15% solution of Ti(III)Cl in approximately 10% hydrochloric acid. After 3.5 hours, the batch is diluted with ethyl acetate, made basic with 1 M NaOH solution (pH 13) and then filtered. The filter cake is rewashed with 50 ml of ethyl acetate/MeOH (30 ml/20 ml) and 70 ml of ethyl acetate/MeOH/1N NaOH (40 ml/20 ml/10 ml). The filtrate is concentrated by evaporation in a rotary evaporator and then extracted with ethyl acetate (2×). The combined organic phases are dried ($Na_2SO_4$), filtered and concentrated by evaporation. During concentration by evaporation, the product precipitates as a colorless solid, which is filtered off. 30 mg (0.09 mmol, corresponding to 36% of theory) of the product is obtained.

$^1$H-NMR (DMSO): 10.29 (s, 1H), 9.29 (s, 1H), 8.39 (s, 1H), 8.15 (br, 1H), 7.78 (br, 1H), 7.38 (m, 3H), 3.30 (m, 4H), 1.85 (m, 2H) MS: 331 (ES)

Production of Intermediate Products According to Process Variant 5

5a) Production of N-[3-(2-Chloro-5-cyano-pyrimidin-4-ylamino)-propyl]-3-nitro-benzenesulfonamide

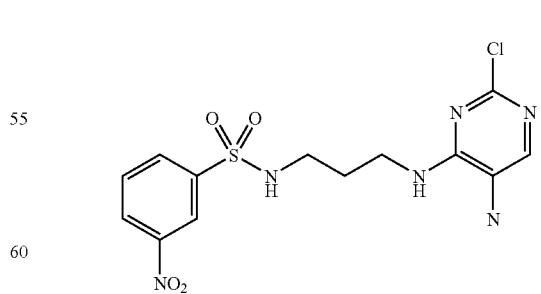

125 mg (0.27 mmol) of 2-chloro-4-[3-(3-nitro-benzenesulfonylamino)-propylamino]-pyrimidine-5-carboxylic acid-tert-butylamide is mixed with 4 ml of thionyl chloride and stirred under reflux for 19 hours. The reaction mixture is concentrated by evaporation. It is mixed with water and toluene and evaporated to the dry state in a rotary evaporator. 110 mg (0.27 mmol, corresponding to 100% of theory) of the product is obtained.

¹H-NMR (DMSO): 8.50 (m, 4H), 8.19 (d, 1H), 8.01 (t, 1H), 7.88 (t, 1H), 3.30 (m, 2H), 2.87 (m, 2H), 1.71 (m, 2H).

Production of Thiophene Derivatives is added via a spray pump within 2 hours to a refluxing solution of acetonitrile/water/4 molar solution of hydrochloric acid in dioxane (64 ml/7 ml/0.8 ml). After the addition is completed, the reaction mixture is stirred under reflux for another 6 hours. After cooling, the solvent is drawn off in a rotary evaporator. The residue is mixed with 2N NaOH and extracted with ethyl acetate (2×). The combined organic

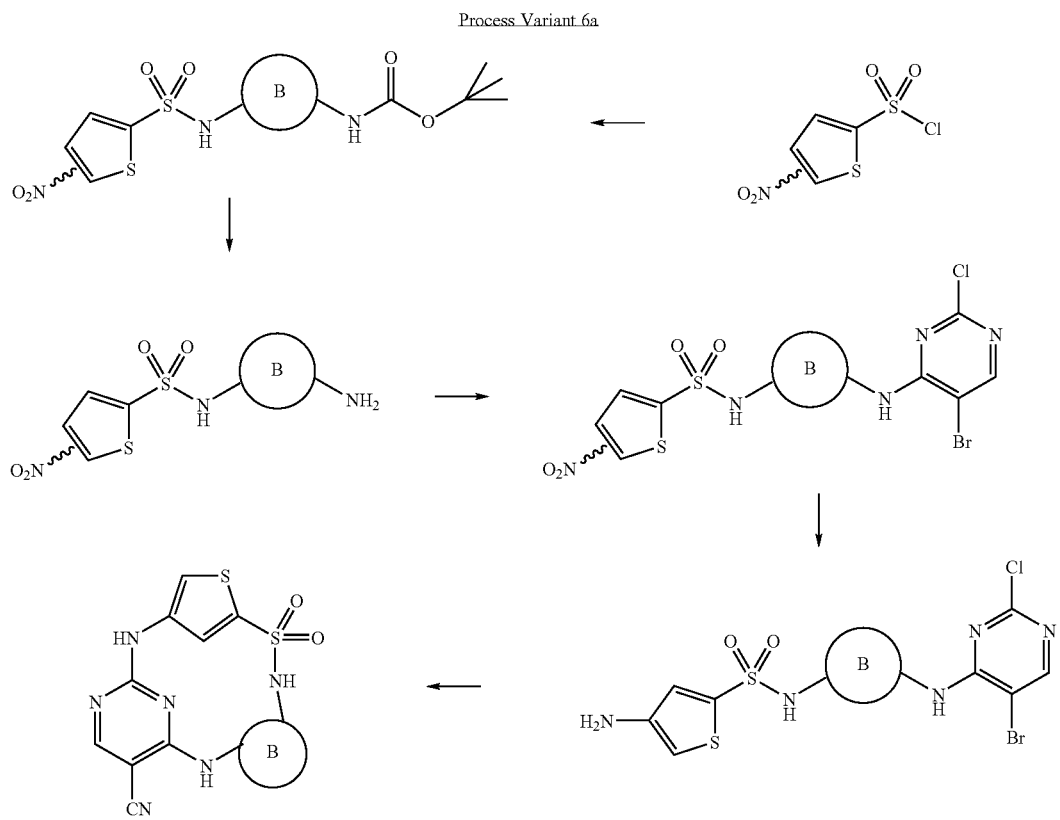

Process Variant 6a

In the general formulas, R³ and B have the meaning that is indicated under general formula I.

EXAMPLE 6.0

Production of 1⁵-Bromo-4-thia-2,5,8-triaza-1(2,4)-pyrimidina-3(4,2)-thiophenacyclooctaphane-4,4-dioxides

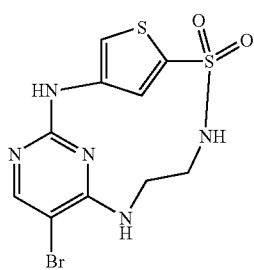

A solution of 170 mg (0.41 mmol) of 4-amino-thiophenylene-2-sulfonic acid-[2-(5-bromo-2-chloro-pyrimidin-4-ylamino)-ethyl]-amide in acetonitrile/water (12.0 ml/1.5 ml)

phases are filtered through a Whatman filter and concentrated by evaporation. The remaining residue is crystallized from MeOH/diisopropyl ether. 41 mg (0.11 mmol, corresponding to 27% of theory) of the product is obtained.

¹H-NMR (DMSO): 9.03 (s, 1H), 7.92 (s, 1H), 7.68 (d, 1H), 7.48 (br, 1H), 7.38 (d, 1H), 7.08 (t, 1H), 2.91 (m, 4H) MS: 376 (ES)

Production of Intermediate Products According to Process Variant 6a

6a) Production of 4-Nitro-thiophene-2-sulfonyl Chloride (A) and 5-Nitro-thiophene-2-sulfonyl Chloride (B)

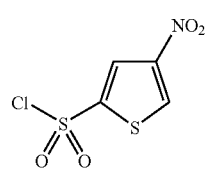

A

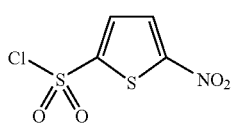

A solution of 25 g (137 mmol) of thiophene-2-sulfonyl chloride in 20 ml of dichloromethane is slowly added in drops to 98 ml of concentrated nitric acid while being stirred. The reaction mixture is stirred for 2 hours at 40° C. and then added to ice. It is extracted with dichloromethane (2×). The combined organic phases are dried on MgSO$_4$, filtered, and concentrated by evaporation. 24 g (105 mmol, corresponding to 77% of theory) of a mixture of products A and B in a ratio of 2/1 is obtained.

$^1$H-NMR (DMSO): 8.63 (d, 1H, A), 7.93 (d, 1H, B), 7.54 (d, 1H, A), 7.18 (d, 1H, B)

6b) Production of [2-(4-Nitro-thiophene-2-sulfonylamino)-ethyl]-carbamic acid-tert-butylester (A) and [2-(5-Nitro-thiophene-2-sulfonylamino)-ethyl]-carbamic acid-tert-butyl-ester (B)

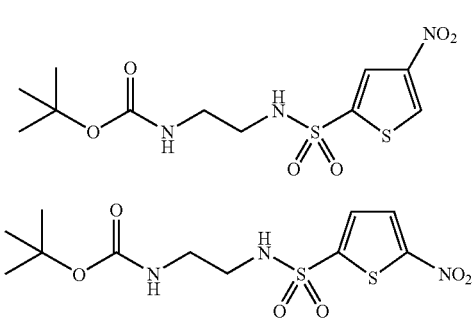

2.8 ml (20 mmol) of triethylamine is added to a solution of 2.27 g (10 mmol) of a mixture of 4-nitro-thiophene-2-sulfonyl chloride and 5-nitro-thiophene-2-sulfonyl chloride in a ratio of 2/1 as well as 1.64 g (10 mmol) of (2-amino-ethyl)-carbamic acid-tert-butyl ester in 40 ml of acetone and 10 ml of water. The reaction mixture is stirred for 3 hours at room temperature, and then the acetone is drawn off in a rotary evaporator. After water (20 ml) is added, it is extracted with ethyl acetate (2×). The combined organic phases are filtered through a Whatman filter and concentrated by evaporation. 2.65 g (7.5 mmol, corresponding to 75% of theory) of a mixture of compounds A and B in a ratio of 1/1 is obtained.

$^1$H-NMR (DMSO): 9.02 (d, 1H, A), 8.85 (t, 1H), 8.15 (m, 2H), 8.02 (d, 1H, A), 7.63 (d, 1H, B), 6.78 (m, 2H), 2.92 (m, 8H), 1.40 (s, 18H).

6c) Production of 4-Nitro-thiophene-2-sulfonic Acid-[2-(5-bromo-2-chloro-pyrimidin-4-ylamino)-ethyl]-amide (A) and 5-Nitro-thiophene-2-sulfonic Acid-[2-(5-bromo-2-chloro-pyrimidin-4-ylamino)-ethyl]-amide (B)

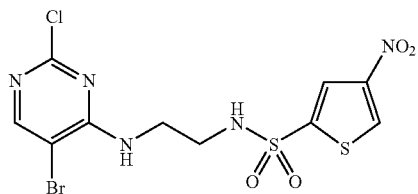

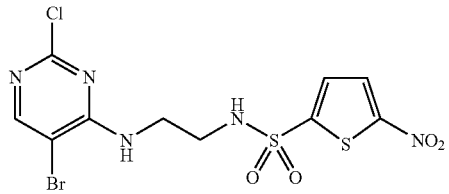

2.65 g (7.54 mmol) of a mixture of [2-(4-nitro-thiophene-2-sulfonylamino)-ethyl]-carbamic acid-tert-butyl ester and [2-(5-nitro-thiophene-2-sulfonylamino)-ethyl]-carbamic acid-tert-butyl ester at a ratio of 1/1 is mixed with 9 ml of TFA and stirred for 2.5 hours at room temperature. The reaction mixture is concentrated by evaporation in a rotary evaporator and mixed with water and 1N NaOH (pH 13). It is extracted with ethyl acetate (2×). The combined organic phases are filtered through a Whatman filter and concentrated by evaporation. The remaining residue is purified by chromatography (dichloromethane/MeOH 1:1). The crude product that is obtained is taken up in 3 ml of acetonitrile and mixed with a solution of 1.37 g (3 mmol) of 5-bromo-2,4-dichloro-pyrimidine/1 ml of triethylamine (7 mmol) in 3 ml of acetonitrile. After 16 hours, the reaction mixture is concentrated by evaporation in a rotary evaporator, and the remaining residue is purified by chromatography (hexane/ethyl acetate 2:1, Flashmaster II). 0.87 g (1.97 mmol, corresponding to 26% of theory) of a mixture of regioisomers A and B in a ratio of 10/6 is obtained.

$^1$H-NMR (DMSO): 8.98 (d, 1H, A), 8.50 (t, 1H, B), 8.32 (t, 2H, A), 8.20 (s, 2H, A+B), 8.05 (d, 1H, B), 7.98 (d, 1H, A), 7.63 (m, 3H, A+B), 3.47 (m, 4H, A+B), 3.20 (m, 4H, A+B) MS: 4.42 (ES)

6d) 4-Amino-thiophene-2-sulfonic acid-[2-(5-bromo-2-chloro-pyrimidin-4-ylamino)-ethyl]-amide

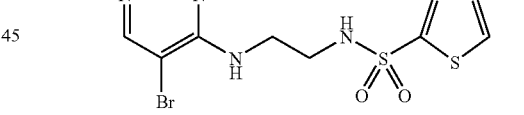

A solution of 600 mg (1.35 mmol) of a mixture of 4-nitro-thiophene-2-sulfonic acid [2-(5-bromo-2-chloro-pyrimidin-4-ylamino)-ethyl]-amide and 5-nitro-thiophene-2-sulfonic acid-[2-(5-bromo-2-chloro-pyrimidin-4-ylamino)-ethyl]-amide (ratio 10/6) in 40 ml of THF is mixed under argon at room temperature with 6.4 ml of a 15% solution of Ti(III)Cl in approximately 10% hydrochloric acid. After 46 hours, the reaction solution is mixed again with 2.0 ml of Ti(III)Cl solution and stirred for another 7 hours. The batch is made basic with 2N NaOH solution and then filtered. The filter cake is rewashed 2× with 50 ml of ethyl acetate/MeOH (30 ml/20 ml) in each case. The filtrate is concentrated by evaporation in a rotary evaporator and then extracted with ethyl acetate (2×). The combined organic phases are filtered through a Whatman filter and concentrated by evaporation. The residue is purified by chromatography (hexane/ethyl acetate 1:4). 178 mg (0.43 mmol, corresponding to 32% of theory) of the product is obtained.

¹H-NMR (DMSO): 8.21 (s, 1H), 7.82 (t, 1H), 7.65 (t, 1H), 7.03 (d, 1H), 6.31 (d, 1H), 5.21 (br, 2H), 3.44 (m, 2H), 3.02 (m, 2H). MS: 412 (ES)

Production of Intermediate Products According to Process Variant 6b

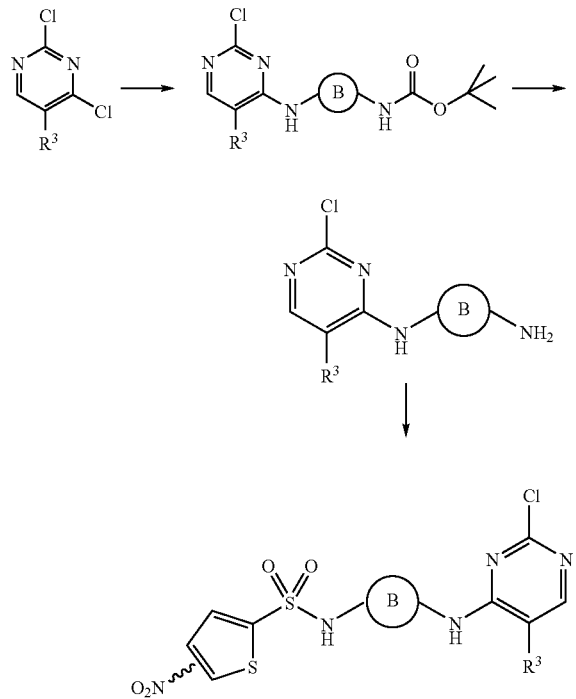

In the general formulas, $R^3$ and B have the meaning that is indicated under general formula I.

6e) Production of 4-Nitro-thiophene-2-sulfonic Acid-[3-(5-bromo-2-chloro-pyrimidin-4-ylamino)-propyl]-amide (A) and 5-Nitro-thiophene-2-sulfonic Acid-[3-(5-bromo-2-chloro-pyrimidin-4-ylamino)-propyl]-amide

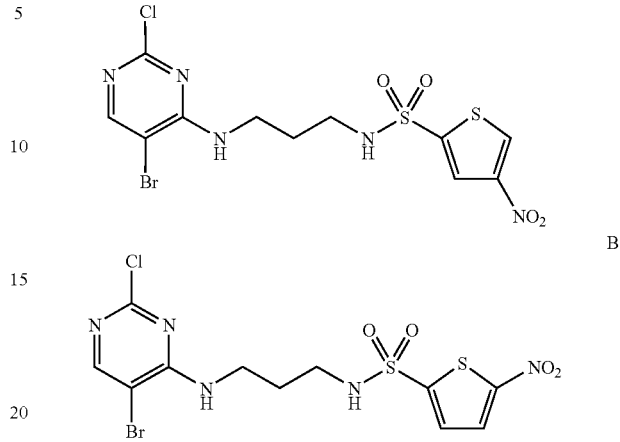

A solution of 995 mg (3.3 mmol) of N-(5-bromo-2-chloro-pyrimidin-4-yl)-propane-1,3-diamine hydrochloride and 700 mg (3.1 mmol) of a mixture of 4-nitro-thiophene-2-sulfonyl chloride and 5-nitro-thiophene-2-sulfonyl chloride at a ratio of 1/1 in 40 ml of acetone/10 ml of water is mixed at room temperature with 2 ml (14.4 mmol) of triethylamine. After 15 minutes, the organic solvent is drawn off on a rotary evaporator. It is mixed with 150 ml of ethyl acetate and washed with citric acid (10%), saturated NaHCO₃ solution, as well as saturated NaCl solution. The organic phase is dried (Na₂SO₄), filtered and concentrated by evaporation. 860 mg (1.9 mmol, corresponding to 62% of theory) of a mixture of products A and B at a ratio of 1/1 is obtained.

¹H-NMR (DMSO): 9.00 (d, 1H, A), 8.39 (t, 1H), 8.20 (m, 4H), 8.12 (d, 1H, B), 8.02 (d, 1H, A), 7.68 (t, 1H), 7.61 (d, 1H, B), 3.30 (m, 4H), 2.90 (m, 4H), 1.75 (m, 4H).

Production of Oxa-phanes and Introduction of Sulfamoyl Groupings

Process Variant 7

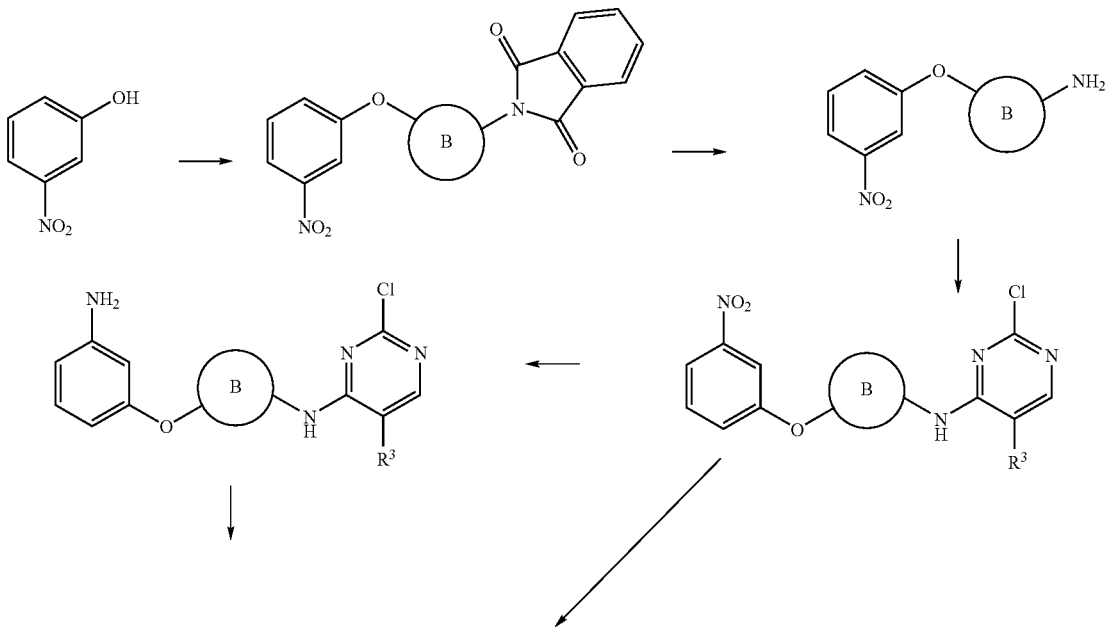

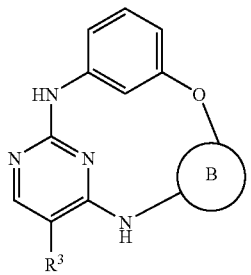  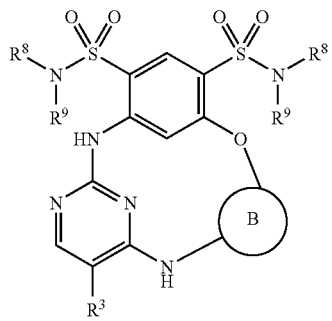

In the general formulas, $R^3$, $R^8$, $R^9$ and B have the meaning that is indicated under general formula I.

EXAMPLE 7.0

Production of $1^5$-Bromo-N,N'-dimethyl-4-oxa-2,9-diaza-1(2,4)-pyrimidina-3(1,3)-benzenacyclononaphane-$3^4$,$3^6$-disulfonamide

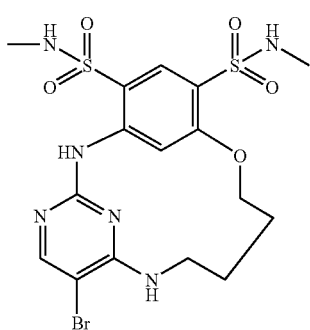

10 ml of chlorosulfonic acid is mixed carefully with 75 mg of phosphorus pentachloride while being cooled (4° C.). 60 mg (0.18 mmol) of $1^5$-brom-4-oxa-2,9-diaza-1(2,4)-pyrimidina-3(1,3)-benzenacyclononaphane is added, and it is stirred for 3 hours at room temperature. The reaction mixture is added carefully to ice water and stirred for 1 hour. The solid that is formed is suctioned off and taken up in 1 ml of THF. It is mixed with 2 ml of a solution of methylamine in ethanol, and it is stirred for 12 hours at room temperature. The reaction mixture is concentrated by evaporation, and the remaining residue is purified by chromatography (dichloromethane/methanol 1:1). 8 mg (0.02 mmol, corresponding to 10% of theory) of the product is obtained.

$^1$H-NMR (DMSO): 9.43 (s, 1H), 9.17 (s, 1H), 8.15 (s, 1H), 8.03 (s, 1H), 7.95 (q, 1H), 7.72 (t, 1H), 7.15 (q, 1H), 4.55 (br, 2H), 3.42 (br, 2H), 2.45 (m, 6H), 1.91 (m, 4H). MS: 521 (ES).

EXAMPLE 7.1

Production of $1^5$-Bromo-4-oxa-2,9-diaza-1(2,4)-pyrimidina-3(1,3)-benzenacyclononaphane

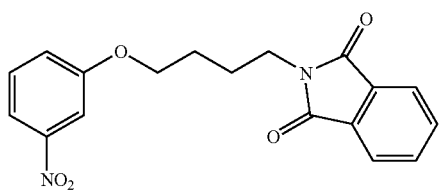

A solution of 295 mg (0.79 mmol) of [4-(3-aminophenoxy)-butyl]-(5-bromo-2-chloro-pyrimidin-4-yl)-amine in acetonitrile/water (18 ml/2 ml) is added via a spray pump within 4.5 hours to a refluxing solution of acetonitrile/water/4 molar solution of hydrochloric acid in dioxane (105 ml/12 ml/1.4 ml). After another 60 minutes under reflux, the oil bath is turned off, and the reaction solution is stirred overnight at room temperature. The reaction mixture is made basic with 2N NaOH and extracted with ethyl acetate (3×). The combined organic phases are washed with NaCl solution, dried (MgSO$_4$), filtered and concentrated by evaporation. The remaining residue is digested with methanol. 65 mg (0.19 mmol, corresponding to 24% of theory) of the product is obtained.

$^1$H-NMR (DMSO): 9.31 (s, 1H), 8.82 (s, 1H), 8.01 (s, 1H), 7.37 (br, 1H), 7.02 (t, 1H), 6.63 (d, 1H), 6.36 (dd, 1H), 4.34 (br, 2H), 3.30 (m, 2H), 1.85 (m, 4H). MS: 335 (ES).

Production of Intermediate Products According to Process Variant 7

7a) Production of 2-[4-(3-Nitro-phenoxy)-butyl]-isoindole-1,3-dione 9.67 g (70 mmol) of potassium carbonate is added to a solution of 6.96 g (50 mmol) of 3-nitrophenol in 500 ml DMF, and then it is stirred for 10 minutes at room temperature. It is mixed with 14.1 g (50 mmol) of 2-(4-bromobutyl)-isoindole-1,3-dione and stirred for 4 hours at 60° C. After cooling, it is mixed with water and extracted with ethyl acetate. The combined organic phases are dried (MgSO₄), filtered and concentrated by evaporation. 17.2 g (50 mmol, corresponding to 100% of theory) of the product is obtained.

¹H-NMR (CDCl₃): 7.85 (m, 3H), 7.70 (m, 3H), 7.40 (t, 1H), 7.18 (dd, 1H), 4.06 (m, 2H), 3.80 (m, 2H), 1.95 (m, 4H).

7b) Production of 4-(3-Nitro-phenoxy)-butylamine

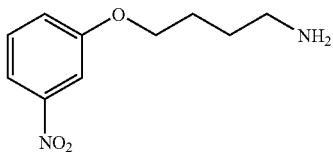

A solution of 17.0 g (50 mmol) of 2-[4-(3-nitro-phenoxy)-butyl]-isoindole-1,3-dione in 1000 ml of ethanol is mixed with 25 ml of hydrazine and stirred for 2 hours at 70° C. After cooling, the precipitate that is formed is suctioned off, and the filtrate is spun in. The residue is taken up in dichloromethane. It is filtered again, and the filtrate is fully concentrated by evaporation. 5.8 g (28 mmol, corresponding to 56% of theory) of the product is obtained.

¹H-NMR (CDCl₃): 7.79 (dd, 1H), 7.71 (t, 1H), 7.39 (t, 1H), 7.20 (dd, 1H), 4.03 (m, 2H), 2.79 (m, 2H), 1.85 (m, 2H), 1.70 (m, 2H).

7c) Production of (5-Bromo-2-chloro-pyrimidin-4-yl)-[4-(3-nitro-phenoxy)-butyl]-amine

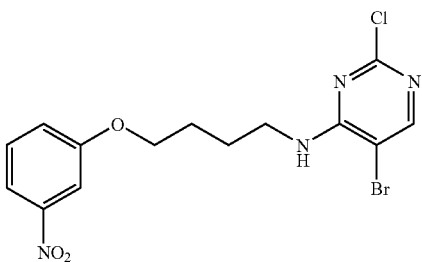

A solution of 2.28 g (10 mmol) of 5-bromo-2,4-dichloropyrimidine and 1.4 ml of triethylamine (10 mmol) in 32 ml of acetonitrile is mixed at 4° C. while being stirred with a solution of 2.1 g (10 mmol) of 4-(3-nitro-phenoxy)-butylamine in 5 ml of acetonitrile. After 12 hours, it is diluted with ethyl acetate and filtered. The filtrate is concentrated by evaporation in a rotary evaporator, and the remaining residue is purified by chromatography (hexane/ethyl acetate 1:1, Flashmaster II). 2.7 g (7 mmol, corresponding to 70% of theory) of the product is obtained.

¹H-NMR (CDCl₃): 8.11 (s, 1H), 7.81 (dd, 1H), 7.71 (t, 1H), 7.44 (t, 1H), 7.20 (dd, 1H), 5.62 (br, 1H), 4.11 (m, 2H), 3.62 (m, 2H), 1.92 (m, 4H).

7d) Production of 4-(3-Amino-phenoxy)-butyl]-(5-bromo-2-chloro-pyrimidin-4-yl)-amine

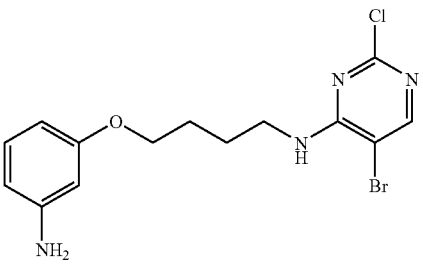

A solution of 401 mg (1.00 mmol) of (5-bromo-2-chloro-pyrimidin-4-yl)-[4-(3-nitro-phenoxy)-butyl]-amine in 30 ml of THF is mixed under argon at room temperature with 4.5 ml of a 15% solution of Ti(III)Cl in approximately 10% hydrochloric acid. After 3.5 hours, the reaction solution is again mixed with 0.2 ml of Ti(III)Cl solution and stirred for another 12 hours. The batch is made basic with 2N NaOH solution and then filtered. The filter cake is rewashed 2× with 50 ml of ethyl acetate/MeOH (30 ml/20 ml) in each case. The filtrate is concentrated by evaporation in a rotary evaporator and then extracted with ethyl acetate (2×). The combined organic phases are washed with NaCl solution, dried (MgSO₄), filtered and concentrated by evaporation. The remaining residue is purified by chromatography (hexane/ethyl acetate 1:1, Flashmaster II). 300 mg (0.81 mmol, corresponding to 81% of theory) of the product is obtained.

¹H-NMR (CDCl₃): 8.10 (s, 1H), 7.03 (t, 1H), 6.36 (m, 3H), 5.66 (br, 1H), 3.97 (m, 2H), 3.60 (m, 2H), 1.86 (m, 2H). MS: 371 (ES)

Production of the Sulfonamide-oxa-cyclophanes

Process Variant 8a

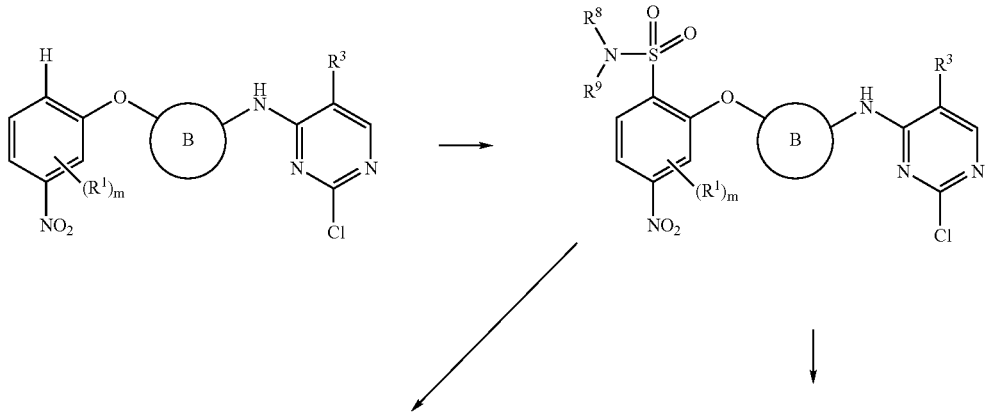

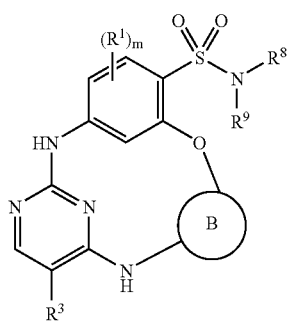 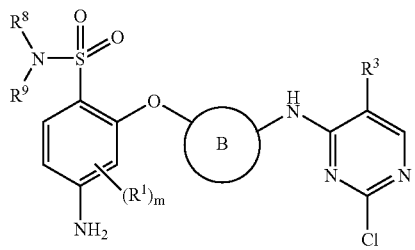

In the general formulas, $R^1$, $R^3$, $R^8$, $R^9$, B and m have the meaning that is indicated under general formula I.

EXAMPLE 8.0

Production of $1^5$-Bromo-4-oxa-2,9-diaza-1(2,4)-pyrimidina-3(1,3)-benzenacyclononaphane-$3^4$-sulfonamide

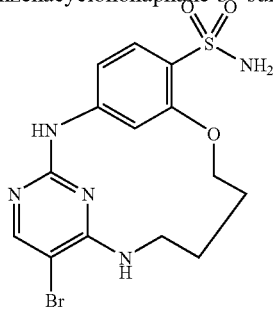

A solution of 66 mg (0.15 mmol) of 4-amino-2-[4-(5-bromo-2-chloro-pyrimidin-4-ylamino)-butoxy]-benzenesulfonamide in acetonitrile/water/2-butanol (8 ml/1 ml/1 ml) is added via a spray pump within 3.5 hours to a refluxing solution of acetonitrile/water/4 molar solution of hydrochloric acid in dioxane (45 ml/5 ml/0.6 ml). After another 16 hours under reflux, the reaction mixture is concentrated by evaporation in a rotary evaporator. The batch is made basic with 1N NaOH (pH 13) and extracted with ethyl acetate (2×). The combined organic phases are dried (MgSO$_4$), filtered and concentrated by evaporation. The remaining residue is digested with hexane and tert-butyl methyl ether. 55 mg (0.13 mmol, corresponding to 87% of theory) of the product is obtained.

$^1$H-NMR (DMSO): 9.70 (s, 1H), 9.10 (d, 1H), 8.06 (s, 1H), 7.49 (m, 2H), 6.82 (s, 2H), 6.67 (dd, 1H), 4.45 (br, 2H), 3.40 (m, 2H), 1.85 (m, 4H) MS: 414 (ES).

Production of the Intermediate Products According to Process Variant 8a

8a) Production of 2-[4-(5-Bromo-2-chloro-pyrimidin-4-ylamino)-butoxy]-4-nitro-benzenesulfonamide (A) and 4-[4-(5-Bromo-2-chloro-pyrimidin-4-ylamino)-butoxy]-2-nitro-benzenesulfonamide (B)

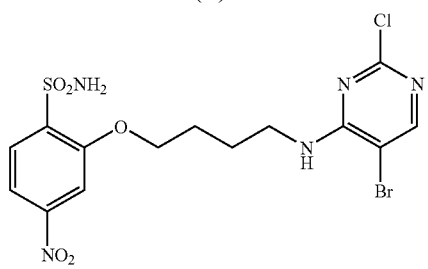

A

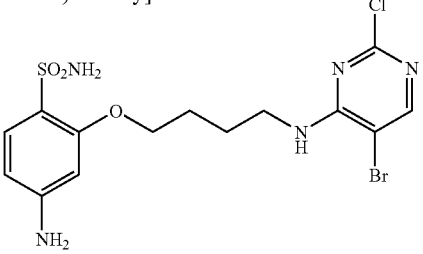

B 402 mg (1.01 mmol) of (5-bromo-2-chloro-pyrimidin-4-yl)-[4-(3-nitro-phenoxy)-butyl]-amine is introduced in portions in 4 ml of ice-cold chlorosulfonic acid (cooling: ice/methanol), and then it is stirred for 3 hours at room temperature. The batch is carefully added to ice water while being stirred. The precipitate that is formed is suctioned off, taken up in acetone and mixed with concentrated ammonia. It is stirred for 2 hours at room temperature, and the batch is concentrated by evaporation in a rotary evaporator. It is mixed with water and extracted with ethyl acetate (2×). The combined organic phases are dried (MgSO$_4$), filtered and concentrated by evaporation. The remaining residue is purified by chromatography (hexane/ethyl acetate 1:1). 190 mg (0.40 mmol, corresponding to 40% of theory) of product A and 110 mg (0.23 mmol, corresponding to about 23% of theory) of product B are obtained.

2-[4-(5-Bromo-2-chloro-pyrimidin-4-ylamino)-butoxy]-4-nitro-benzenesulfonaride (A):

$^1$H-NMR (DMSO): 8.25 (s, 1H), 7.99 (d, 1H), 7.91 (m, 2H), 7.72 (br, 1H), 7.35 (br, 2H), 4.34 (m, 2H), 3.42 (m, 2H), 1.82 (m, 4H). MS: 480 (ES)

4-[4-(5-Bromo-2-chloro-pyrimidin-4-ylamino)-butoxy]-2-nitro-benzenesulfonamide (B):

$^1$H-NMR (DMSO): 8.22 (s, 1H), 7.93 (d, 1H), 7.78 (t, 1H), 7.67 (s, 2H), 7.51 (d, 1H), 7.34 (dd, 1H), 4.16 (m, 2H), 3.45 (m, 2H), 1.73 (m, 4H). MS: 480 (ES)

8b) Production of 4-Amino-2-[4-(5-bromo-2-chloro-pyrimidin-4-ylamino)-butoxy]-benzenesulfonamide A solution of 160 mg (0.33 mmol) of 2-[4-(5-bromo-2-chloro-pyrimidin-4-ylamino)-butoxy]-4-nitro-benzenesulfonamide in 10 ml of THF is mixed under argon at room temperature with 1.4 ml of a 15% solution of Ti(III)Cl in approximately 10% hydrochloric acid. After 4 hours, the reaction solution is again mixed with 0.2 ml of the Ti(III)Cl solution and stirred for another 14 hours. The batch is made basic with 2N NaOH solution and then filtered. The filter cake is rewashed 2× with 50 ml of ethyl acetate/MeOH (30 ml/20 ml) in each case. The filtrate is concentrated by evaporation in a rotary evaporator and then extracted with ethyl acetate (2×). The combined organic phases are washed with NaCl solution, dried (MgSO$_4$), filtered and concentrated by evaporation. The remaining residue is purified by chromatography (dichloromethane/methanol 9:1; Flashmaster II). 70 mg (0.81 mmol, corresponding to 47% of theory) of the product is obtained.

$^1$H-NMR (DMSO): 8.22 (s, 1H), 7.73 (t, 1H), 7.36 (d, 1H), 6.44 (s, 2H), 6.27 (d, 1H), 6.13 (dd, 1H), 5.78 (s, 2H), 4.04 (m, 2H), 3.45 (m, 2H), 1.76 (m, 4H) MS: 450 (ES)

EXAMPLE 8.1

Production of 1$^5$-Bromo-N-(dimethylaminomethylene)-4-oxa-2,9-diaza-1(2,4)-pyrimidina-3(1,3)-benzenacyclononaphane-3$^4$-sulfonamide

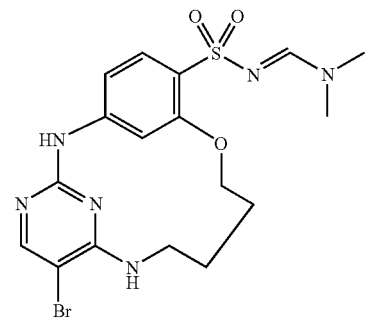

A suspension of 40 mg (0.096 mmol) of 1$^5$-bromo-4-oxa-2,9-diaza-1(2,4)-pyrimidina-3(1,3)-benzenacyclononaphane-3$^4$-sulfonamide in 1 ml DMF is mixed at room temperature with 0.02 ml of N,N-dimethylformamide dimethyl acetal and stirred overnight. The solvent is drawn off, and the remaining residue is digested with MTB ether. 40 mg (0.085, corresponding to 88% of theory) of the product is obtained.

$^1$H-NMR (DMSO): 9.70 (s, 1H), 8.98 (m, 1H), 8.17 (s, 1H), 8.04 (s, 1H), 7.53 (m, 1H), 7.45 (t, 1H), 6.69 (m, 1H), 4.35 (m, 2H), 3.35 (m, 2H), 3.18 (s, 3H), 2.88 (s, 3H), 1.80 (m, 4H). MS: 469 (ES).

Production of Sulfonamide-Oxa-Cyclophanes According to Process Variant 8b)

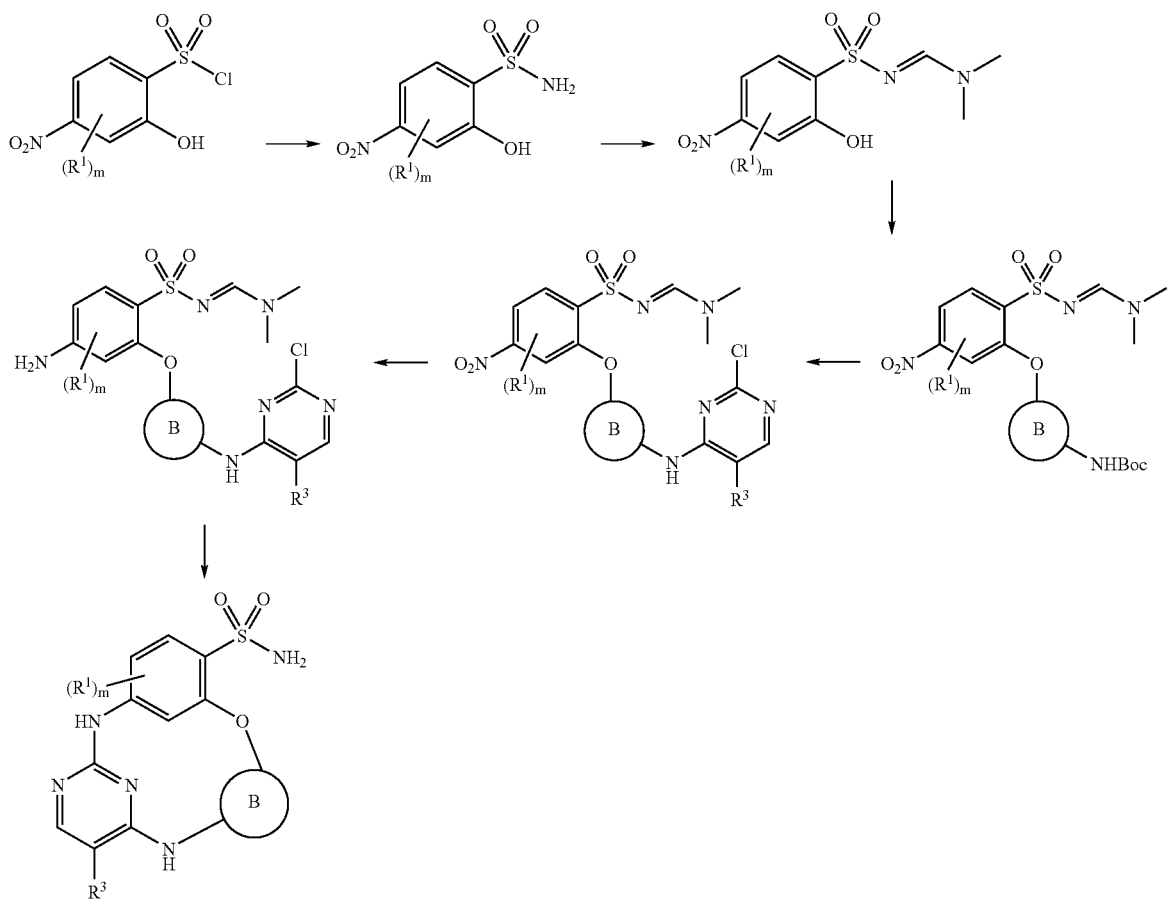

In the general formulas, $R^1$, $R^3$, B and m have the meaning that is indicated under general formula I.

EXAMPLE 8.2

Production of (S)-1[5]-Bromo-8-(hydroxymethyl)-4-oxa-2,9-diaza-1(2,4)-pyrimidina-3(1,3)-benzenacyclononaphane-3(4)-sulfonamide

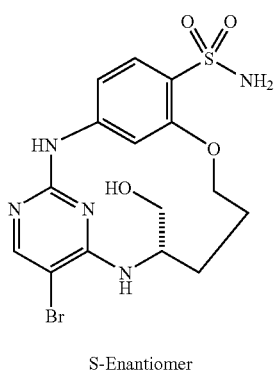

S-Enantiomer

A solution of 90 mg (0.17 mmol) of (S)-4-amino-2-[4-(5-bromo-2-chloro-pyrimidin-4-ylamino)-5-hydroxy-pentyloxy]-N-dimethylaminomethylene-benzenesulfonamide in acetonitrile/MeOH/water (8 ml/2 ml/1 ml) is added via a spray pump within 2.5 hours to a refluxing solution of acetonitrile/water/4 molar solution of hydrochloric acid in dioxane (45 ml/5 mr/0.6 ml). After another 16 hours under reflux, the reaction mixture is concentrated by evaporation in a rotary evaporator. The batch is made basic with saturated NaHCO$_3$ solution and extracted with ethyl acetate (2×). The combined organic phases are dried (Na$_2$SO$_4$), filtered and concentrated by evaporation. The remaining residue is digested with tert-butyl methyl ether. 62 mg (0.14 mmol, corresponding to 83% of theory) of the S-enantiomer product is obtained.

$^1$H-NMR (DMSO): 9.79 (s, 1H), 8.53 (br, 1H), 8.11 (s, 1H), 7.52 (m, 1H), 6.83 (s, 2H), 6.68 (m, 1H), 6.43 (d, 1H), 4.98 (t, 1H), 4.60 (m, 1H), 4.12 (m, 1H), 3.81 (m, 1H), 3.62 (m, 2H), 2.18 (m, 1H), 2.02 (m, 1H), 1.64 (m, 2H). MS: 444 (ES).

The R-enantiomer can be produced analogously to the instructions above, whereby (R)-4-amino-2-[4-(5-bromo-2-chloro-pyrimidin-4-ylamino)-5-hydroxy-pentyloxy]-N-dimethylaminomethylene-benzenesulfonamide should be used as a starting product.

Production of the Intermediate Products According to Process Variant 8b)

8c) Production of N-tert-Butyl-2-methoxy-4-nitro-benzenesulfonamide

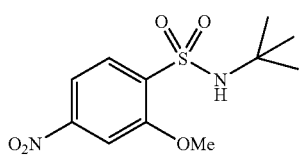

A solution of 5.0 g (19.9 mmol) of 2-methoxy-4-nitro-benzenesulfonyl chloride in acetone/water (60 ml/15 ml) is mixed at room temperature with 2.9 ml of triethylamine and 2.2 ml of tert.-butylamine. After 5 hours, the acetone is drawn off, and the residue is extracted from ethyl acetate. The combined organic phases are washed with dilute HCl solution and saturated NaCl solution and then filtered through a Whatman filter and concentrated by evaporation. The crude product that is obtained is recrystallized from ethyl acetate. 4.2 g (14.6 mmol, corresponding to 73% of theory) of the product is obtained.

$^1$H-NMR (DMSO): 8.03 (m, 1H), 7.95 (m, 2H), 7.48 (s, 1H), 4.05 (s, 3H), 1.08 (s, 9H).

8d) Production of 2-Methoxy-4-nitro-benzenesulfonamide

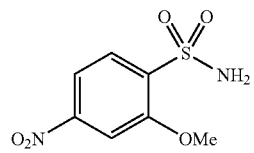

8.1 g (28.1 mmol) of N-tert-butyl-2-methoxy-4-nitro-benzenesulfonamide is mixed with 350 ml of trifluoroacetic acid and stirred for 20 hours at room temperature. The trifluoroacetic acid is drawn off, and the remaining residue is then digested with ethyl acetate. 5.0 g (21.6 mmol, corresponding to 77% of theory) of the product is obtained. The ethyl acetate phase is concentrated by evaporation, and the residue that is obtained is purified by chromatography (DCM/EtOH 95:5, Flashmaster II). Another 0.84 g (3.6 mmol, corresponding to 13% of theory) of the product is obtained.

$^1$H-NMR (DMSO): 7.95 (m, 3H), 7.45 (s, 2H), 4.03 (s, 3H). MS: 233 (ES).

8e) Production of N-Dimethylaminomethylene-2-methoxy-4-nitro-benzenesulfonamide

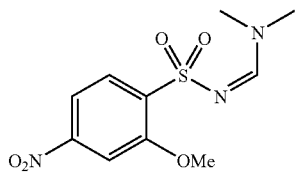

A solution of 5.0 g (21.5 mmol) of 2-methoxy-4-nitro-benzenesulfonamide in 15 ml of DMF is mixed at room temperature with 3.5 ml of N,N-dimethylformamide dimethyl acetal and stirred for 2.5 hours. The batch is added to a 5% KHSO$_4$ solution in ice water and then extracted from ethyl acetate. The combined organic phases are dried (MgSO$_4$), filtered and concentrated by evaporation. The crude product that is obtained is digested with ethyl acetate. 5.6 g (19.4 mmol, corresponding to 90% of theory) of the product is obtained.

$^1$H-NMR (DMSO): 8.29 (s, 1H), 8.04 (m, 1H), 7.90 (m, 2H), 3.99 (s, 3H), 3.24 (s, 3H), 2.93 (s, 3H). MS: 288 (ES).

8f) Production of N-Dimethylaminomethylene-2-hydroxy-4-nitro-benzenesulfonamide

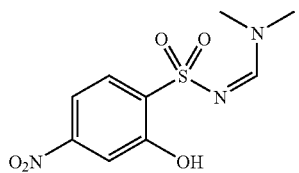

A solution of 2.82 g (9.8 mmol) of N-dimethylaminomethylene-2-methoxy-4-nitro-benzenesulfonamide in 70 ml of DCM is mixed slowly at room temperature with 13 ml of a 1 molar solution of boron tribromide in DCM. After 5 hours, 3 ml of the 1 molar solution of boron tribromide in DCM is added again, and it is stirred for another 16 hours. The batch is mixed with MeOH and diisopropyl ether. The precipitate that is formed is suctioned off, washed with EtOH and diisopropyl ether and dried. 1.94 g (7.1 mmol, corresponding to 72% of theory) of the product is obtained.

$^1$H-NMR (DMSO): 11.55 (s, 1H), 8.21 (s, 1H), 7.95 (m, 1H), 7.70 (m, 2H), 3.19 (s, 3H), 2.91 (s, 3H). MS: 274 (ES).

8g) Production of (S)-{4-[2-(Dimethylaminomethylene-sulfamoyl)-5-nitro-phenoxy]-1-hydroxymethyl-butyl}-carbamic acid-tert-butyl ester

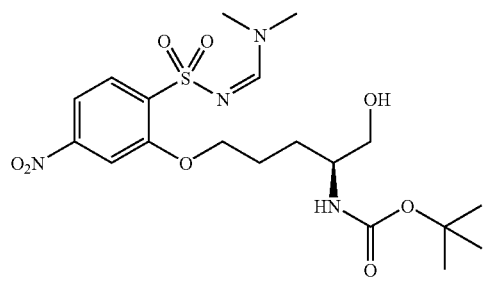

A solution of 1.20 g (6.9 mmol) of DEAD in 10 ml of THF is added in drops to a reaction mixture of 1.57 g (5.75 mmol) of N-dimethylaminomethylene-2-hydroxy-4-nitro-benzenesulfonamide, 1.26 g (5.75 mmol) of (S)-2-boc-amino-pentane-diol and 1.80 g (6.9 mmol) of triphenylphosphine in 30 ml of THF at 0° C. After 24 hours, first another 0.20 g (1.1 mmol) of DEAD is added. After 5 hours, it is also mixed again with 0.28 g (1.1 mmol) of triphenylphosphine and stirred for 68 hours. Finally, 0.2 g (1.1 mmol) of DEAD is added, and it is stirred for another 22 hours. The batch is concentrated by evaporation, and the residue is purified by chromatography (DCM/EtOH 95:5, Flashmaster II). 0.71 g (1.50 mmol, corresponding to 26% of theory) of the product is obtained.

$^1$H-NMR (DMSO): 8.21 (s, 1H), 8.03 (m, 1H), 7.88 (m, 2H), 6.60 (d, 1H), 4.65 (t, 1H), 4.19 (m, 2H), 3.42 (m, 3H), 3.22 (s, 3H), 2.93 (s, 3H), 1.73 (m, 4H), 1.39 (s, 9H). MS: 475 (ES).

8h) Production of 2-[4-(5-Bromo-2-chloro-pyrimidin-4-ylamino)-5-hydroxy-pentyloxy]-N-dimethylaminomethylene-4-nitro-benzenesulfonamide

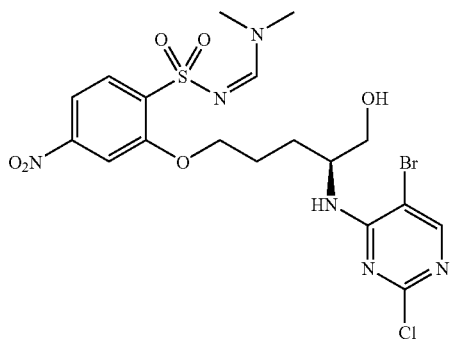

A solution of 212 mg (0.45 mmol) of (S)-{4-[2-(dimethylaminomethylene-sulfamoyl)-5-nitro-phenoxy]-1-hydroxymethyl-butyl}-carbamic acid-tert-butyl ester in 5 ml of acetonitrile is mixed at room temperature with 0.75 ml of a 4 molar solution of hydrochloric acid in dioxane. After 4 hours, the batch is concentrated by evaporation, and 2-(4-amino-5-hydroxy-pentyloxy)-N-dimethylaminomethylene-4-nitro-benzenesulfonamide is obtained in the form of hydrochloride.

A solution of the product that is obtained in 4 ml of acetonitrile is then mixed at room temperature with 110 mg (0.48 mmol) of 5-bromo-2,4-dichloro-pyrimidine in 4 ml of acetonitrile. 0.13 ml of triethylamine is added, and it is stirred overnight. The batch is concentrated by evaporation, and the residue is purified by chromatography (DCM/EtOH 95:5, Flashmaster II). 152 mg (0.27 mmol, corresponding to 60% of theory) of the product is obtained.

$^1$H-NMR (DMSO): 8.28 (s, 1H), 8.19 (s, 1H), 8.04 (m, 1H), 7.89 (m, 2H), 7.18 (d, 1H), 4.89 (t, 1H), 4.21 (m, 3H), 3.51 (m, 2H), 3.19 (s, 3H), 2.89 (s, 3H), 1.78 (m, 4H). MS: 565 (ES).

8i) Production of (S)-4-Amino-2-[4-(5-bromo-2-chloro-pyrimidin-4-ylamino)-5-hydroxy-pentyloxy]-N-dimethylaminomethylene-benzenesulfonamide

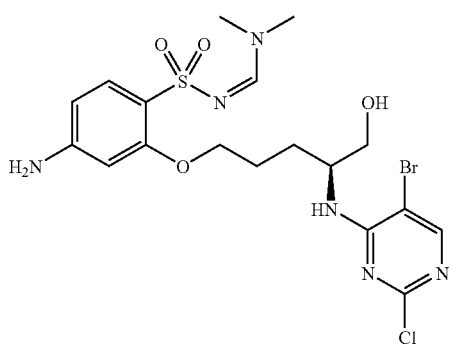

A solution of 145 mg (0.30 mmol) of 2-[4-(5-bromo-2-chloro-pyrimidin-4-ylamino)-5-hydroxy-pentyloxy]-N- dimethylaminomethylene-4-nitro-benzenesulfonamide in 20 ml of THF is mixed under argon at room temperature with 2.0 ml of an approximately 10% solution of Ti(III)Cl in 20-30% hydrochloric acid. After 2 hours, the reaction solution is mixed again with 0.3 ml of Ti(III)Cl solution, and it is stirred for another 18 hours. The batch is diluted with ethyl acetate and made basic with 1N NaOH solution. The phases are separated, and the aqueous phase is extracted again from ethyl acetate. The combined organic phases are dried ($Na_2SO_4$), filtered and concentrated by evaporation. The remaining residue is purified by chromatography (DCM/methanol 9:1; Flashmaster II). 90 mg (0.17 mmol, corresponding to 56% of theory) of the product is obtained.

$^1$H-NMR (DMSO): 8.28 (s, 1H), 8.06 (s, 1H), 7.39 (m, 1H), 7.17 (d, 1H), 6.11 (m, 2H), 5.79 (s, 2H), 4.89 (t, 1H), 4.20 (m, 1H), 3.88 (m, 2H), 3.51 (m, 2H), 3.11 (s, 3H), 2.85 (s, 3H), 1.75 (m, 4H). MS: 535 (ES).

A solution of 145 mg (0.41 mmol) of [3-(2-amino-phenoxy)-propyl]-(5-bromo-2-chloro-pyrimidin-4-yl)-amine in acetonitrile (10 ml) is added via a spray pump within 3 hours to a refluxing solution of acetonitrile/water/4 molar solution of hydrochloric acid in dioxane (45 ml/5 ml/0.6 ml). After the addition is completed, the reaction solution is stirred under reflux for another 16 hours. The batch is concentrated by evaporation, and the residue is purified by chromatography (DCM/EtOH 95:5; Flashmaster II). 81 mg (0.25 mmol, corresponding to 61% of theory) of the product is obtained.

$^1$H-NMR (DMSO): 9.21 (s, 1H), 8.02 (s, 1H), 7.78 (br, 1H), 7.07 (m, 3H), 6.86 (m, 1H), 4.22 (m, 2H), 3.30 (m, 2H), 1.79 (m, 2H). MS: 321 (ES).

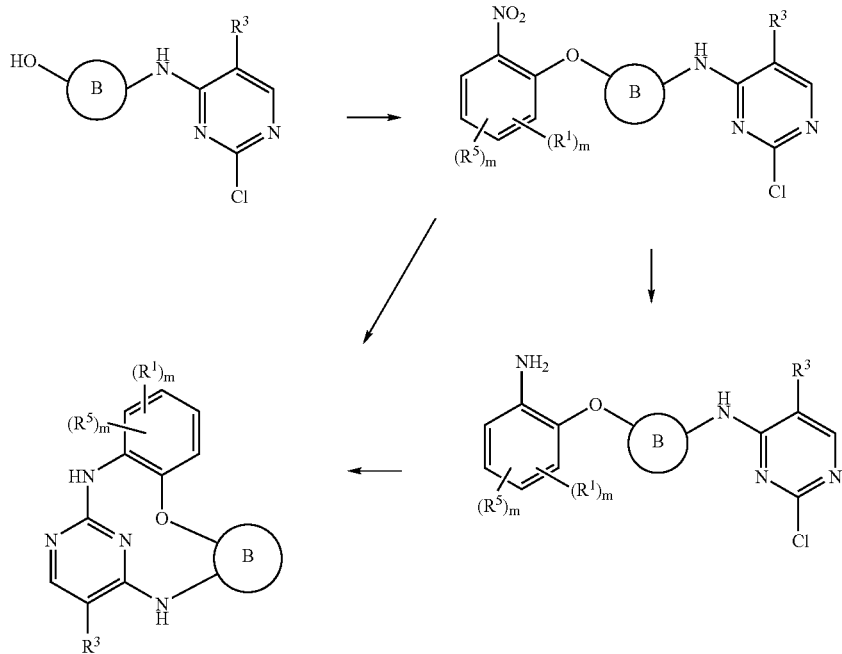

In the general formulas, $R^1$, $R^3$, $R^5$, B and m have the meaning that is indicated under general formula I.

EXAMPLE 8.3

Production of 1$^5$-Bromo-4-oxa-2,8-diaza-1(2,4)-pyrimidina-3(1,2)-benzenacyclooctaphane

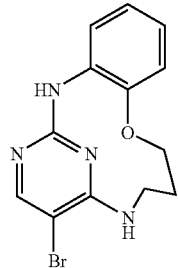

Production of the Intermediate Products According to Process Variant 8c

8j) Production of (5-Bromo-2-chloro-pyrimidin-4-yl)-[3-(2-nitro-phenoxy)-propyl]-amine

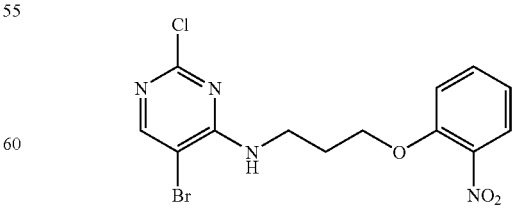

A solution of 1.06 g (4.0 mmol) of 3-(5-bromo-2-chloro-pyrimidin-4-ylamino)-propan-1-ol, 0.65 g (4.8 mmol) of 2-nitro-phenol and 1.25 g (4.8 mmol) of triphenylphosphine in 30 ml of THF is mixed under argon at 0° C. with 0.8 ml of DEAD. The reaction mixture is heated to room temperature while being stirred. After 20 hours, the batch is spun in, and the residue is purified by chromatography (hexane/ethyl acetate 3:1, Flashmaster II). 1.15 g (3.0 mmol, corresponding to 74% of theory) of the product is obtained.

$^1$H-NMR (DMSO): 8.22 (s, 1H), 7.88 (m, 2H), 7.63 (m, 1H), 7.33 (m, 1H), 7.09 (m, 1H), 4.21 (m, 2H), 3.54 (m, 2H), 2.03 (m, 2H). MS: 387 (ES).

8k) Production of [3-(2-Amino-phenoxy)-propyl]-(5-bromo-2-chloro-pyrimidin-4-yl)-amine

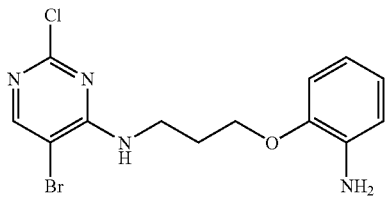

A solution of 500 mg (1.29 mmol) of (5-bromo-2-chloro-pyrimidin-4-yl)-[3-(2-nitro-phenoxy)-propyl]-amine in 20 ml of THF is mixed at room temperature with 6.0 ml of an approximately 10% solution of Ti(III)Cl in 20-30% hydrochloric acid. After 21 hours, another 2.0 ml of the Ti(III)Cl solution is added. Renewed additions of the Ti(III)Cl solution are carried out after 4 hours (3.0 ml) or 16 hours (4.0 ml). After another 6 hours, the batch is diluted with ethyl acetate and made basic with 1N NaOH solution. It is filtered on Celite, and the filter cake is washed with ethyl acetate. The organic phase is separated, dried (Na$_2$SO$_4$), filtered and concentrated by evaporation. The residue that is obtained is purified by chromatography (hexane/ethyl acetate 7:3). 290 mg (0.81 mmol, corresponding to 62% of theory) of the product is obtained.

$^1$H-NMR (DMSO): 8.25 (s, 1H), 7.83 (t, 1H), 6.78 (m, 1H), 6.63 (m, 2H), 6.49 (m, 1H), 4.69 (s, 2H), 3.96 (m, 2H), 3.58 (m, 2H), 2.03 (m, 2H). MS: 357 (ES).

Example 8.4

Production of 1$^5$-Bromo-4-oxa-2,8-diaza-1(2,4)-pyrimidina-3(1,2)-benzenacyclooctaphane-3$^4$-sulfonamide

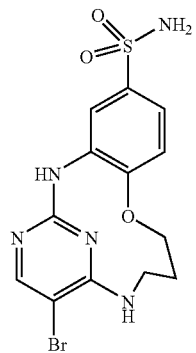

A solution of 200 mg (0.42 mmol) of 4-[3-(5-bromo-2-chloro-pyrimidin-4-ylamino)-propoxy]-3-nitro-benzenesulfonamide in 14 ml of THF is mixed with 3 ml of an approximately 10% solution of Ti(III)Cl in 20-30% hydrochloric acid, and it is stirred for 19 hours at room temperature. According to TLC monitoring, during the course of 184 hours, altogether another 9 ml of the Ti(III)Cl solution is added in portions. The batch is made basic with 2N NaOH solution and extracted from ethyl acetate. The combined organic phases are dried (Na$_2$SO$_4$), filtered and concentrated by evaporation. The residue that is obtained is purified by chromatography (DCM/EtOH 95:5). 62 mg (0.14 mmol, corresponding to 33% of theory) of the product is obtained.

The product that is obtained is dissolved in 5 ml of acetonitrile and added via a spray pump within 2 hours to a refluxing solution of acetonitrile/water/4 molar solution of hydrochloric acid in dioxane (30 ml/3 ml/0.4 ml). Then, the batch is stirred under reflux for another 16 hours. After cooling, the precipitate that is formed is suctioned off and washed with acetonitrile and water. 13 mg (0.03 mmol, corresponding to 8% of theory) of the product is obtained.

$^1$H-NMR (DMSO): 10.53 (s, 1H), 8.97 (m, 1H), 8.25 (s, 1H), 7.67 (m, 2H), 7.30 (m, 3H), 4.31 (m, 2H), 3.35 (m, 2H), 1.88 (m, 2H). MS: 400 (ES).

Production of Intermediate Products 8l) 4-[3-(5-Bromo-2-chloro-pyrimidin-4-ylamino)-propoxy]-3-nitro-benzenesulfonamide

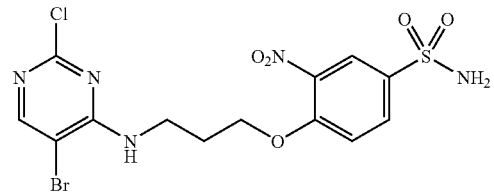

398 mg (1.02 mmol) of (5-bromo-2-chloro-pyrimidin-4-yl)-[3-(2-nitro-phenoxy)-propyl]-amine is added in portions to 4 ml of ice-cooled chlorosulfonic acid. The batch is stirred for 2.5 hours, and the reaction mixture is then carefully added in drops to ice. The solid that is formed is suctioned off, washed with water and dried. The crude product that is obtained is dissolved in 20 ml of acetone, mixed with 3 ml of ammonia (33%) and stirred for one hour at room temperature. The batch is concentrated by evaporation, mixed with ethyl acetate and washed with water. The combined organic phases are filtered through a Whatman filter and concentrated by evaporation. 223 mg (0.48 mmol, corresponding to 47% of theory) of the product is obtained.

$^1$H-NMR (DMSO): 8.29 (m, 1H), 8.24 (s, 1H), 8.02 (m, 1H), 7.85 (t, 1H), 7.47 (m, 3H), 4.29 (t, 2H), 3.55 (m, 2H), 2.04 (m, 2H). MS: 466 (ES).

Production of the Amide Derivatives

Process Variant 9

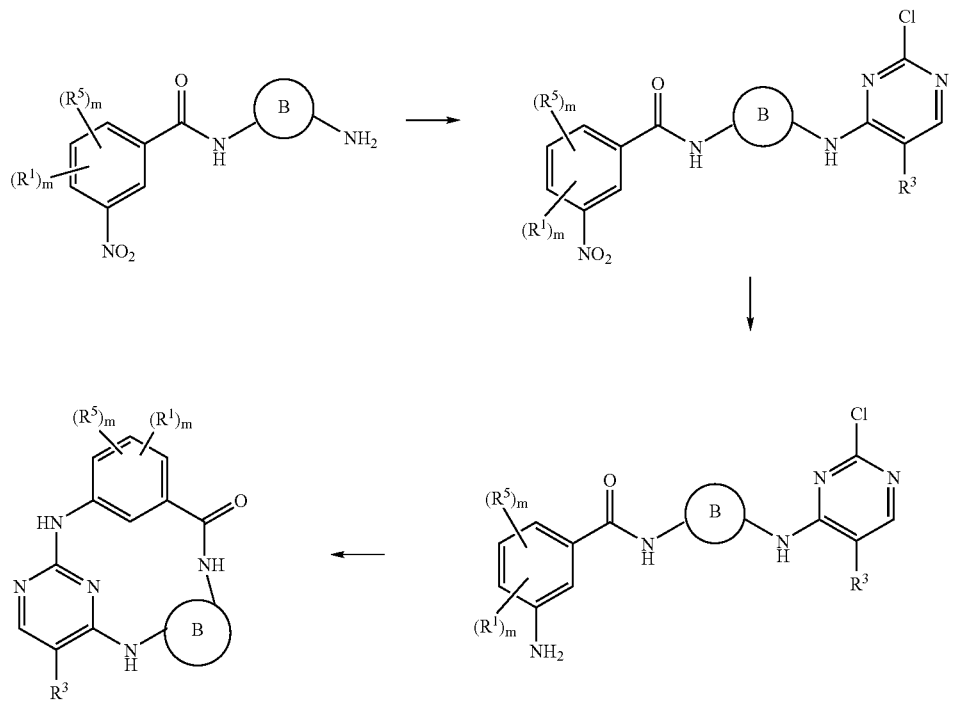

In general formulas, $R^1$, $R^3$, $R^5$, B and m have the meaning that is indicated under general formula I.

EXAMPLE 9.0

Production of $1^5$-Bromo-2,5,10-triaza-1(2,4)-pyrimidina-3 (1,3)-benzenacyclodecaphan-4-one

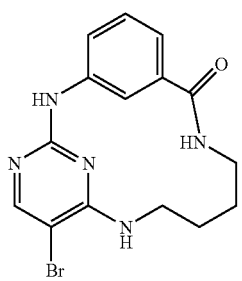

A solution of 440 mg (1.1 mmol) of 3-amino-N-[4-(5-bromo-2-chloro-pyrimidin-4-ylamino)-butyl]-benzamide in acetonitrile/DMF/water (25 ml/5 ml/5 ml) is added via a dropping funnel within 2 hours to a refluxing solution of acetonitrile/water/4 molar solution of hydrochloric acid in dioxane (150 ml/10 ml/2 ml). After another 3 hours under reflux, the batch is taken from the oil bath. The precipitate that is formed after cooling is suctioned off and washed with water and diisopropyl ether. 38 mg (0.10 mmol, corresponding to 9% of theory) of the product is obtained.

$^1$H-NMR (DMSO): 10.45 (s, 1H), 8.40 (m, 3H), 8.25 (s, 1H), 7.40 (m, 3H), 3.35 (m, 2H), 3.10 (m, 2H), 1.48 (m, 4H). MS: 363 (ES).

Production of the Intermediate Products According to Process Variant 9

9a) Production of N-(4-Amino-butyl)-3-nitro-benzamide

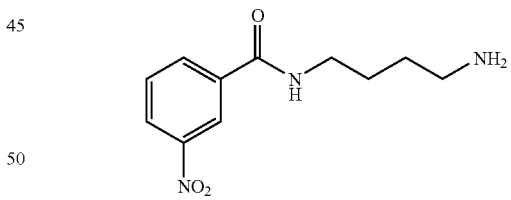

2.27 g (6.72 mmol) of [4-(3-nitro-benzoylamino)-butyl]-carbamic acid-tert-butyl ester is mixed with 9 ml of trifluoroacetic acid and stirred for 3 hours at room temperature. The batch is carefully added to 2N NaOH solution and then extracted from ethyl acetate. The combined organic phases are filtered through a Whatman filter and concentrated by evaporation. The crude product that is obtained is recrystallized from ethanol/diisopropyl ether. 519 mg (2.19 mmol, corresponding to 33% of theory) of the product is obtained.

$^1$H-NMR (DMSO): 8.95 (m, 1H), 8.65 (s, 1H), 8.86 (m, 1H), 8.78 (m, 1H), 7.72 (m, 1H), 3.30 (m, 2H), 3.04 (m, 2H), 1.55 (m, 2H), 1.40 (m, 2H). MS: 238 (ES).

9b) Production of N-[4-(5-Bromo-2-chloro-pyrimidin-4-ylamino)-butyl]-3-nitro-benzamide

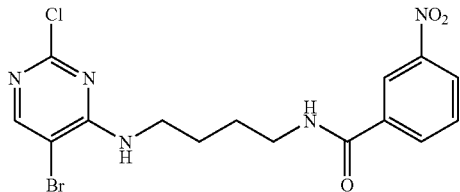

A solution of 502 mg (2.2 mmol) of 5-bromo-2,4-dichloro-pyrimidine and 0.4 ml of triethylamine (2.3 mmol) in 2.5 ml of acetonitrile is mixed at 0° C. while being stirred with 547 mg (2.3 mmol) of N-(4-amino-butyl)-3-nitro-benzamide. The batch is stirred overnight at room temperature. The precipitate that is formed is suctioned off, washed with water and dried. 574 mg (1.3 mmol, corresponding to 61% of theory) of the product is obtained.

$^1$H-NMR (DMSO): 8.87 (t, 1H), 8.65 (m, 1H), 8.38 (m, 1H), 8.28 (m, 1H), 8.18 (s, 1H), 7.76 (m, 2H), 3.35 (m, 4H), 1.55 (m, 4H). MS: 427 (EI).

9c) Production of 3-Amino-N-[4-(5-bromo-2-chloro-pyrimidin-4-ylamino)-butyl]-benzamide

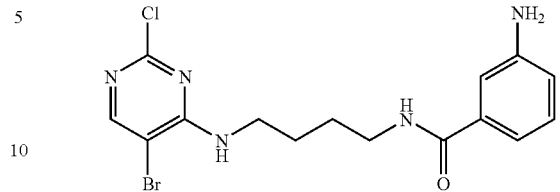

A solution of 568 mg (1.32 mmol) of N-[4-(5-bromo-2-chloro-pyrimidin-4-ylamino)-butyl]-3-nitro-benzamide in 15 ml of THF is mixed at room temperature with 9 ml of a 15% solution of Ti(III)Cl in approximately 10% hydrochloric acid. After 21 hours, the batch is made basic with 2N NaOH solution, mixed with ethyl acetate and filtered on Celite. The filter cake is rewashed with ethyl acetate. The organic phase of the filtrate is filtered through a Whatman filter and concentrated by evaporation. 447 mg (1.12 mmol, corresponding to 85% of theory) of the product is obtained.

MS: 398 (ES).

Production of Urea Derivatives

Process Variant 10

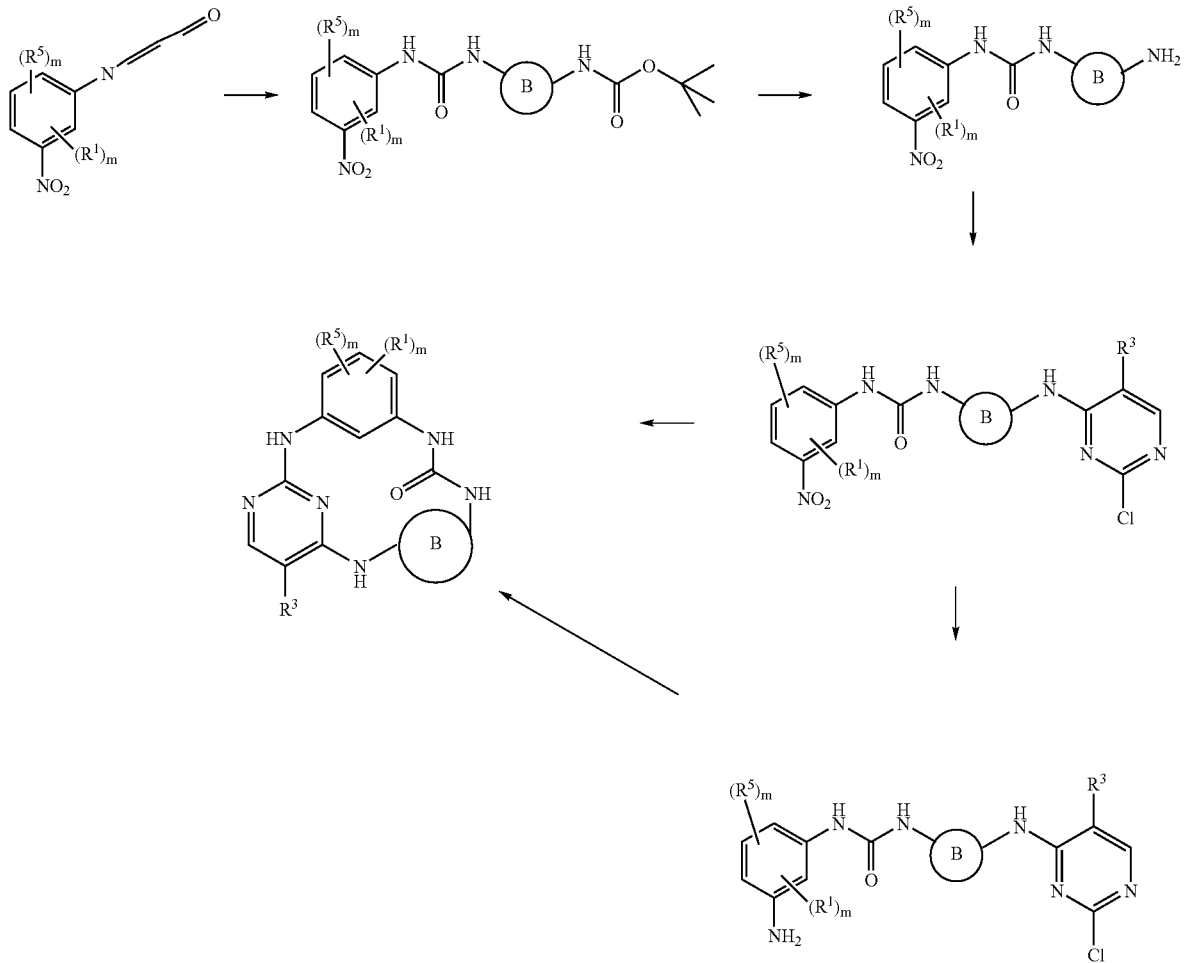

In the general formulas, $R^1$, $R^3$, $R^5$, B and m have the meaning that is indicated under general formula I.

EXAMPLE 10.0

Production of $1^5$-Bromo-2,4,6,10-tetraaza-1(2,4)-pyrimidina-3(1,3)-benzenacyclodecaphan-5-one

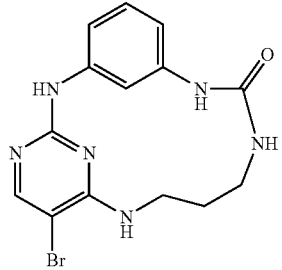

A solution of 265 mg (0.66 mmol) of 1-(3-amino-phenyl)-3-[3-(5-bromo-2-chloro-pyrimidin-4-ylamino)-propyl]-urea in acetonitrile/dioxane/water (8 ml/1 ml/1 ml) is added via a spray pump within 2 hours to a refluxing solution of acetonitrile/water/4 molar solution of hydrochloric acid in dioxane (70 ml/5 ml/1 ml). After another 18 hours under reflux, the batch is made basic with 2N NaOH after cooling and extracted from ethyl acetate. The combined organic phases are filtered through a Whatman filter and concentrated by evaporation. The residue that is obtained is purified by chromatography (DCM/EtOH 9:1). The crude product that is obtained is then recrystallized from MeOH. 7 mg (0.02 mmol, corresponding to 3% of theory) of the product is obtained.

$^1$H-NMR (DMSO): 9.31 (s, 1H), 8.79 (m, 1H), 8.17 (s, 1H), 7.98 (s, 1H), 7.27 (t, 1H), 7.05 (t, 1H), 6.72 (m, 1H), 651 (m, 1H), 6.43 (m, 1H), 3.48 (m, 2H), 3.14/m, 2H), 1.65 (m, 2H). $^{13}$C-NMR (DMSO): 158.6s, 157.8d, 156.1s, 155.5s, 141.6s, 140.9s, 129.0d, 112.7d, 112.2d, 110.3d, 92.1s, 38.3t, 36.3t, 30.3t. MS: 363 (ES).

Production of Intermediate Products According to Process Variant 10

10a) Production of {3-[3-(3-Nitro-phenyl)-ureido]-propyl}-carbamic Acid-tert-butyl ester

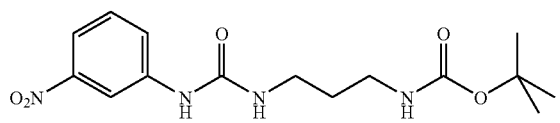

A solution of 3.35 g (19.2 mmol) of N-boc-1,3-diaminopropane in 50 ml of EtOH is mixed at 0° C. in portions with 3.15 g (19.2 mmol) of 3-nitrophenyl isocyanate. The batch is stirred overnight at room temperature and then concentrated by evaporation in a rotary evaporator. It is mixed with DCM and washed with water. The organic phase is filtered through a Whatman filter and concentrated by evaporation. 6.4 g (18.9 mmol, corresponding to 98% of theory) of the product is obtained.

$^1$H-NMR (DMSO): 9.11 (s, 1H), 8.48 (m, 1H), 7.71 (m, 1H), 7.65 (m, 1H), 7.48 (t, 1H), 6.82 (t, 1H), 6.32 (t, 1H), 3.12 (m, 2H), 2.95 (m, 2H), 1.55 (m, 2H), 1.38 (s, 9H). MS: 339 (CI).

10b) Production of 1-(3-Amino-propyl)-3-(3-nitro-phenyl)-urea

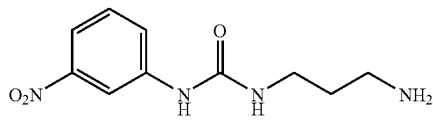

6.4 g (18.9 mmol) of {3-[3-(3-nitro-phenyl)-ureido]-propyl}-carbamic acid-tert-butyl ester is mixed with 22 ml of trifluoroacetic acid and stirred for 2 hours at room temperature. The solvent is drawn off, the batch is mixed with NaHCO$_3$ solution and extracted from ethyl acetate. The combined organic phases are filtered through a Whatman filter and concentrated by evaporation. 4.4 g (18.5 mmol, corresponding to 97% of theory) of the product is obtained.

$^1$H-NMR (DMSO): 9.46 (s, 1H), 8.55 (m, 1H), 7.75 (m, 1H), 7.65 (m, 1H), 7.48 (m, 1H), 6.88 (t, 1H), 3.30 (m, 2H), 2.75 (m, 2H), 1.72 (m, 2H). MS: 239 (ES).

10c) Production of 1-[3-(5-Bromo-2-chloro-pyrimidin-4-ylamino)-propyl]-3-(3-nitro-phenyl)-urea

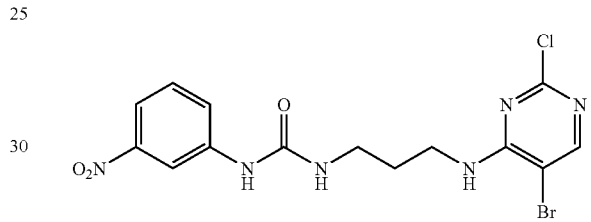

A solution of 1.6 g (6.7 mmol) of 1-(3-amino-propyl)-3-(3-nitro-phenyl)-urea in 30 ml of acetonitrile is mixed with a solution of 1.6 g (7.0 mmol) of 5-bromo-2,4-dichloro-pyrimidine in 10 ml of acetonitrile. 2.0 ml of triethylamine is added, and it is stirred for 90 minutes at room temperature. It is diluted with ethyl acetate (150 ml) and washed with citric acid (10%), saturated NaHCO$_3$ solution as well as saturated NaCl solution, dried (Na$_2$SO$_4$), filtered and concentrated by evaporation. The remaining residue is purified by chromatography (hexane/ethyl acetate 1:1). 1.7 g (4.0 mmol, corresponding to 60% of theory) of the product is obtained.

$^1$H-NMR (DMSO): 9.08 (s, 1H), 8.52 (m, 1H), 8.21 (s, 1H), 7.70 (m, 3H), 7.46 (t, 1H), 6.38 (t, 1H), 3.45 (m, 2H), 3.15 (m, 2H), 1.72 (m, 2H).

10d) Production of 1-(3-Amino-phenyl)-3-[3-(5-bromo-2-chloro-pyrimidin-4-ylamino)-propyl]-urea

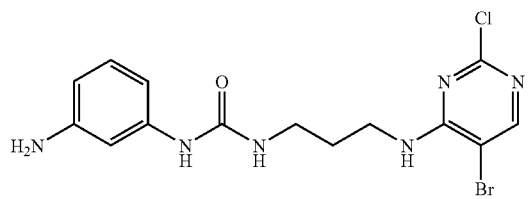

A solution of 1.71 g (3.98 mmol) of 1-[3-(5-bromo-2-chloro-pyrimidin-4-ylamino)-propyl]-3-(3-nitro-phenyl)-urea in 50 ml of THF is mixed at room temperature with 30 ml of a 15% solution of Ti(III)Cl in approximately 10% hydrochloric acid. After 24 hours, another 5 ml of the 15% solution of Ti(III)Cl in approximately 10% hydrochloric acid is added. After another 6 hours, the batch is made basic with 2N NaOH solution and extracted from ethyl acetate. The combined organic phases are filtered through a Whatman filter and concentrated by evaporation. The residue that is obtained is purified by chromatography (DCM/EtOH 9:1). 850 mg (2.13 mmol, corresponding to 54% of theory) of the product is obtained.

$^1$H-NMR (DMSO): 8.25 (s, 1H), 8.14 (s, 1H), 7.78 (t, 1H), 6.82 (t, 1H), 6.68 (m, 1H), 6.50 (m, 1H), 6.06 (m, 2H), 4.94 (s, 1H), 3.30 (m, 2H), 3.31 (m, 2H), 1.67 (m, 2H). MS: 399 (ES).

Ring Closure of Bifunctional Acyclic Precursors

Process Variant 11

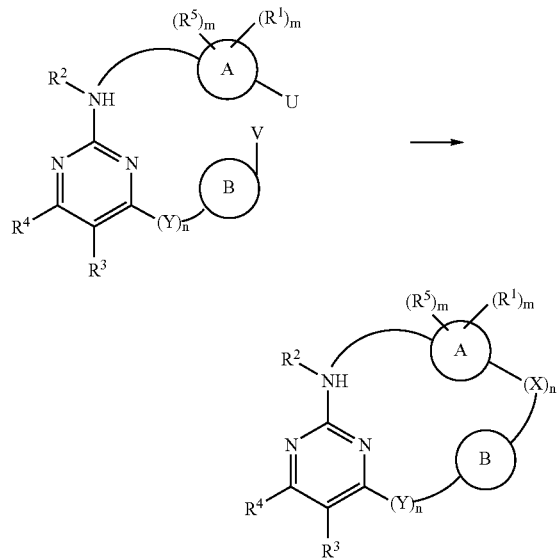

A, B, $R^1$, $R^2$, $R^3$, $R^4$, $R^5$, X, Y, m and n have the meanings that are indicated under general formula I. U and V stand for groups such as —OH, —CO$_2$H, —CO$_2$—C1-C$_6$-alkyl, —SO$_2$Cl, —SO$_2$F, —SO$_3$H, etc.

The ring closure or the synthesis of the macrocyclic compounds can also be performed analogously to known methods ((a) Roxburgh, C. J. *Tetrahedron* 1995, 51, 9767. (b) Meng, Q. *Top. Curr. Chem.* 1991, 161, 107. (c) Paterson, I. *Tetrahedron* 1985, 41, 3569. (d) Masamune, S. *Angew. Chem.* 1977, 89, 602. (e) Nicolaou, K. C. *Tetrahedron* 1977, 33, 683. (f) Ruggli, P. Liebigs Ann. Chem. 1912, 92.)

Ring Closure by Mitsunobu Reaction

Process Variant 12

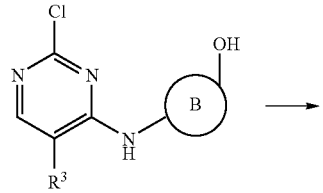

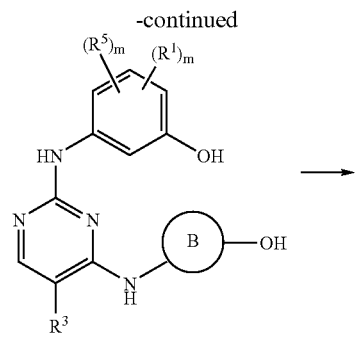

-continued

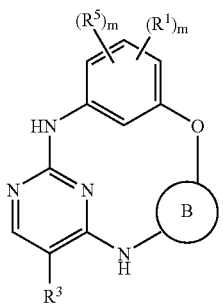

In the general formulas, $R^1$, $R^3$, $R^5$, B and m have the meaning that is indicated under general formula I.

Synthesis of macrocyclic compounds with use of the Mitsunobu reaction is generally known and can be looked up in (a) Xue, C.-B. *J. Med. Chem.* 2001, 44, 2636. (b) Steggich, W. *Tet. Lett.* 1991, 32, 5781. (c) Mitsunobu, O. *Synthesis* 1981, 1.

EXAMPLE 12.0

Production of 1$^5$-Bromo-4-oxa-2,9-diaza-1(2,4)-pyrimidina-3(1,3)-benzen-acyclononaphane

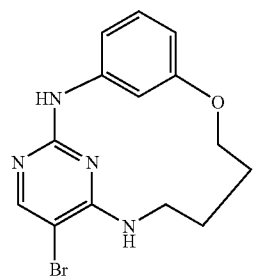

A solution of 108 mg (0.31 mmol) of 3-[5-bromo-4-(4-hydroxy-butylamino)-pyrimidin-2-ylamino]-phenol in THF/N-methylmorpholine (9 ml/1 ml) is added while being stirred within 3 hours to a mixture of 710 mg (2.7 mmol) of triphenylphosphine and 481 mg (2.8 mmol) of DEAD in 100 ml of THF at 40° C. After another 30 minutes, the reaction mixture is concentrated by evaporation in a rotary evaporator. After water is added, it is extracted with ethyl acetate (2×). The combined organic phases are dried (Na$_2$SO$_4$), filtered and concentrated by evaporation. The residue that is formed is purified by chromatography (dichloromethane/methanol 9:1), and the crude product that is obtained is then digested with isopropyl ether. 17 mg (0.05 mmol, corresponding to 17% of theory) of the product is obtained.

$^1$H-NMR (DMSO): 9.18 (s, 1H), 9.08 (s, 1H), 8.04 (s, 1H), 7.20 (s, 1H), 7.09 (dd, 1H), 6.96 (t, 1H), 6.31 (dd, 1H), 3.30 (m, 4H), 1.90 (m, 4H). MS: 334 (EI).

Production of the Intermediate Products According to Process Variant 12

12a) Production of 4-(5-Bromo-2-chloro-pyrimidin-4-ylamino)-butan-1-ol

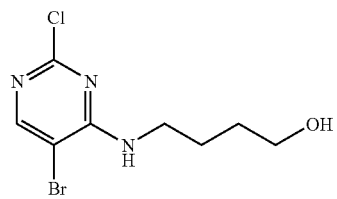

A solution of 2.28 g (10.0 mmol) of 5-bromo-2,4-dichloro-pyrimidine and 1.7 ml (12.0 mmol) of triethylamine in 10 ml of acetonitrile is mixed at 0° C. with 1.1 ml (12.0 mmol) of 4-amino-butanol. The reaction mixture is slowly heated to room temperature while being stirred by removal of the ice bath. After 16 hours, the precipitate that is formed is filtered off. The filtrate is completely concentrated by evaporation and digested with diisopropyl ether. 2.74 g (9.8 mmol, corresponding to 98% of theory) of the product is obtained.

$^1$H-NMR (DMSO): 8.19 (s, 1H), 7.72 (t, 1H), 4.45 (br, 1H), 3.38 (m, 4H), 1.56 (m, 2H), 1.45 (m, 2H). MS: 279 (EI).

12b) 3-[5-Bromo-4-(4-hydroxy-butylamino)-pyrimidin-2-ylamino]-phenol

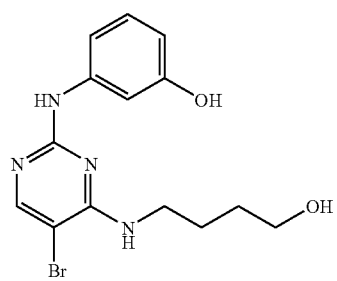

A reaction mixture of 327 mg (3.0 mmol) of 3-aminophenol and 864 mg (3.1 mmol) of 4-(5-bromo-2-chloro-pyrimidin-4-ylamino)-butan-1-ol in 9 ml of acetonitrile is mixed with 0.75 ml of a 4 M solution of hydrochloric acid in dioxane, and it is stirred under reflux overnight. After the cooling, the reaction mixture is filtered, and the filtrate is completely concentrated by evaporation. The oil that is obtained is recrystallized from ethyl acetate/ethanol. The solid is filtered off and then dissolved in water. By adding triethylamine, the solution is made basic and extracted with ethyl acetate (2×). The combined organic phases are dried (Na$_2$SO$_4$), filtered and concentrated by evaporation. 444 mg (1.2 mmol, corresponding to 40% of theory) of the product is obtained.

$^1$H-NMR (DMSO): 9.18 (s, 1H), 9.06 (s, 1H), 7.97 (s, 1H), 7.19 (m, 2H), 6.99 (m, 2H), 6.32 (m, 1H), 4.45 (t, 1H), 3.40 (m, 4H), 1.60 (m, 2H), 1.47 (m, 2H). MS: 352 (ES).

Ring Closure by Macrolactamization

Process Variant 13

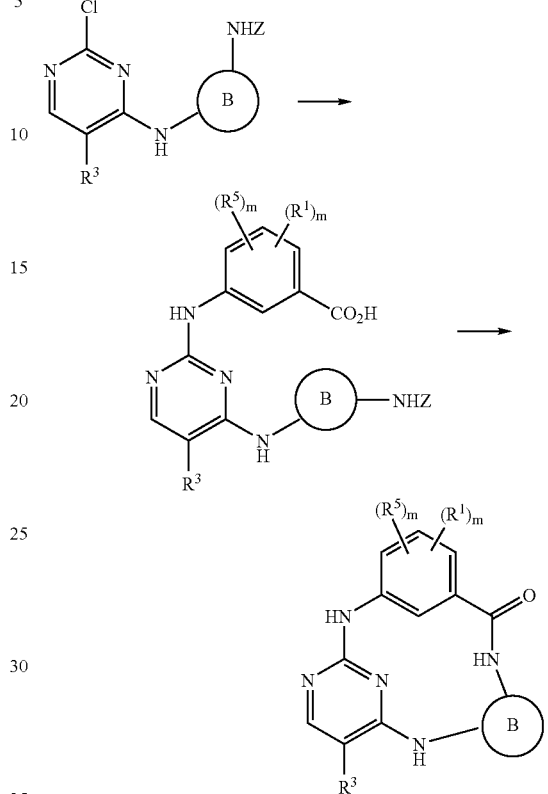

In the general formulas, R$^1$, R$^3$, R$^5$, B and m have the meaning that is indicated under general formula I and NHZ stands for the group

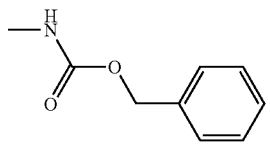

Synthesis of macrolactams is carried out according to standard processes ((a) Xue, C.-B. *J. Med. Chem.* 2001, 44, 2636. (b) Jackson, F. W. *J. Org. Chem.* 2002, 67, 4882).

EXAMPLE 13.0

Production of 1$^5$-Bromo-2,5,11-triaza-1(2,4)-pyrimidina-3(1,3)-benzenacycloundecaphane-4-one (A) and 2,5,11-Triaza-1(2,4)-pyrimidina-3(1,3)-benzenacycloundecaphane-4-one (B)

A

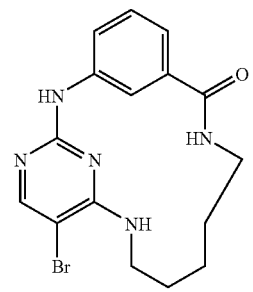

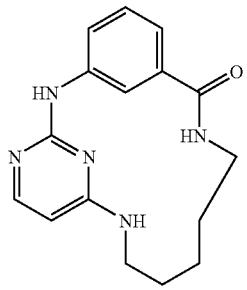

A solution of 300 mg (0.57 mmol) of 3-[4-(5-benzyloxy-carbonylamino-pentylamino)-5-bromo-pyrimidin-2-ylamino]-benzoic acid in methanol/dichloromethane (40 ml/5 ml) is mixed with 350 mg of Pd/C (10%) and hydrogenated for 150 minutes in a low-pressure apparatus. The reaction mixture is filtered on Celite and completely concentrated by evaporation. The remaining residue is dissolved in DMF/methanol/water (10.0 m/1.0 ml/0.2 ml) and added via a spray pump over 2 hours to a solution of 410 mg (2.2 mmol) of EDC, 330 mg (2.2 mmol) of HOBt and 0.25 ml of N-methylmorpholine in 200 ml of DMF. After 72 hours, the reaction mixture is concentrated by evaporation, mixed with water, and then extracted with ethyl acetate (2×). The combined organic phases are washed with water, dried (Na$_2$SO$_4$), filtered and concentrated by evaporation. The residue that is formed is purified by chromatography (dichloromethane/methanol 1:1). 35 mg (0.09 mmol, corresponding to 16% of theory) of 1$^5$-bromo-2,5,11-triaza-1(2, 4)-pyrimidina-3(1,3)-benzenacycloundecaphane-4-one (A) and 13 mg (0.04 mmol, corresponding to 7% of theory) of 2,5,11-triaza-1 (2,4)-pyrimidina-3 (1,3)-benzenacycloundecaphane-4-one (B) are obtained.

1$^5$-Bromo-2,5,11-triaza-1(2,4)-pyrimidina-3(1,3)-benzenacycloundecaphane-4-one (A):

$^1$H-NMR (DMSO): 9.45 (s, 1H), 8.81 (s, 1H), 8.12 (t, 1H), 7.98 (s, 1H), 7.20 (m, 4H), 3.30 (m, 4H), 1.78 (m, 2H), 1.60 (m, 2H), 1.30 (m, 2H). MS: 376 (ES).

2,5,11-Triaza-1(2,4)-pyrimidina-3 (1,3)-benzenacycloundecaphane-4-one (B):

$^1$H-NMR (DMSO): 9.21 (s, 1H), 8.97 (s, 1H), 8.10 (t, 1H), 7.72 (d, 1H), 7.38 (t, 1H), 7.25 (t, 1H), 7.18 (dd, 1H), 7.08 (dd, 1H), 5.84 (d, 1H), 3.30 (m, 2H), 3.17 (m, 2H), 1.75 (m, 2H), 1.53 (m, 2H), 1.30 (m, 2H). MS: 298 (ES).

Production of Intermediate Products According to Process Variant 13

13a) Production of [5-(5-Bromo-2-chloro-pyrimidin-4-ylamino)-pentyl]-carbamic acid-benzyl ester

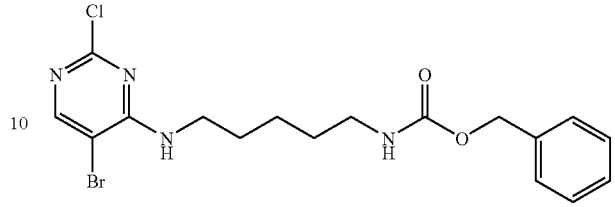

A solution of 860 mg (3.8 mmol) of 5-bromo-2,4-dichloro-pyrimidine and 1.2 ml (8.5 mmol) of triethylamine in 6 ml of acetonitrile is mixed at 0° C. with 1.0 g (3.7 mmol) of (5-amino-pentyl)-carbamic acid-benzyl ester. The reaction mixture is slowly heated to room temperature while being stirred by removal of the ice bath. After 60 hours, it is mixed with water and then extracted with ethyl acetate (2×). The combined organic phases are dried (Na$_2$SO$_4$), filtered and concentrated by evaporation. The residue that is formed is purified by chromatography (hexane/ethyl acetate 1:1). 1.2 g (2.8 mmol, corresponding to 77% of theory) of the product is obtained.

$^1$H-NMR (DMSO): 8.21 (s, 1H), 7.72 (t, 1H), 7.35 (m, 5H), 7.23 (t, 1H), 4.99 (s, 2H), 3.30 (m, 2H), 2.97 (m, 2H), 1.47 (m, 4H), 1.27 (m, 2H). MS: 427 (ES).

13b) Production of 3-[4-(5-Benzyloxycarbonylamino-pentylamino)-5-bromo-pyrimidin-2-ylamino]-benzoic Acid

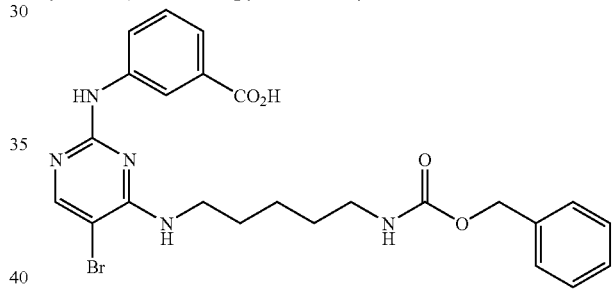

A reaction mixture of 1.20 g (2.8 mmol) of [5-(5-bromo-2-chloro-pynmidin-4-ylamino)-pentyl]-carbamic acid-benzyl ester and 0.37 g (2.7 mmol) of 3-aminobenzoic acid in acetonitrile/water (8 ml/1.5 ml) is stirred under reflux for 20 hours. The reaction mixture is spun in, and the remaining residue is purified by chromatography (dichloromethane/methanol 9:1, Flashmaster II). 1.27 g (2.4 mmol, corresponding to 86% of theory) of the product is obtained.

$^1$H-NMR (DMSO): 10.03 (s, 1H), 8.38 (s, 1H), 8.15 (s, 1H), 7.81 (m, 2H), 7.56 (d, 1H), 7.30 (m, 7H), 4.98 (s, 2H), 3.35 (m, 2H), 2.98 (m, 2H), 1.54 (m, 2H), 1.32 (m, 4H). MS: 528 (Cl).

Production of Aza-phane Derivatives

Process Variant 14

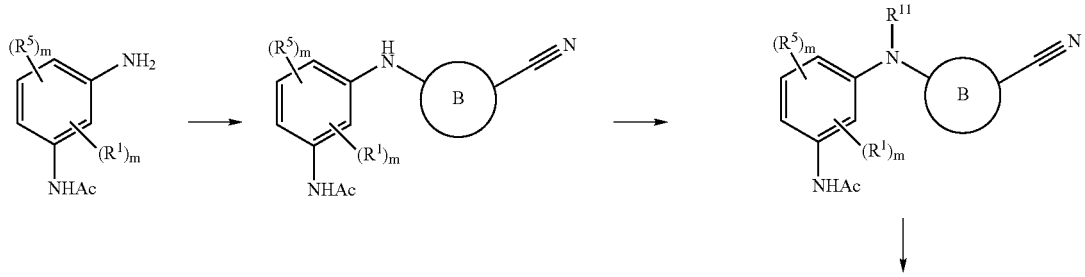

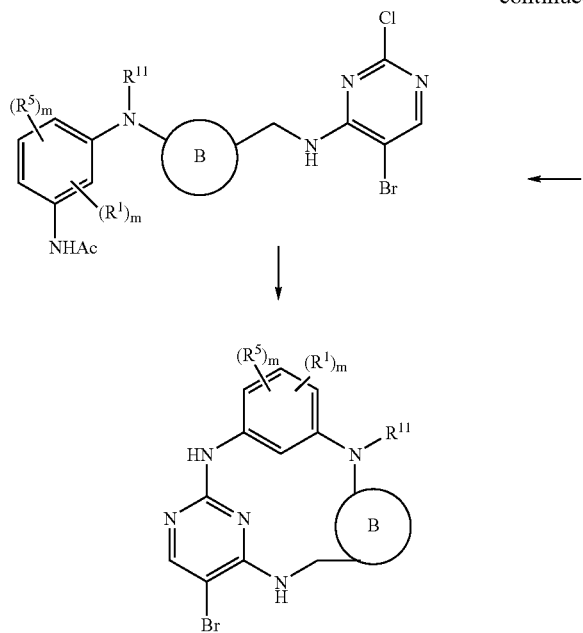

In the general formulas, $R^1$, $R^5$, $R^{11}$, B and m have the meaning that is indicated under general formula I.

EXAMPLE 14.0

Production of $1^5$-Bromo-4-mesyl-2,4,9-triaza-1(2,4)-pyrimidina-3(1,3)-benzenacyclononaphane

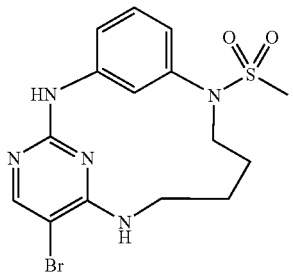

A solution of 160 mg (0.33 mmol) of N-(3-{[4-(5-bromo-2-chloro-pyrimidin-4-ylamino)-butyl]-methanesulfonyl-amino}-phenyl)-acetamide in 10 ml of acetonitrile is added via a spray pump within 3 hours to a refluxing solution of acetonitrile/water/4 molar solution of hydrochloric acid in dioxane (40 ml/10 ml/1 ml). After the addition is completed, the batch is stirred under reflux for another 16 hours, and then the organic solvent is drawn off. It is mixed with ethyl acetate and washed with dilute $NaHCO_3$ solution. The combined organic phases are concentrated by evaporation, and the residue that is obtained is washed with ethyl acetate, MeOH and water. After the drying, 81 mg (0.20 mmol, corresponding to 63% of theory) of the product is obtained.

$^1$H-NMR (DMSO): 9.38 (s, 1H), 8.16 (m, 1H), 7.97 (s, 1H), 7.23 (m, 2H), 6.99 (m, 1H), 6.92 (m, 1H), 3.64 (m, 2H), 3.16 (m, 2H), 3.06 (s, 3H), 1.77 (m, 2H), 1.60 (m, 2H). MS: 412 (ES).

Production of Intermediate Products

14a) N-(3-{[4-(5-Bromo-2-chloro-pyrimidin-4-ylamino)-butyl]-methanesulfonyl-amino}-phenyl)-acetamide

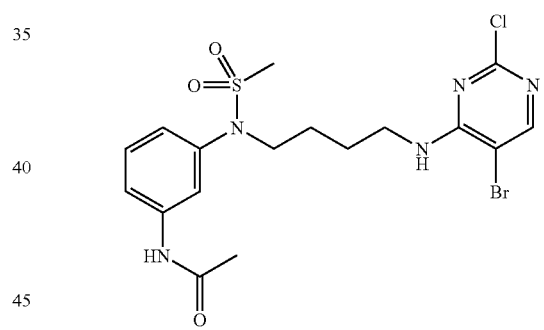

460 mg (1.56 mmol) of N-{3-[(3-cyano-propyl)-methanesulfonyl-amino]-phenyl}-acetamide in 25 ml of ethanol and 0.5 ml of concentrated HCl are hydrogenated with use of 60 mg (0.26 mmol) of platinum(IV)oxide for 5 hours at room temperature under normal pressure. The batch is filtered and concentrated by evaporation. The residue that is obtained is mixed with a solution of 355 mg (1.56 mmol) of 5-bromo-2,4-dichloro-pyrimidine in 15 ml of acetonitrile. 0.45 ml of triethylamine is added drop by drop, and it is stirred for 16 hours at room temperature. The batch is concentrated by evaporation, and the residue that is obtained is purified by chromatography (DCM/EtOH 95:5). 330 mg (0.67 mmol, corresponding to 43% of theory) of the product is obtained.

$^1$H-NMR (DMSO): 10.03 (s, 1H), 8.21 (s, 1H), 7.69 (t, 1H), 7.55 (m, 2H), 7.29 (m, 1H), 7.03 (m, 1H), 3.60 (t, 2H), 3.30 (m, 2H), 2.97 (s, 3H), 2.03 (s, 3H), 1.57 (m, 2H), 1.36 (m, 2H). MS: 490 (ES).

14b) N-{3-[(3-Cyano-propyl)-methanesulfonyl-amino]-phenyl}-acetamide

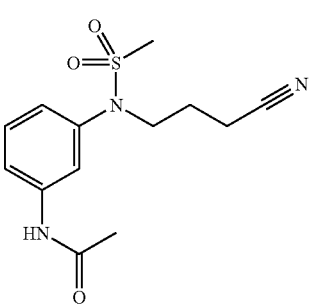

A solution of 510 mg (2.35 mmol) of N-[3-(3-cyano-propylamine)-phenyl]-acetamide in 10 ml of pyridine is mixed at 0° C. drop by drop with 0.21 ml of methanesulfonyl chloride and then stirred for 24 hours at room temperature. After TLC monitoring, it is mixed again with 0.1 ml of methanesulfonyl chloride and stirred for another 3 days. The batch is diluted with ethyl acetate and washed with citric acid (10%), saturated NaHCO$_3$ solution as well as saturated NaCl solution. The organic phase is dried (Na$_2$SO$_4$), filtered and concentrated by evaporation. 469 mg (1.60 mmol, corresponding to 68% of theory) of the product is obtained.

$^1$H-NMR (DMSO): 10.11 (s, 1H), 7.59 (m, 2H), 7.37 (m, 1H), 7.11 (m, 1H), 3.68 (t, 2H), 3.02 (s, 3H), 2.51 (m, 2H), 2.04 (s, 3H), 1.67 (p, 2H). MS: 321 (ES).

14c) N-[3-(3-Cyano-propylamine)-phenyl]-acetamide

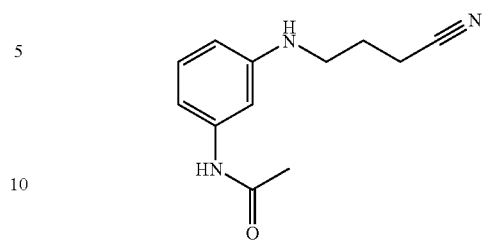

A solution of 3.18 g (21.2 mmol) of N-(3-amino-phenyl)-acetamide in 100 ml of acetonitrile is mixed at room temperature with 1.9 ml (19.0 mmol) of 4-bromobutyric acid nitrile and 2.6 ml of triethylamine and then stirred under reflux overnight. After cooling, it is diluted with ethyl acetate and washed with citric acid (10%), saturated NaHCO$_3$ solution as well as saturated NaCl solution. The organic phase is dried (Na$_2$SO$_4$), filtered and concentrated by evaporation. The residue that is obtained is purified by chromatography (DCM/EtOH 95:5). 0.56 g (2.35 mmol, corresponding to 12% of theory) of the product is obtained.

$^1$H-NMR (DMSO): 9.66 (s, 1H), 6.98 (m, 2H), 6.72 (m, 1H), 6.26 (m, 1H), 5.69 (t, 1H), 3.04 (m, 2H), 2.62 (t, 2H), 2.02 (s, 3H), 1.82 (p, 2H). MS: 218 (ES).

The following compounds are also produced in a way similar to the process variants described above in each case:

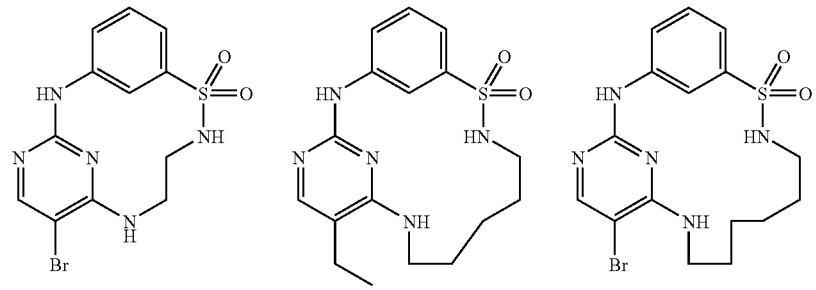

| Example No. | 14.1 | 14.2 | 14.3 |
|---|---|---|---|
| Mass | 370 (ES) | 362 (ES) | 426 (ES) |
| Process Variant | 1 | 1 | 1 |

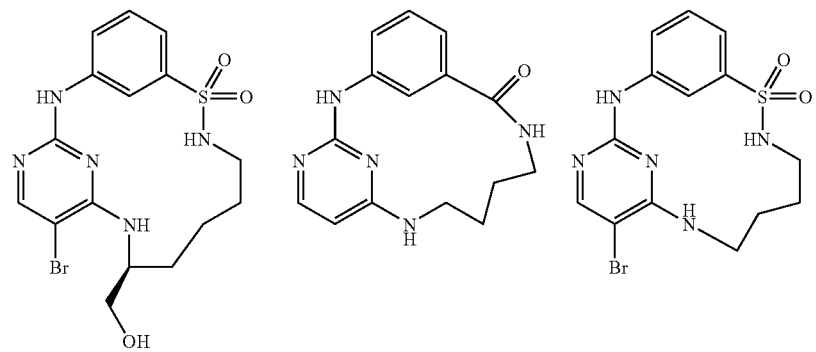

| Example No. | 14.4 | 14.5 | 14.6 |
|---|---|---|---|
| Mass | 442 (ES) | 284 (CI) | 398 (ES) |
| Process Variant | 1 | 13 | 1 |

-continued
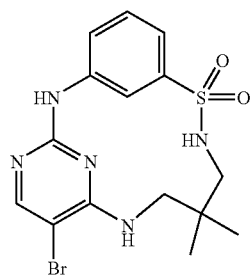 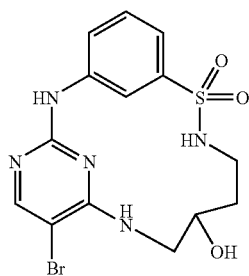 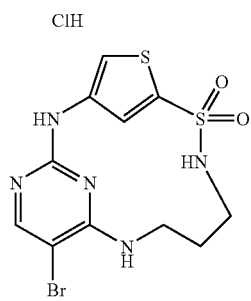
| Example No. | 14.7 | 14.8 | 14.9 |
|---|---|---|---|
| Mass | 412 (ES) | 414 (ES) | 390 (ES) |
| Process Variant | 1 | 1 | 6 |
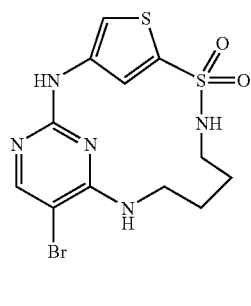 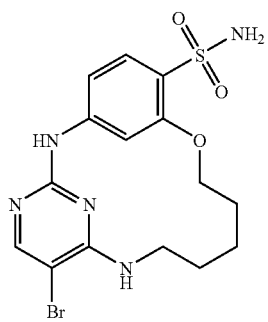 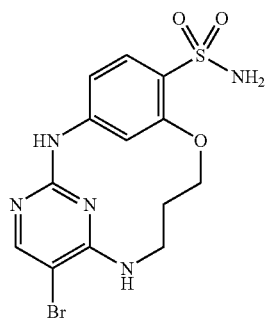
| ExampleNo. | 14.10 | 14.11 | 14.12 |
|---|---|---|---|
| Mass | 404 (ES) | 428 (ES) | 400 (ES) |
| Proc. Var. | 6 | 8 | 8 |
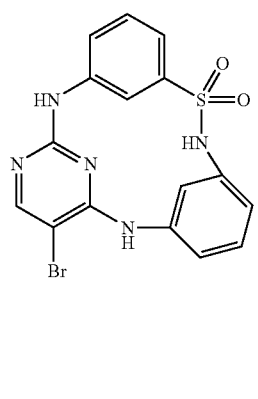 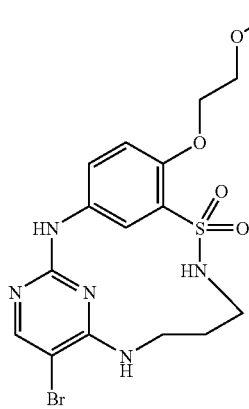 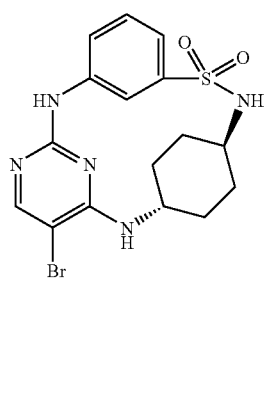
| Example No. | 14.13 | 14.14 | 14.15 |
|---|---|---|---|
| Mass | 418 (ES) | 458 (ES) | 424 (ES) |
| Process Variant | 1 | 1 | 1 |

-continued
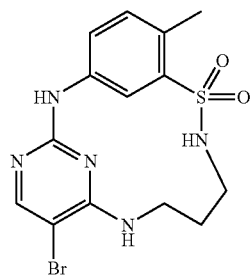 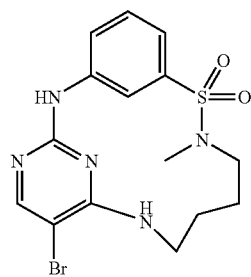 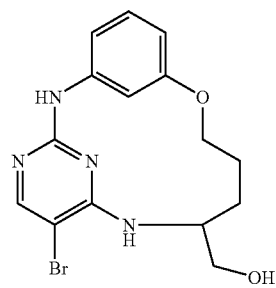
| Example No. | 14.16 | 14.17 | 14.18 |
|---|---|---|---|
| Mass | 398 (ES) | 412 (ES) | 365 (ES) |
| Proc. Var. | 1 | 2 | 1 |
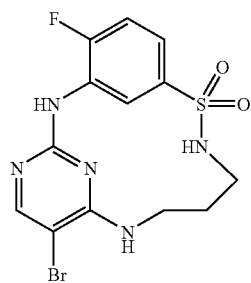 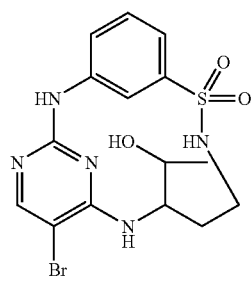 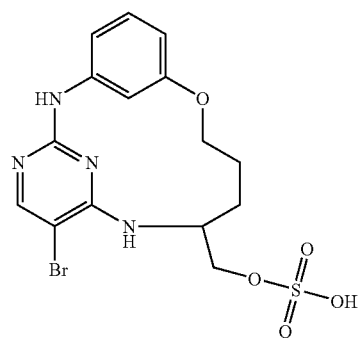
| Example No. | 14.19 | 14.20 | 14.21 |
|---|---|---|---|
| Mass | 402 (ES) | 442 (ES) | 445 (ES) |
| Proc. Var. | 1 | 1 | 1 |
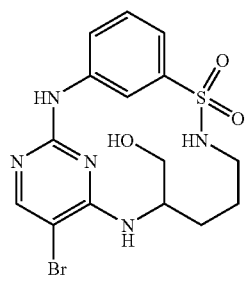 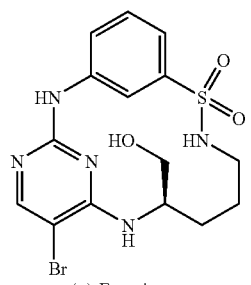 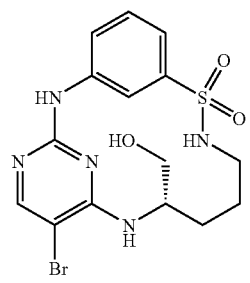
(+)-Enantiomer   (−)-Enantiomer
| Example No. | 14.22 | 14.23 | 14.24 |
|---|---|---|---|
| Mass | 428 (ES) | 428 (ES) | 428 (ES) |
| Proc. Var. | 1 | 1 | 1 |

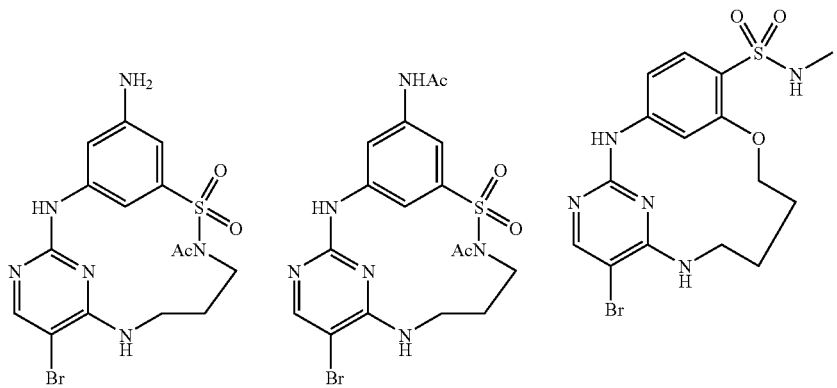

| Example No. | 14.25 | 14.26 | 14.27 |
|---|---|---|---|
| Mass | 441 (ES) | 483 (ES) | 430 (ES) |
| Proc. Var. | 1 | 1 | 8 |

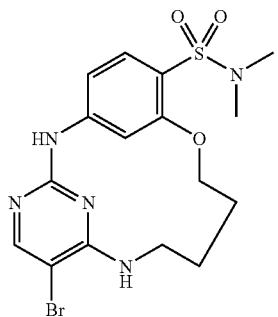

Example No. 14.28
Mass 442 (ES)
Proc. Var. 8

As can be assumed by one skilled in the art, the above-described processes do not describe all possible production methods of the products according to the invention. Related methods are to be obvious to one skilled in the art based on his technical knowledge. In addition, the production processes are not limited to being carried out in this sequence. The chemical transformations and protective groups that are described in this application and that are necessary for the synthesis method are described in the prior art and especially in R. Larock, Comprehensive Organic Transformations, VCH Publishers (1989), T. W. Greene und P. G. M. Wurtz, Protective Groups in Organic Synthesis, John Wiley and Sons (1994) and L. Paquette, ed., Encyclopedia of Reagents for Organic Synthesis, John Wiley and Sons (1995).

The following examples can be obtained analogously to the previously described process variants or the variants that are obvious to one skilled in the art:

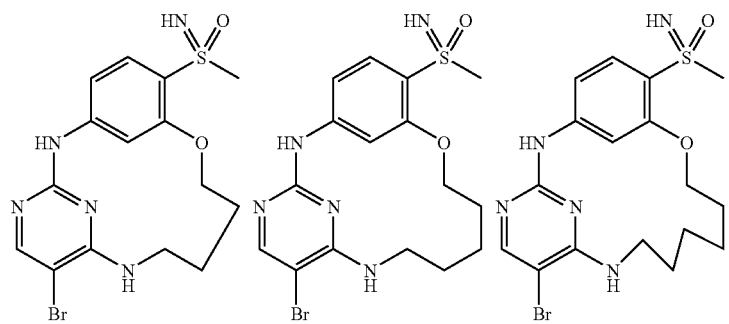

Example 15.0     15.1     15.2

Additional synthesis requirements relative to the sulfoximine derivatives are described in a) M. Regglin, C. Zur, Synthesis, 2000, 1, 1-64. b) S. L. Huang, D. Swem, Phosphorous and Sulfur, 1976, 1, 309-314. c) S. Oae, K. Harada, K. Tsujihara, N. Furukawa, Int. J. Sulfur Chem., Part A, 2, 1, 49-61. d) S. G. Pyne, Sulfur Reports, 12, 1, 57-93.
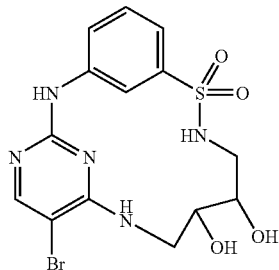 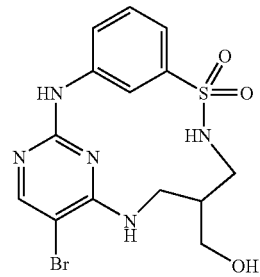 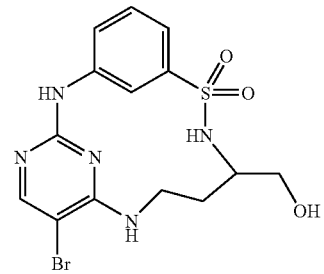
Example No. 15.4     15.5     15.6
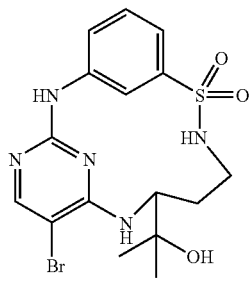 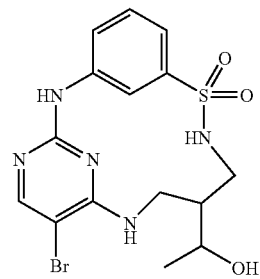 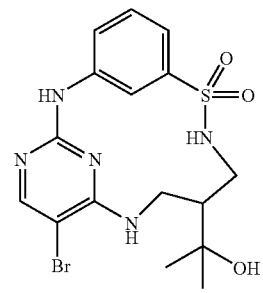
Example No. 15.7     15.8     15.9
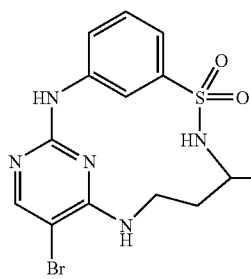 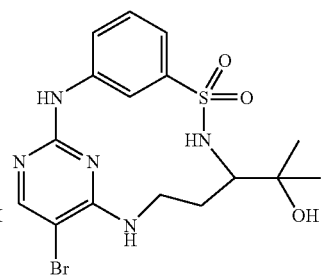 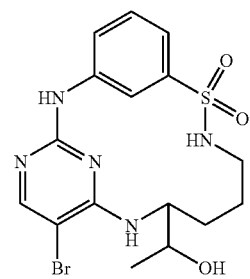
Example No. 15.10     15.11     15.12
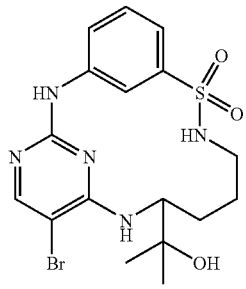 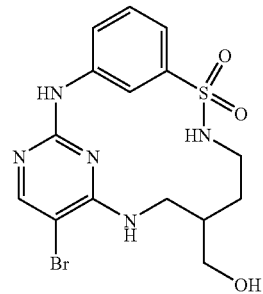 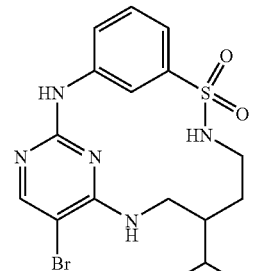
Example No. 15.13     15.14     15.15

-continued
| | | |
|---|---|---|
| 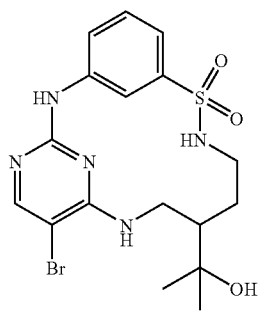 | 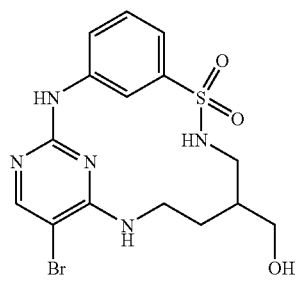 | 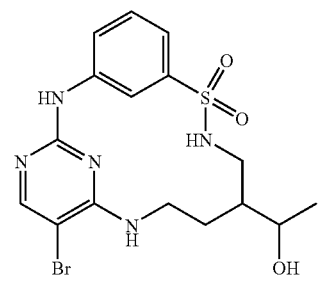 |
| Example No. 15.16 | 15.17 | 15.18 |
| 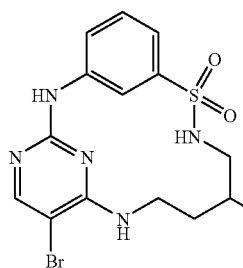 | 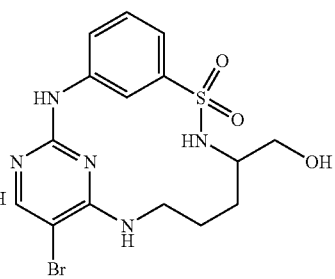 | 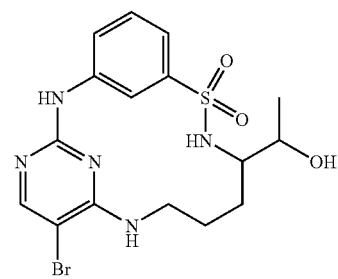 |
| Example No. 15.19 | 15.20 | 15.21 |
| 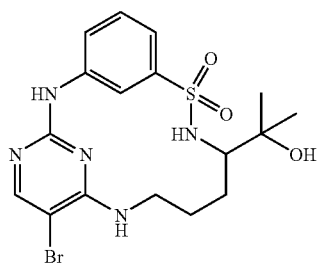 | | |
| Example No. 15.22 | | |
| 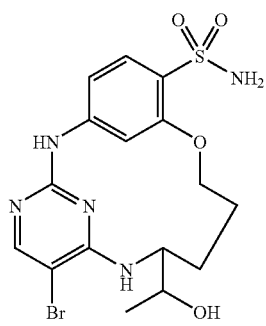 | 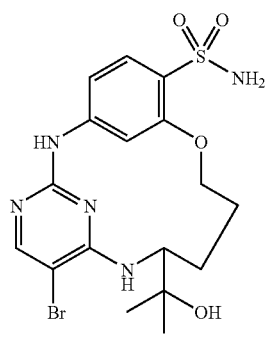 | 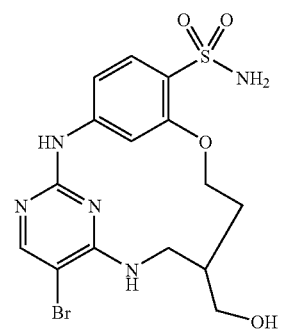 |
| Example No. 15.23 | 15.24 | 15.25 |

| Example No. | | | |
|---|---|---|---|
| 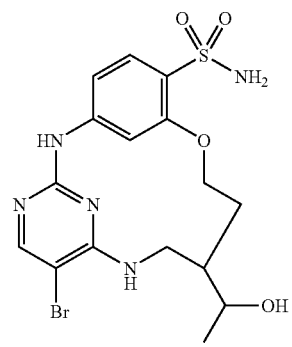 15.26 | 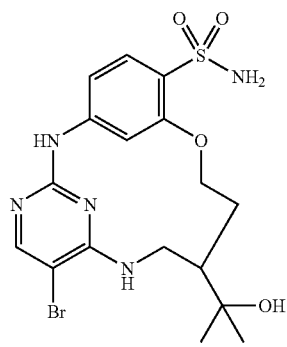 15.27 | 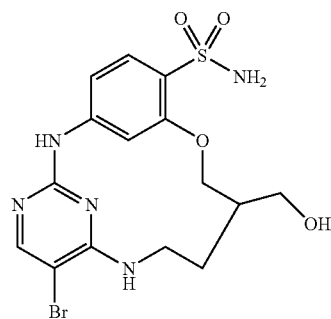 15.28 | |
| 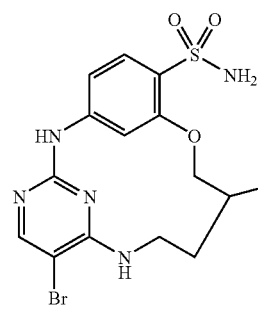 15.29 | 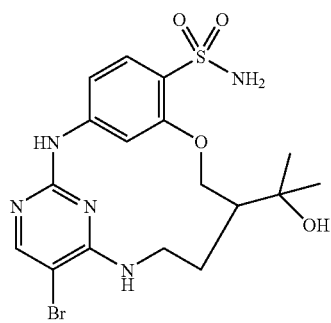 15.30 | 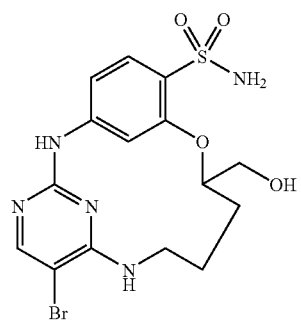 15.31 | |
| 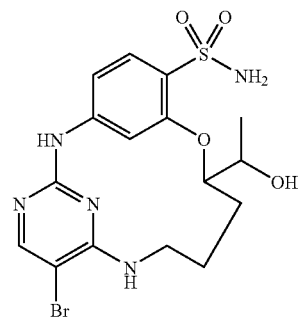 15.32 | 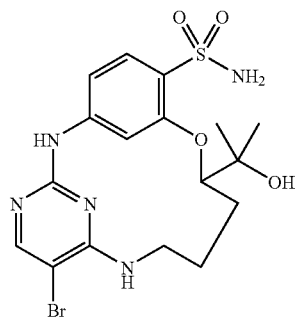 15.33 | | |
| 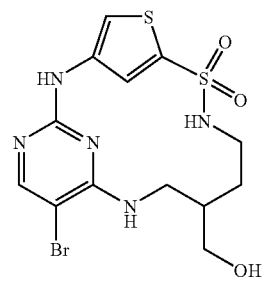 15.34 | 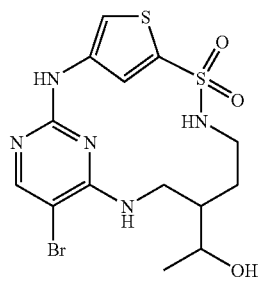 15.35 | 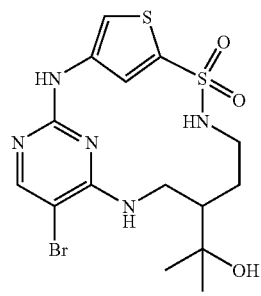 15.36 | |

-continued
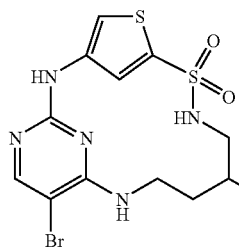 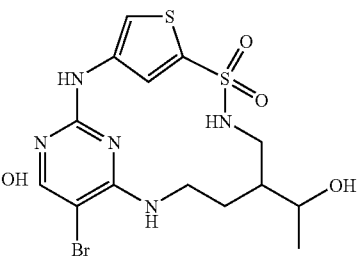 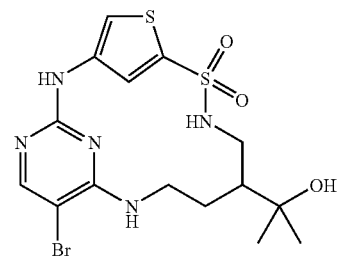
| Example No. | 15.37 | 15.38 | 15.39 |
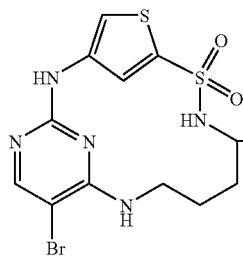 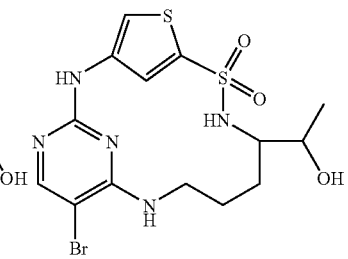 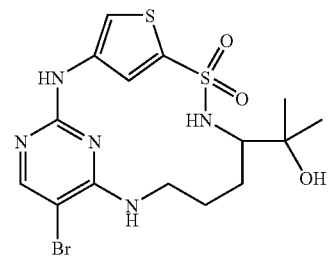
| Example No. | 15.40 | 15.41 | 15.42 |
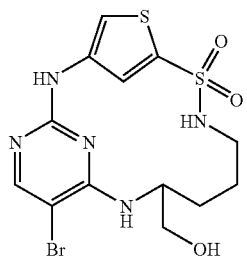 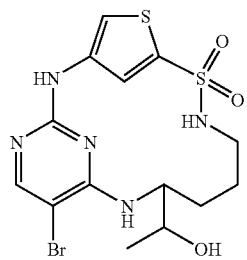 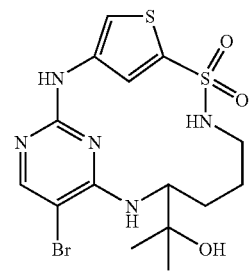
| Example No. | 15.43 | 15.44 | 15.45 |
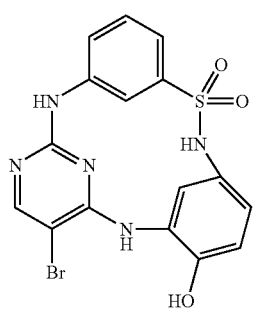 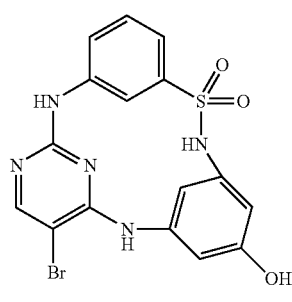 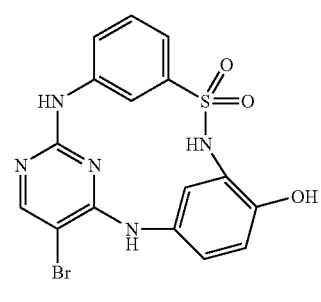
| Example No. | 15.46 | 15.47 | 15.48 |

-continued
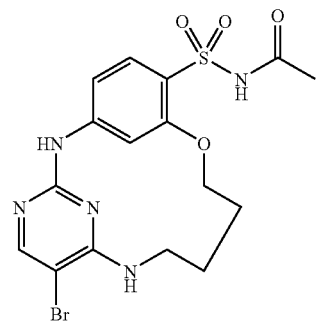 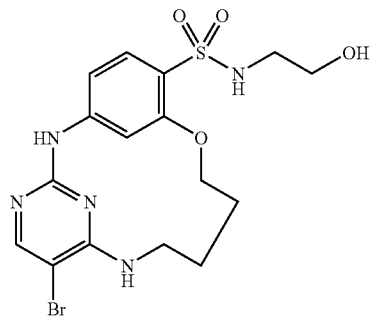 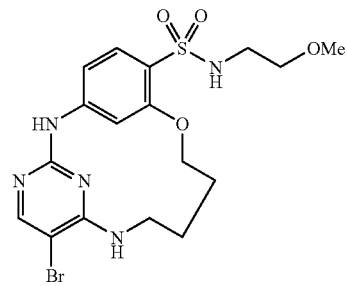
Example No.    15.49    15.50    15.51
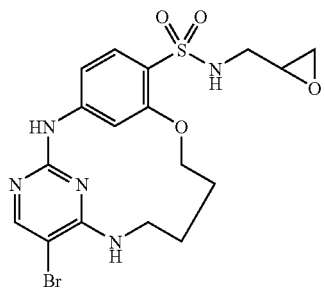 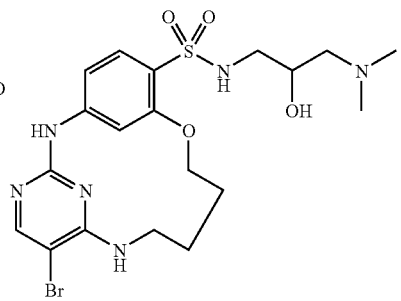 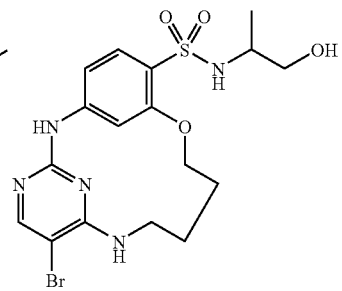
Example No.    15.52    15.53    15.54
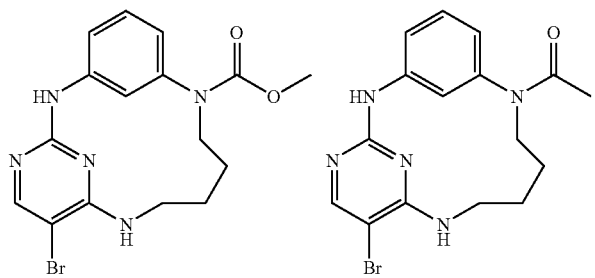 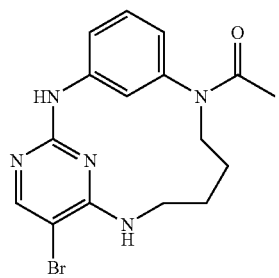 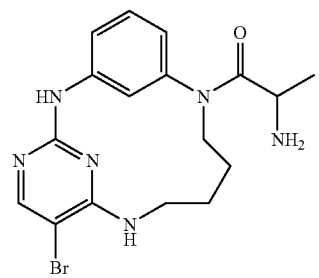
Example No.    15.55    15.56    15.57
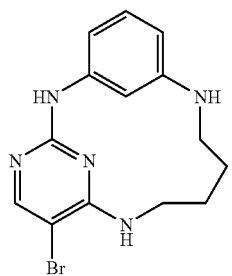 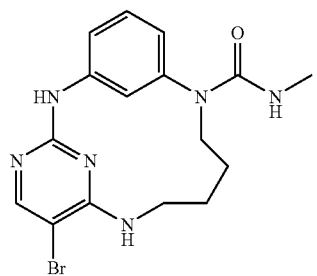 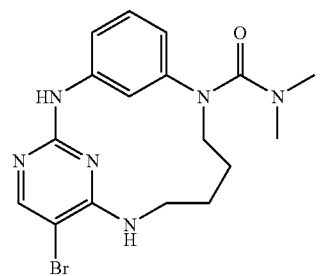
Example No.    15.58    15.59    15.60

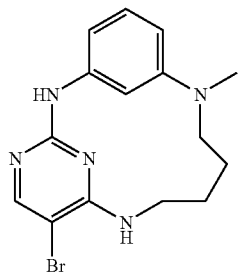 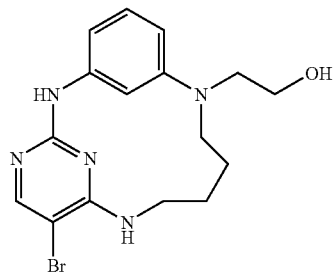 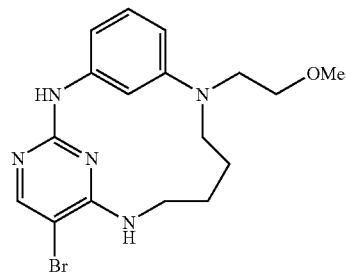
| Example No. | 15.61 | 15.62 | 15.63 |
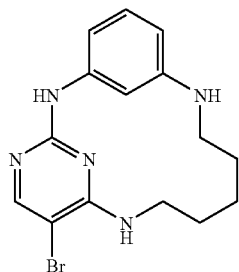 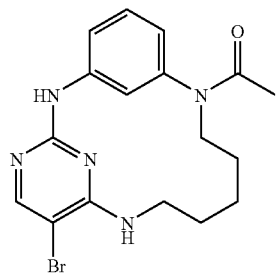 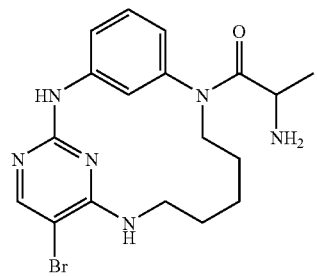
| Example No. | 15.64 | 15.65 | 15.66 |
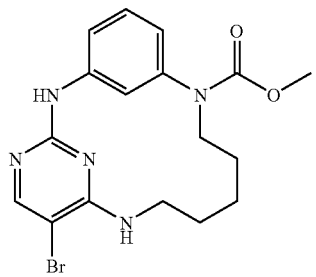 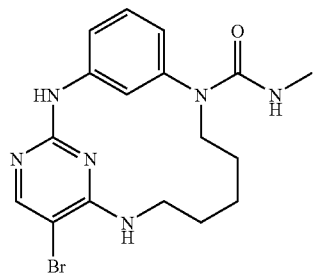 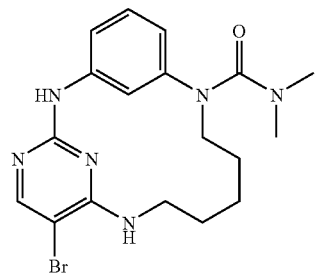
| Example No. | 15.67 | 15.68 | 15.69 |
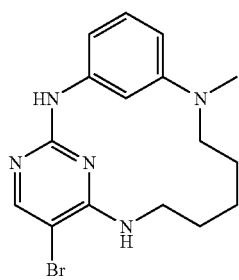 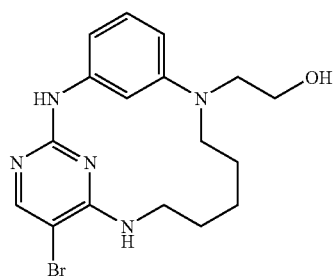 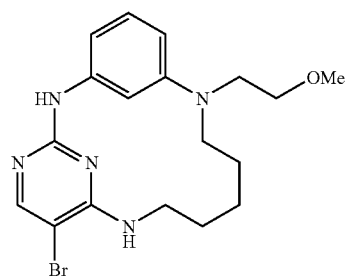
| Example No. | 15.70 | 15.71 | 15.72 |

|  |  |  |
|---|---|---|
| 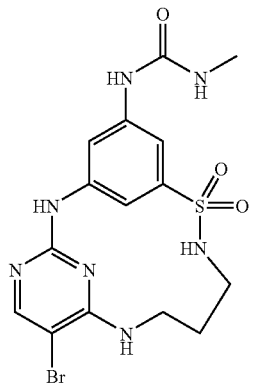 | 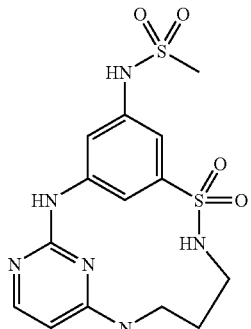 | |
| Example No. 15.73 | 15.74 | |
| 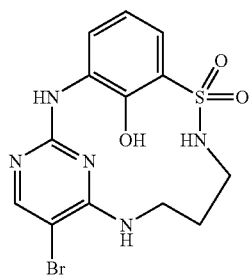 | 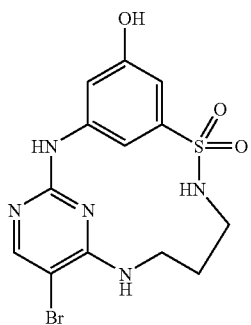 | 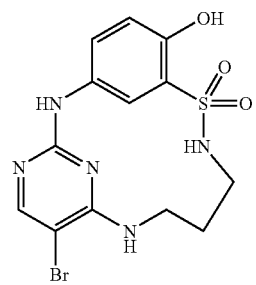 |
| Example No. 15.75<br>Other Related Literature W. G. Watson, Pestic. Sci., 1996, 46, 131-138 | 15.76<br>Yoshida, Bull. Soc. Sci. Photogr. Jpn., 1969, 19,41 | 15.77<br>R. Cremlyn, Phosphorus Sulfur, 1981, 12, 197-204. |
| 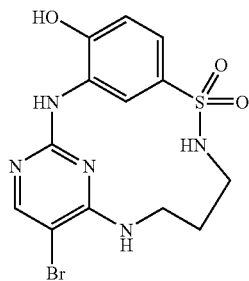 | | |
| Example No. 15.78<br>Other Related Literature Katrizky, Synth. Synth. Commun., 1993, 23, 3, 405-417 | | |
| 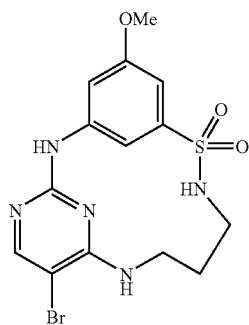 | 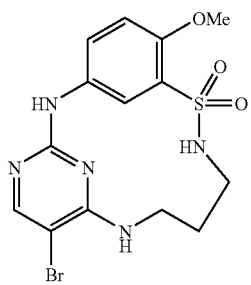 | 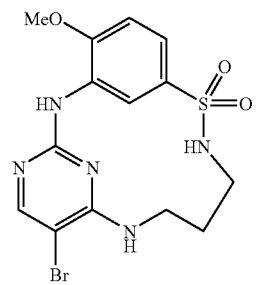 |
| Example No. 15.79 | 15.80 | 15.81 |

-continued

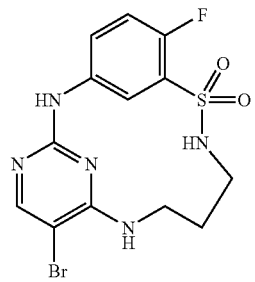 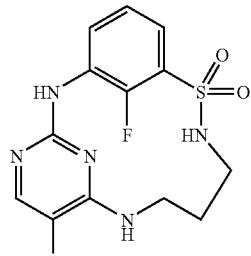

| Example No. | 15.82 | 15.83 |
|---|---|---|
| Other Related Literature | A. Courtin, Helv. Chim. Acta, 1982, 65, 2, 546-550. | A. Courtin, Helv. Chim. Acta, 1983, 66, 1, 68-75 |

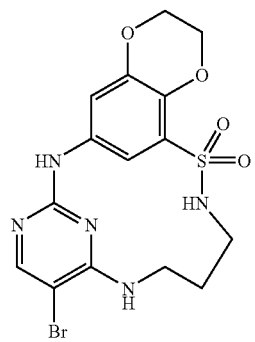 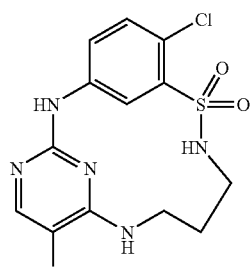 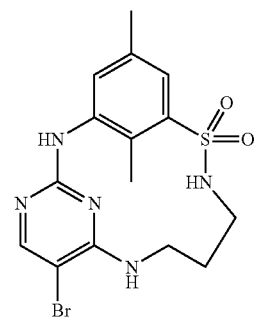

| Example No. | 15.84 | 15.85 | 15.86 |
|---|---|---|---|
| Other Related Literature | Heertjes, Recl. Trav. Chim. Pays-Bas, 1950, 69, 262 | Fischer, Chem. Ber., 1891, 3188 | Karslake, J. Am. Chem. Soc., 1914, 36, 1247 |

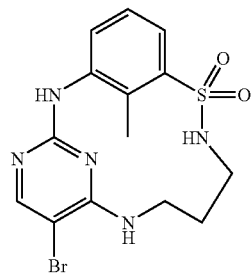 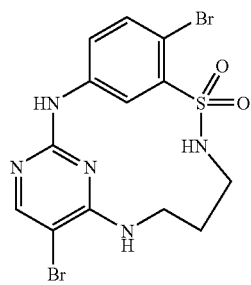

| Example No. | 15.87 | 15.88 |
|---|---|---|
| Other Related Literature | Courtin, Chimica, 1975, 29, 168 | Petrov, J. Pharm. Pharmacol., 1960, 12 |

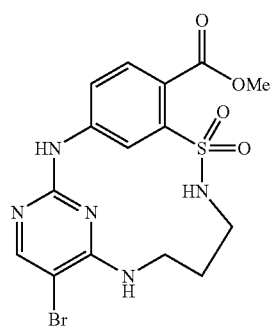 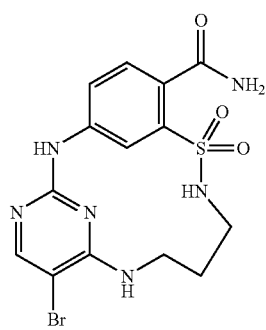 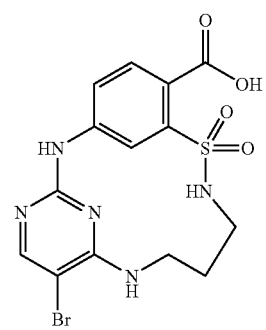

| Example No. | 15.89 | 15.90 | 15.91 |
|---|---|---|---|
| Other Related Literature | G. Remsen, Am. Chem. J., 1897, 1897, 19, 496. | G. Remsen, Am. Chem. J., 1897, 1897, 19, 496. | G. Remsen, Am. Chem. J., 1897, 1897, 19, 496. |

-continued
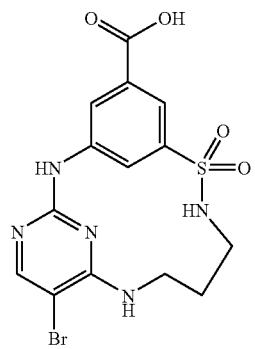 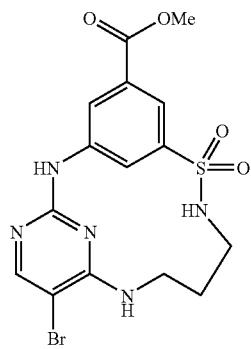 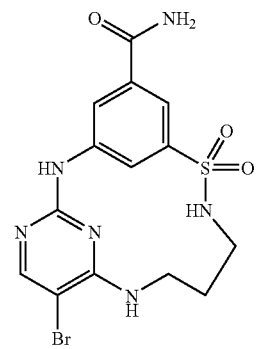
| Example No. | 15.92 | 15.93 | 15.94 |
|---|---|---|---|
| Other Related Literature | Shah, J. Chem. Soc.; 1933, 1373 | Shah, J. Chem. Soc.; 1933, 1373 | Shah, J. Chem. Soc.; 1933, 1373 |
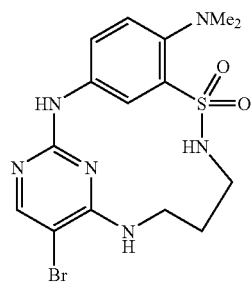 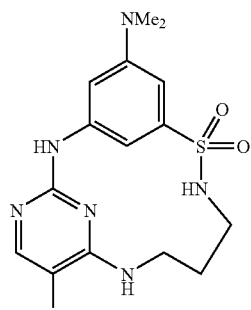 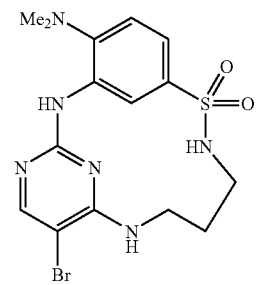
| Example No. | 15.95 | 15.96 | 15.97 |
|---|---|---|---|
| Other Related Literature | Abramovitch, J. Org. Chem. 1977, 42, 2920 | | Wilson, J. Am. Chem. Soc., 1944, 66, 835 |
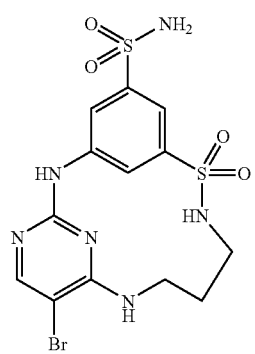 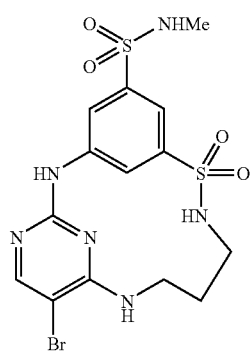 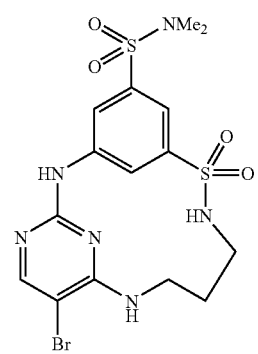
| Example No. | 15.98 | 15.99 | 16.0 |
|---|---|---|---|
| Other Related Literature | Bennett, J. Chem. Soc., 1929, 267 | Bennett, J. Chem. Soc., 1929, 267 | Bennett, J. Chem. Soc., 1929, 267 |

-continued

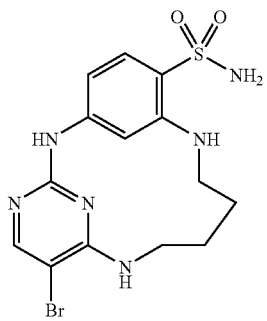
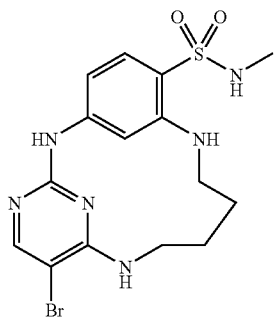
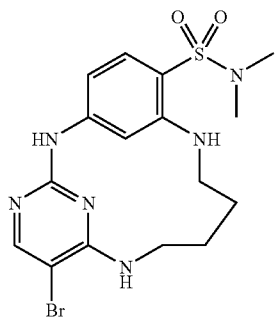

| Example No. | 16.1 | 16.2 | 16.3 |
|---|---|---|---|
| Other Related Literature | Williams, Biochem. J., 1941, 35, 61 | Williams, Biochem. J., 1941, 35, 61 | Williams, Biochem. J., 1941, 35, 61 |

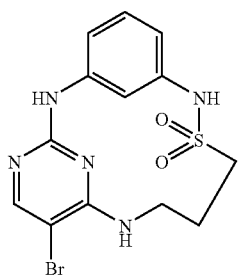
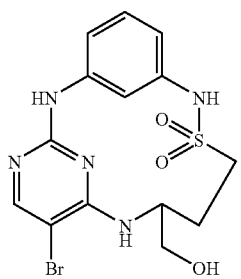

| Example No. | 16.4 | 16.5 |
|---|---|---|
| Other Related Literature | Orus, Pharmazie [Pharmaceutics], 2002, 57, 8, 515 | Orus, Pharmazie, 2002, 57, 8, 515 |

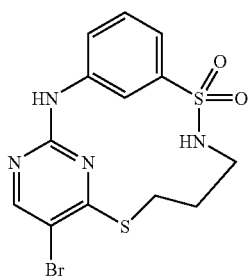
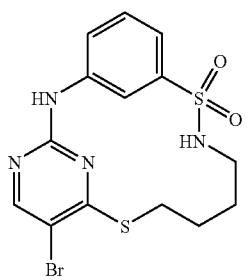

| Example No. | 16.6 | 16.7 |
|---|---|---|
| Other Related Literature | Strekowski, Bull. Acad. Pol. Sci. Ser. Sci. Chim, 1976, 24, 29 | Strekowski, Bull. Acad. Pol. Sci. Ser. Sci. Chim, 1976, 24, 29 |

Secondary or tertiary alcohol derivatives can be produced from primary alcohols via oxidation/Grignard Reaktion, e.g., analogously to the methods of WO 02/096888, pages 186-191. For oxidation, i.a., the TPAP oxidation is suitable (see S. V. Ley, Synthesis, 1994, 639). In Methoden der Org. Chem. [Methods of Organic Chemistry] (Houben-Weyl), 1973, Vol. 13/2a, p. 49, e.g., B. H. Gilman provides an overview on the Grignard reaction.

Additional literature, which provides further information on the production of the respective derivatives, is listed as other literature related to the specific examples The following examples describe the biological action of the compounds according to the invention without limiting the invention to these examples.

EXAMPLE 1

CDK1/CycB Kinase Assay

Recombinant CDK1- and CycB-GST fusion proteins, purified from baculovirus-infected insect cells (Sf9), were purchased from ProQinase GmbH, Freiburg. Histone IIIS, which was used as a kinase substrate, is commercially available from the Sigma Company.

CDK1/CycB (200 ng/measuring point) was incubated for 15 minutes at 22° C. in the presence of various concentrations of test substances (0 μm, as well as within the range of 0.01-100 μm) in assay buffer [50 mmol of tris/HCl, pH 8.0, 10 mmol of $MgCl_2$, 0.1 mmol of Na ortho-vanadate, 1.0 mmol of dithiothreitol, 0.5 μm of adenosine triphosphate (ATP), 10 µg/measuring point of histone IIIS, 0.2 µCi/measuring point of 33P-gamma ATP, 0.05% NP40, 12.5% dimethyl sulfoxide]. The reaction was stopped by adding EDTA solution (250 mmol, pH 8.0, 14 µl/measuring point).

From each reaction batch, 10 µl was applied to P30 filter strips (Wallac Company), and non-incorporated 33P-ATP was removed by three washing cycles of the filter strips for 10 minutes each in 0.5% phosphoric acid. After the filter strips were dried for 1 hour at 70° C., the filter strips were covered with scintillator strips (MeltiLex™ A, Wallac Company) and baked for one hour at 90° C. The amount of incorporated 33P (substrate phosphorylation) was determined by scintillation measurement in a gamma-radiation measuring device (Wallac).

EXAMPLE 2

CDK2/CycE Kinase Assay

Recombinant CDK2- and CycE-GST-fusion proteins, purified from baculovirus-infected insect cells (Sf9), were purchased from ProQinase GmbH, Freiburg. Histone IIIS, which was used as a kinase substrate, was purchased from the Sigma Company.

CDK2/CycE (50 ng/measuring point) was incubated for 15 minutes at 22° C. in the presence of various concentrations of test substances (0 µm, as well as within the range of 0.01-100 µm) in assay buffer [50 mmol of tris/HCl, pH 8.0, 10 mmol of $MgCl_2$, 0.1 mmol of Na ortho-vanadate, 1.0 mmol of dithiothreitol, 0.5 µm of adenosine triphosphate (ATP), 10 µg/measuring point of histone IIIS, 0.2 µCi/measuring point of $^{33}$P-gamma ATP, 0.05% NP40, 12.5% dimethyl sulfoxide]. The reaction was stopped by adding EDTA solution (250 mmol, pH 8.0, 14 µl/measuring point).

From each reaction batch, 10 µl was applied to P30 filter strips (Wallac Company), and non-incorporated $^{33}$P-ATP was removed by subjecting the filter strips to three washing cycles for 10 minutes each in 0.5% phosphoric acid. After the filter strips were dried for one hour at 70° C., the filter strips were covered with scintillator strips (MeltiLex™ A, Wallac Company) and baked for one hour at 90° C. The amount of incorporated $^{33}$P (substrate phosphorylation) was determined by scintillation measurement in a gamma-radiation measuring device (Wallac).

EXAMPLE 3

VEGF Rezeptor-2 Kinase Assay

Recombinant VEGF Receptor tyrosine kinase-2 was purified as GST-fusion protein from baculovirus-infected insect cells (Sf9). Poly-(Glu4Tyr), which was used as a kinase substrate, was purchased from the Sigma Company.

VEGF Receptor tyrosine kinase (90 ng/measuring point) was incubated for 10 minutes at 22° C. in the presence of various concentrations of test substances (0 µmol, as well as within the range of 0.001-30 µM) in 30 µl of assay buffer [40 mmol of Tris/HCl pH 5.5, 10 mmol of MgCl2, 1 mmol of MnCl2, 3 µmol of Na orthovanadate, 1.0 mmol of dithiothreitol, 8 µmol of adenosine trisphosphate (ATP), 27 µg/measuring point of poly-(Glu4Tyr), 0.2 µCi/measuring point of $^{33}$P-gamma ATP, 1% dimethyl sulfoxide]. The reaction was stopped by adding EDTA solution (250 mmol, pH 7.0, 10 µl/measuring point).

From each reaction batch, 10 µl was applied to P30 filter strips (Wallac Company), and non-incorporated 33P-ATP was removed by subjecting the filter strips to three washing cycles for 10 minutes each in 0.5% phosphoric acid. After the filter strips were dried for 1 hour at 70° C., the filter strips were covered with scintillator strips (MeltiLex™ A, Wallac Company) and baked on for 1 hour at 90° C. The amount of incorporated 33P (substrate phosphorylation) was determined by scintillation measurement in a gamma-radiation measuring device (Wallac). The IC50 values are determined from the inhibitor concentration, which is necessary to inhibit the phosphate incorporation to 50% of the uninhibited incorporation after removal of the blank reading (EDTA-stopped reaction).

EXAMPLE 4

Proliferation Assay

Cultivated human tumor cells (MCF7, hormone-independent human breast cancer cells, relative to ATCC HTB22; NCI-H460, human non-small-cell lung cancer cells, ATCC HTB-177, HCT 116, human colon cancer cells, ATCC CCL-247; DU 145, hormone-independent human prostate cancer cells, ATCC HTB-81; MaTu-MDR, hormone-independent, multiple pharmaceutical agent-resistant human breast cancer cells, EPO-GmbH, Berlin) were flattened out at a density of about 5000 cells/measuring point, depending on growth rates of the respective cells in a 96-well multititer plate in 200 µl of the corresponding growth medium. After 24 hours, the cells of one plate (zero-point plate) were colored with crystal violet (see below), while the medium of the other plates was replaced by fresh culture medium (200 µl), to which the test substances were added at various concentrations (0 µmol, as well as in the range of 0.01-30 µmol; the final concentration of the solvent dimethyl sulfoxide was 0.5%). The cells were incubated for 4 days in the presence of test substances. The cell proliferation was determined by coloring the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were colored by adding 100 µl/measuring point of a 0.1% crystal violet solution (pH was set at 3 by adding acetic acid). After three washing cycles of the colored cells with water, the plates were dried at room temperature. The dye was dissolved by adding 100 µl/measuring point of a 10% acetic acid solution. The extinction was determined by photometry at a wavelength of 595 nm. The change of cell growth, in percent, was calculated by standardization of the measured values to the extinction values of the zero-point plate (=0%) and the extinction of the untreated (0 µm) cells (=100%).

The results from the examples are indicated in the following tables.

TABLE I

| Example No. | CDK2/CycE IC$_{50}$ [nM] | CDK1/CycB IC$_{50}$ [nM] | VEGF-R2 IC$_{50}$ [nM] | MCF7 IC$_{50}$ [µM] |
|---|---|---|---|---|
| 1.0 | 420 | 200 | | 1.1 |
| 1.1 | 140 | 20 | 40 | 0.2 |
| 1.2 | 510 | 40 | | 2.6 |
| 1.3 | 23 | 28 | <10 | 1.0 |
| 1.3 (+) Enantiomer | 23 | | 69 | 0.9 |
| 1.4 | | | 11 | 0.4 |
| 1.5 | | 28 | 69 | 0.9 |
| 3.0 | 160 | 50 | 89 | 1.6 |
| 5.0 | | 300 | | |
| 8.0 | 130 | 80 | 140 | 1.3 |
| 10.0 | 120 | 360 | | 6 |
| 14.4 | 250 | 1700 | | 4.0 |
| 14.15 | 130 | 1500 | | 1.3 |
| 14.6 | 320 | 90 | | 0.7 |
| 14.8 | | 200 | | |
| 14.10 | 65 | | 190 | 1.9 |
| 14.11 | 2400 | 200 | | 0.75 |
| 14.16 | 4400 | 300 | | >10 |
| 14.18 | 30 | 80 | 370 | 2.1 |

From the results of the table, it is clearly evident that the macrocyclic pyrimidines according to the invention are distinguished as CDK- and VEGF-receptor inhibitors or CDK1- or CDK2-inhibitors or as VEGF-receptor inhibitors. The activity compared to CDK1 and/or CDK2 and/or VEGF explains, i.a., the cellular action of the substances. Thus, the macrocyclic compounds are clearly superior to the previously known compounds.

TABLE II

| | Inhibition IC$_{50}$ [nM] | Proliferation IC$_{50}$ [µM] | | | | |
|---|---|---|---|---|---|---|
| Example No. | CDK2/CycE | MCF7 | H460 | HCT116 | DU145 | MaTu-ADR |
| 1.0 | 420 | 1.1 | 1.8 | 1.3 | 2.0 | 0.7 |
| 1.1 | 140 | 0.2 | 0.3 | 0.2 | 2.2 | 0.12 |
| 1.3 | 23 | 1.0 | 1.7 | 0.9 | 2.9 | 2.8 |
| 1.4 | | 0.4 | 0.2 | <0.1 | 0.7 | 0.1 |
| 1.5 | | 0.9 | 0.6 | 0.4 | 1.3 | 0.6 |
| 7.1 | 2400 | 4 | | | | |
| 8.0 | 130 | 1.3 | 0.5 | 0.4 | 0.5 | 0.4 |
| 13.0 A | 7000 | 30 | | | | |
| 13.0 B | >10000 | | | | | |
| 14.2 | 5000 | | | | | |
| 14.4 | 2000 | | | | | |
| 14.6 | 320 | 0.7 | 0.7 | 0.5 | 1.7 | 0.3 |
| 14.10 | | 0.3 | 0.1 | 0.1 | 0.4 | |
| 14.11 | 2400 | 0.75 | 0.9 | 0.7 | 0.9 | 1.3 |
| 14.15 | 1500 | 1.3 | 1.2 | 1.0 | 1.2 | 1.3 |
| 1.3 (+)Enantiomer | 23 | 0.9 | 2.1 | 1.4 | 4 | 4 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius, and all parts and percentages are by weight, unless otherwise indicated.

The entire disclosure[s] of all applications, patents, and publications, cited herein and of corresponding German Application No. 10239042.8, filed Aug. 21, 2002, and U.S. Provisional Application Ser. No. 60/413,444, filed Sep. 26, 2003, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

The invention claimed is:
1. Compounds of formula I

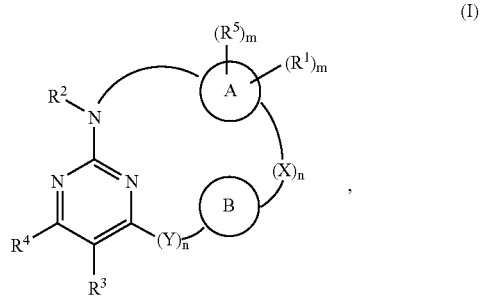

in which
  A stands for phenylene,
  B stands for a bond or for $C_1$-$C_{12}$-alkylene, $C_2$-$C_{12}$-alkenylene, $C_2$-$C_{12}$-alkinylene, $C_3$-$C_8$-cycloalkylene, or phenylene that is optionally substituted in one or more places in the same way or differently with hydroxy, halogen, cyano, nitro, $C_1$-$C_6$-alkyl, $C_2$-$C_6$-alkenyl, $C_2$-$C_6$-alkinyl, $C_3$-$C_{10}$-cycloalkyl, $C_1$-$C_6$-hydroxyalkyl, —$(CH_2)_pSO_3R^8$, or with the group —$NR^8R^9$, —$NR^8COR^9$, —$NR^8CSR^9$, —$NR^8SOR^9$, —$NR^8SO_2R^9$, —$NR^8CONR^8R^9$, —$NR^8COOR^9$, —$NR^8C(NH)NR^9R^{10}$, —$NR^8CSNR^9R^{10}$, —$NR^8SONR^9R^{10}$, —$NR^8SO_2NR^9R^{10}$, —$COR^8$, —$CSR^8$, —$S(O)R^8$, —$S(O)_2R^8$, —$S(O)_2NR^8R^9$, —$SO_3R^8$, —$CO_2R^8$, —$CONR^8R^9$, —$CSNR^8R^9$, —$SR^8$ or —$CR^8(OH)$—$R^9$,
  X and Y, in each case independently of one another, stand for oxygen, sulfur or for the group —$NR^{11}$, —$NR^{11}$ (CH$_2$)—, —NR$^{11}$O—, —ONR$^{11}$—, =CR$^6$R$^7$, =C=O, =C=S, =SO, =SO$_2$, —C(O)O—, —OC(O)—, —S(O)O—, —OS(O)—, —S(O)$_2$O—, —OS(O)$_2$—, —CONR$^8$—, —N(COR$^8$)—, —N(COOR$^8$)—, —N(CONR$^8$R$^9$)—, —NR$^8$CO—, —OCONR$^8$—, —NR$^8$C(O)O—, —CSNR$^8$—, —NR$^8$CS—, —OCSNR$^8$—, —NR$^8$CSO—, —SONR$^8$—, —NR$^8$SO—, —SO$_2$NR$^8$—, —S(O)$_2$N(COR$^8$)—, —NR$^8$SO$_2$—, —NR$^8$CONR$^9$—, —NR$^8$CSNR$^9$—, —NR$^8$SONR$^9$—, —NR$^8$SO$_2$NR$^9$—, —NR$^8$C(O)NR$^9$— or —NR$^8$C(S)NR$^9$—, R$^1$ and R$^5$, in each case independently of one another, stand for hydrogen, hydroxy, halogen, nitro, cyano, C$_1$-C$_6$-alkyl, C$_2$-C$_6$-alkenyl, C$_2$-C$_6$-alkinyl, C$_3$-C$_{10}$-cycloalkyl, the group —C$_1$-C$_6$-alkyloxy-C$_1$-C$_6$-alkyloxy, —(CH$_2$)$_p$PO$_3$(R$^{10}$)$_2$, —NR$^8$R$^9$, —NR$^8$COR$^9$, —NR$^8$CSR$^9$, —NR$^8$SOR$^9$, —NR$^8$SO$_2$R$^9$, —NR$^8$CONR$^9$R$^{10}$, —NR$^8$COOR$^9$, —NR$^8$C(NH)NR$^9$R$^{10}$, —NR$^8$CSNR$^9$R$^{10}$, —NR$^8$SONR$^9$R$^{10}$, —NR$^8$SO$_2$NR$^9$R$^{10}$—, —COR$^8$, —CSR$^8$, —S(O)R$^8$, —S(O)(NH)R$^8$, —S(O)$_2$R$^8$, —S(O)$_2$NR$^8$R$^9$, —S(O)$_2$N=CH—NR$^8$R$^9$—, SO$_3$R$^8$, —CO$_2$H, —CO$_2$R$^8$, —CONR$^8$R$^9$, —CSNR$^8$R$^9$, —SR$^8$ or —CR$^8$(OH)—R$^9$, or for C$_1$-C$_{10}$-alkyl, C$_2$-C$_{10}$-alkenyl, C$_2$-C$_{10}$-alkinyl, or C$_3$-C$_{10}$-cycloalkyl, that is substituted in one or more places in the same way or differently with hydroxy, C$_1$-C$_6$-alkoxy, halogen, phenyl or with the group —NR$^3$R$^4$, and the phenyl, C$_3$-C$_{10}$-cycloalkyl, C$_3$-C$_{12}$-aryl, and —(CH$_2$)$_p$—C$_3$-C$_{18}$-heteroaryl itself optionally can be substituted in one or more places in the same way or differently with halogen, hydroxy, C$_1$-C$_6$-alkyl, C$_1$-C$_6$-alkoxy, or with the group —CF$_3$ or —OCF$_3$—, R$^2$ stands for hydrogen or C$_1$-C$_{10}$-alkyl, R$^3$ stands for hydrogen, halogen, nitro, cyano, C$_1$-C$_{10}$-alkyl, halo-C$_1$-C$_{10}$-alkyl, C$_2$-C$_{10}$-alkenyl, C$_2$-C$_{10}$-alkinyl, C$_3$-C$_{10}$-cycloalkyl, hydroxy, C$_1$-C$_6$-alkoxy, C$_1$-C$_6$-alkylthio, amino, —NH—(CH$_2$)$_p$—C$_3$-C$_{10}$-cycloalkyl, C$_1$-C$_6$-hydroxyalkyl, C$_1$-C$_6$-alkoxy-C$_1$-C$_6$-alkyl, C$_1$-C$_6$-alkoxy-C$_1$-C$_6$-alkoxy-C$_1$-C$_6$-alkyl, —NHC$_1$-C$_6$-alkyl, —N(C$_1$-C$_6$-alkyl)$_2$, —SO(C$_1$-C$_6$-alkyl), —SO$_2$(C$_1$-C$_6$-alkyl), C$_1$-C$_6$-alkanoyl, —CONR$^8$R$^9$, —COR$^{10}$, C$_1$-C$_6$-alkylOAc, carboxy, or for the group —NR$^8$R$^9$, or for C$_1$-C$_{10}$-alkyl, C$_2$-C$_{10}$-alkenyl, C$_2$-C$_{10}$-alkinyl, or C$_3$-C$_{10}$-cycloalkyl, that is substituted in one or more places in the same way or differently with hydroxy, halogen, C$_1$-C$_6$-alkoxy, C$_1$-C$_6$-alkylthio, amino, cyano, C$_1$-C$_6$-alkyl, —NH—(CH$_2$)$_p$—C$_3$-C$_{10}$-cycloalkyl, C$_3$-C$_{10}$-cycloalkyl, C$_1$-C$_6$-hydroxyalkyl, C$_2$-C$_6$-alkenyl, C$_2$-C$_6$-alkinyl, C$_1$-C$_6$-alkoxy-C$_1$-C$_6$-alkyl, C$_1$-C$_6$-alkoxy-C$_1$-C$_6$-alkoxy-C$_1$-C$_6$-alkyl, —NHC$_1$-C$_6$-alkyl, —N(C$_1$-C$_6$-alkyl)$_2$, —SO(C$_1$-C$_6$-alkyl), —SO$_2$(C$_1$-C$_6$-alkyl), C$_1$-C$_6$-alkanoyl, —CONR$^8$R$^9$, —COR$^{10}$, C$_1$-C$_6$-alkylOAc, carboxy, —(CH$_2$)$_p$PO$_3$(R$^{10}$)$_2$ or with the group —NR$^8$R$^9$, R$^4$ stands for hydrogen, halogen or C$_1$-C$_4$-alkyl,

R$^6$, R$^7$, R$^8$,

R$^9$, R$^{10}$ and R$^{11}$, in each case independently of one another, stand for hydrogen or for C$_1$-C$_{10}$-alkyl, C$_2$-C$_{10}$-alkenyl, C$_2$-C$_{10}$-alkinyl, C$_3$-C$_{10}$-cycloalkyl, m stands for 0 to 8, and n and p stand for 0 to 6, or isomers, diastereomers, enantiomers and salts thereof.

2. Compounds of formula (I),

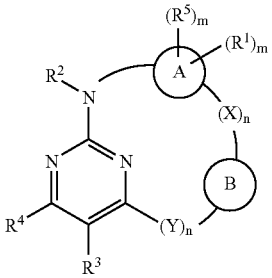

in which

A stands for phenylene,

B stands for a bond or for C$_1$-C$_{12}$-alkylene, C$_3$-C$_8$-cycloalkylene, or phenylene or thiophenylene that is optionally substituted in one or more places in the same way or differently with hydroxy, C$_1$-C$_6$-alkyl, C$_1$-C$_6$-hydroxyalkyl or —(CH$_2$)$_p$SO$_3$R$^8$, X and Y, in each case independently of one another, stand for oxygen, or for the group —NR$^{11}$—, —NR$^{11}$(CH$_2$)—, —CONR$^8$—, —SO$_2$NR$^8$— or —NR$^8$CONR$^9$—, R$^1$ and R$^5$, in each case independently of one another, stand for hydrogen, halogen, nitro, C$_1$-C$_6$-alkyl, or for —NR$^8$R$^9$, —C$_1$-C$_6$-alkyloxy-C$_1$C$_6$-alkyloxy or —S(O)$_2$NR$^8$R$^9$, R$^2$ stands for hydrogen, R$^3$ stands for hydrogen, halogen, cyano, C$_1$-C$_{10}$-alkyl or —CONR$^8$R$^9$, R$^4$ stands for hydrogen,

R$^8$,

R$^9$, and R$^{11}$, in each case independently of one another, stand for hydrogen or for C$_1$-C$_{10}$-alkyl, n stands for 0 to 6, m stands for 0 to 4, and p stands for 0 to 6, or isomers, diastereomers, enantiomers and salts thereof.

3. Compounds of formula (I), according to claim 2, in which

A stands for phenylene,

B stands for a bond or for C$_1$-C$_{12}$-alkylene, cyclohexylene or phenylene that is optionally substituted in one or more places in the same way or differently with hydroxy, C$_1$-C$_6$-alkyl, C$_1$-C$_6$-hydroxyalkyl or —(CH$_2$)SO$_3$R$^8$, X stands for oxygen or for the group —CONR$^8$—, —SO$_2$NR$^8$— or —NR$^8$CONR$^9$—, Y stands for oxygen or for the group —NR$^{11}$—, R$^1$ and R$^5$, in each case independently of one another, stand for hydrogen, amino, halogen, nitro, C$_1$-C$_6$-alkyl, or for the group —NR$^8$R$^9$, —C$_1$-C$_6$-alkyloxy-C$_1$-C$_6$-alkyloxy or —S(O)$_2$NR$^8$R$^9$, R$^2$ stands for hydrogen, R$^3$ stands for hydrogen, halogen, cyano, C$_1$-C$_{10}$-alkyl, or —CONR$^8$R$^9$, R$^4$ stands for hydrogen, R$^8$, R$^9$ and R$^{11}$, in each case independently of one another, stand for hydrogen or for methyl or isobutyl, m stands for 0 to 4, and p stands for 0 to 6, as well as isomers, diastereomers, enantiomers, and salts thereof.

4. Compounds of formula (I), according to claim 2, in which
A stands for phenylene,
B stands for a bond or for $C_1$-$C_{12}$-alkylene that is optionally substituted in one or more places in the same way or differently with hydroxy, $C_1$-$C_6$-hydroxyalkyl or —$(CH_2)SO_3R^8$,
X stands for oxygen or for the group —$SO_2NR^8$— or —$NR^8CONR^9$—,
Y stands for the group —$NR^{11}$—,
$R^1$ and $R^5$, in each case independently of one another, stand for hydrogen, amino, halogen, nitro or for the group —$S(O)_2NR^8R^9$,
$R^2$ stands for hydrogen,
$R^3$ stands for halogen or cyano,
$R^4$ stands for hydrogen,
$R^8$, $R^9$ and $R^{11}$ in each case stand for hydrogen, and
m stands for 0 to 4,
or isomers, diastereomers, enantiomers and salts thereof.

5. Process for the production of the compounds of formula I according to claim 1, wherein either
a) compounds of formula VIII

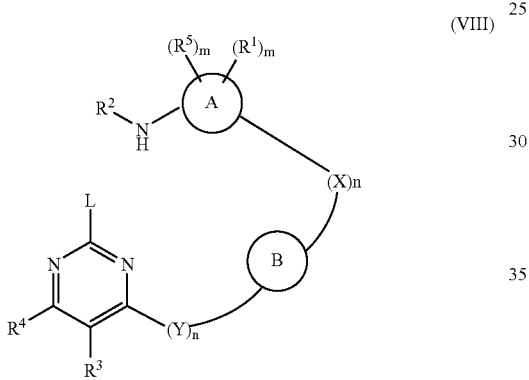

(VIII)

in which $R^1$, $R^2$, $R^3$, $R^4$, $R^5$, X, Y, A, B, m and n have the meanings that are indicated in formula I, and L stands for a leaving group, are cyclized with a an acid to compounds of formula I, or b) the acyclic precursors of formula (IX)

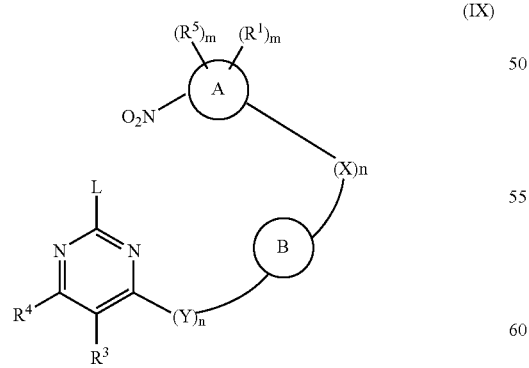

(IX)

in which $R^1$, $R^3$, $R^4$, $R^5$, X, Y, A, B, m and n have the meanings that are indicated in formula I, and L stands for a leaving group, are first reduced to amine in a solvent and a reducing agent at 0° C. until reflux takes place and then the intermediately formed amine is cyclized to the compounds of formula I.

6. A method for the treatment of hormone-independent human breast cancer, human nonsmall-cell lung cancer, human colon cancer, hormone-independent human prostate cancer, or hormone-independent, multiple pharmaceutical agent-resistant human breast cancer, comprising administering to a host in need thereof a compound of formula I according to claim 1.

7. A pharmaceutical composition, comprising at least one compound according to claim 1 and a pharmaceutically acceptable carrier.

8. A pharmaceutical composition, comprising compound according to claim 2 and suitable formulation substances and vehicles.

9. Compounds of formula I

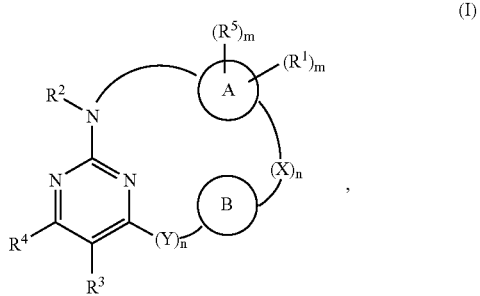

(I)

in which
A stands for phenylene,
B stands for $C_1$-$C_{12}$-alkylene, $C_3$-$C_8$-cycloalkylene, or phenylene that is optionally substituted in one or more places in the same way or differently with hydroxy, $C_1$-$C_6$-alkyl, $C_1$-$C_6$-hydroxyalkyl, or —$(CH_2)_pSO_3R^8$,
X and Y, in each case independently of one another, stand for oxygen, sulfur or for the group —$NR^{11}$—, —$NR^{11}(CH_2)$—, —$CONR^8$—, —$SO_2NR^8$, —$S(O)_2N(COR^8)$—, —$NR^8SO_2$—, or —$NR^8CONR^9$—,
$R^1$ and $R^5$, in each case independently of one another, stand for hydrogen, halogen, nitro, $C_1$-$C_6$-alkyl or for the group —$C_1$-$C_6$-alkyloxy-$C_1$-$C_6$-alkyloxy, —$NR^8R^9$, —$NR^8COR^9$, —$S(O)_2NR^8R^9$, —$S(O)_2N=CH$—$NR^8R^9$, —$CO_2H$, —$CO_2R^8$, —$CONR^8R^9$,
$R^2$ stands for hydrogen,
$R^3$ stands for hydrogen, halogen, cyano, $C_1$-$C_{10}$-alkyl, —$CONR^8R^9$,
$R^4$ stands for hydrogen,
$R^6$, $R^7$, $R^8$,
$R^9$, $R^{10}$
and $R^{11}$, in each case independently of one another, stand for hydrogen or for $C_1$-$C_{10}$-alkyl, $C_2$-$C_{10}$-alkenyl, —$N(C_1$-$C_6$-alkyl$)_2$, or —$SO(C_1$-$C_6$-alkyl),
m stands for 0 to 8,
p stands for 0 to 6, and
n stands for 1
or diastereomers, enantiomers or salts thereof.

* * * * *